US012668810B2

(12) United States Patent
Yamamura et al.

(10) Patent No.: US 12,668,810 B2
(45) Date of Patent: Jun. 30, 2026

(54) EXON-HUMANIZED MOUSE

(71) Applicant: TRANSGENIC INC., Fukuoka (JP)

(72) Inventors: Kenichi Yamamura, Kobe (JP);
Zhenghua Li, Kobe (JP)

(73) Assignee: TRANSGENIC INC., Fukuoka (JP)

( * ) Notice: Subject to any disclaimer, the term of this patent is extended or adjusted under 35 U.S.C. 154(b) by 955 days.

(21) Appl. No.: 17/614,237

(22) PCT Filed: May 27, 2019

(86) PCT No.: PCT/JP2019/021894
§ 371 (c)(1),
(2) Date: Nov. 24, 2021

(87) PCT Pub. No.: WO2020/240876
PCT Pub. Date: Dec. 3, 2020

(65) Prior Publication Data
US 2022/0340926 A1 Oct. 27, 2022

(51) Int. Cl.
*A01K 67/0278* (2024.01)
*C12N 15/11* (2006.01)
*C12N 15/85* (2006.01)

(52) U.S. Cl.
CPC ...... *C12N 15/8509* (2013.01); *A01K 67/0278* (2013.01); *C12N 15/11* (2013.01); *A01K 2207/15* (2013.01); *A01K 2227/105* (2013.01); *A01K 2267/03* (2013.01); *C12N 2015/8536* (2013.01); *C12N 2310/20* (2017.05)

(58) Field of Classification Search
CPC C12N 15/8509; C12N 15/11; C12N 2310/20; C12N 2015/8536; A01K 67/0278; A01K 2207/15; A01K 2227/105; A01K 2267/03
See application file for complete search history.

(56) References Cited

U.S. PATENT DOCUMENTS

| | | |
|---|---|---|
| 2003/0177515 A1 | 9/2003 | Wu et al. |
| 2013/0219535 A1 | 8/2013 | Wabl et al. |
| 2014/0047572 A1 | 2/2014 | Chen et al. |
| 2014/0309487 A1 | 10/2014 | Lee et al. |
| 2015/0159174 A1* | 6/2015 | Frendewey .......... C12N 15/907 800/21 |
| 2019/0098879 A1 | 4/2019 | Drummond-Samuelson et al. |

FOREIGN PATENT DOCUMENTS

| | | |
|---|---|---|
| CN | 104378975 A | 2/2015 |
| CN | 107709550 A | 2/2018 |
| CN | 108866101 A | 11/2018 |
| FR | 2 861 255 A1 | 4/2005 |
| JP | 2000-209980 A | 8/2000 |
| JP | 2007-28 A | 1/2007 |
| JP | 2013-535202 A | 9/2013 |
| JP | 2016-539655 A | 12/2016 |

| | | |
|---|---|---|
| WO | WO 2014/028509 A2 | 2/2014 |
| WO | WO 2014/164640 A1 | 10/2014 |
| WO | WO 2019/067875 A1 | 4/2019 |

OTHER PUBLICATIONS

Luo, Jun-Li, et al. Oncogene 20.3 (2001): 320-328 (Year: 2001).*
Ramchandani, V.A., et al. Molecular psychiatry 16.8 (2011): 809-817 (Year: 2011).*
Kostenuik, PJ., et al. Journal of bone and mineral research 24.2 (2009): 182-195 (Year: 2009).*
Bochner, R, et al. Human molecular genetics 22.14 (2013): 2785-2794 (Year: 2013).*
Acosta, S, et al. Genesis 56.5 (2018): e23212 (Year: 2018).*
Parker A., LLNL S&TR. Dec. 2009: 14-17 (Year: 2009).*
Wilson BD, et al. Feb. 1995;4(2):223-30 (Year: 1995).*
Cui JY, et al. Drug Metab Dispos. Jun. 2012;40(6):1226-37 (Year: 2012).*
Peng, Rongxue, et al. The FEBS journal 283.7 (2016): 1218-1231 (Year: 2016).*
Gordon et al., "Genetic transformation of mouse embryos by microinjection of purified DNA", Proc. Natl. Acad. Sci. USA, vol. 77, No. 12, Dec. 1980, pp. 7380-7384.
International Search Report (PCT/ISA/210) issued in PCT/JP2019/021894, dated Aug. 27, 2019.
Khillan et al., "Transgenic Mice That Express a Mini-gene Version of the Human Gene for Type I Procollagen (COL1A1) Develop a Phenotype Resembling a Lethal Form of Osteogenesis Imperfecta", The Journal of Biological Chemistry, vol. 266, No. 34, Dec. 5, 1991, pp. 23373-23379.
Lewis et al., "Disruption of the developmentally-regulated col2a1 pre-mRNA alternative splicing switch in a transgenic knock-in mouse model", Matrix Biol., vol. 31, No. 3, Apr. 2012, pp. 1-26.
Liu et al., "Rescue of retinal morphology and function in a humanized mouse at the mouse retinol-binding protein locus", Laboratory Investigation, vol. 97, 2017, pp. 395-408.
Nagata et al., "A 6-kb Upstream Region of the Human Transthyretin Gene Can Direct Developmental, Tissue-Specific, and Quantitatively Normal Expression in Transgenic Mouse", J. Biochem., vol. 117, No. 1, 1995, pp. 169-175.
Nielsen et al., "Human Apolipoprotein B Transgenic Mice Generated with 207- and 145-Kilobase Pair Bacterial Artificial Chromosomes", The Journal of Biological Chemistry, vol. 272, No. 47, Nov. 21, 1997, pp. 29752-29758.
Schwartzberg et al., "Germ-Line Transmission of a c-abl Mutation Produced by Targeted Gene Disruption in ES Cells", Science, vol. 246, 1989, pp. 799-803.
Written Opinion of the International Searching Authority (PCT/ISA/237) issued in PCT/JP2019/021894, dated Aug. 27, 2019.

(Continued)

*Primary Examiner* — Marcia S Noble
*Assistant Examiner* — Zanna Maria Beharry
(74) *Attorney, Agent, or Firm* — Birch, Stewart, Kolasch & Birch, LLP

(57) ABSTRACT

Provided are a donor vector having an exon-humanized gene in which only exon nucleotide sequences of a mouse gene are replaced with human exon nucleotide sequences, an ES cell in which a mouse endogenous gene is replaced with the donor vector, and a mouse crated by using the ES cell.

6 Claims, 23 Drawing Sheets

Specification includes a Sequence Listing.

(56)                    References Cited

OTHER PUBLICATIONS

Zhao et al., "Inconsistency between hepatic expression and serum concentration of transthyretin in mice humanized at the transthyretin locus", Genes to Cells, vol. 13, 2008, pp. 1257-1268.
Zijlstra et al., "Germ-line transmission of a disrupted β2-microglobulin gene produced by homologous recombination in embryonic stem cells", Letters to Nature, vol. 342, Nov. 23, 1989, pp. 435-438.
Acosta et al., "Use of two gRNAs for CRISPR/Cas9 improves bi-allelic homologous recombination efficiency in mouse embryonic stem cells," Genesis, vol. 56, 2018, pp. 1-8.
Extended European Search Report for European Application No. 19930443.7, dated Dec. 22, 2022.
Japanese Decision of Refusal for Japanese Application No. 2021-522610, dated Feb. 28, 2023, with an English translation.
Morgan et al., "Excised linear introns regulate growth in yeast," Nature, vol. 565, 2019, pp. 606-611.

Parenteau et al., "Introns are mediators of cell response to starvation," Nature, vol. 565, 2019, pp. 612-617.
Seib et al., "Presence of regulatory sequences within intron 4 of human and murine c-myb genes," Biochimica et Biophysica Acta, vol. 1219, 1994, pp. 285-292.
Zhu et al., "Humanising the mouse genome piece by piece," Nature Communications, vol. 10, 2019, pp. 1-13.
European Communication pursuant to Article 94(3) EPC for European Application No. 19 930 443.7, dated Nov. 9, 2023.
Shaul, "How introns enhance gene expression," International Journal of Biochemistry and Cell Biology, vol. 91, Jun. 30, 2017, pp. 145-155.
Chinese Office Action and Search Report for Chinese Application No. 201980096550.9, dated Mar. 2, 2024, with English translation.
Miao, "Medical Cell Biology," Shanghai: Second Military Medical University Press, Jul. 31, 2015, pp. 180-181 (6 pages total).
Chinese Office Action and Search Report for Chinese Application No. 201980096550.9, dated Apr. 29, 2023, with an English translation.

* cited by examiner

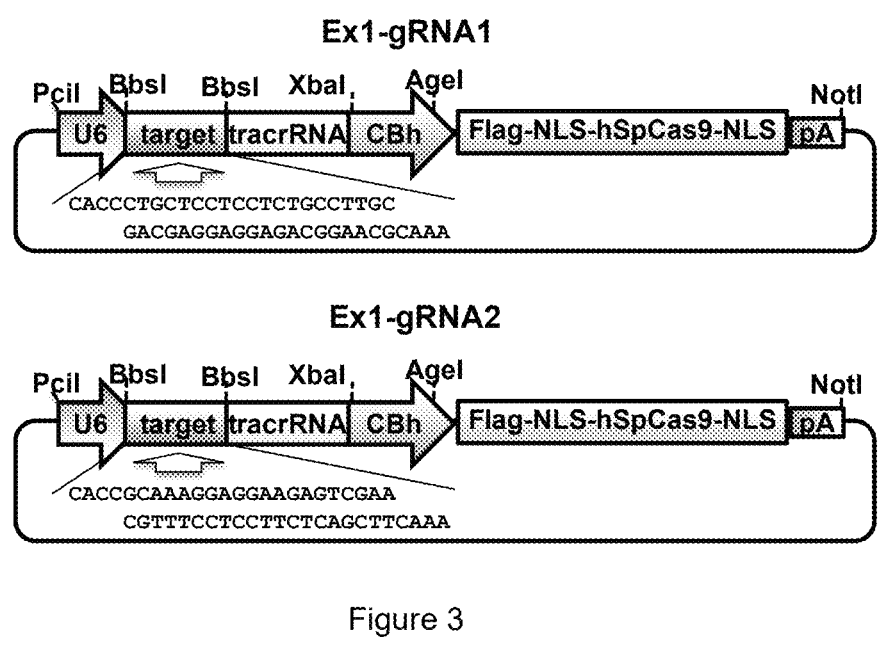

Ex1-gRNA1

CACCCTGCTCCTCCTCTGCCTTGC
GACGAGGAGGAGACGGAACGCAAA

Ex1-gRNA2

CACCGCAAAGGAGGAAGAGTCGAA
CGTTTCCTCCTTCTCAGCTTCAAA

Figure 3

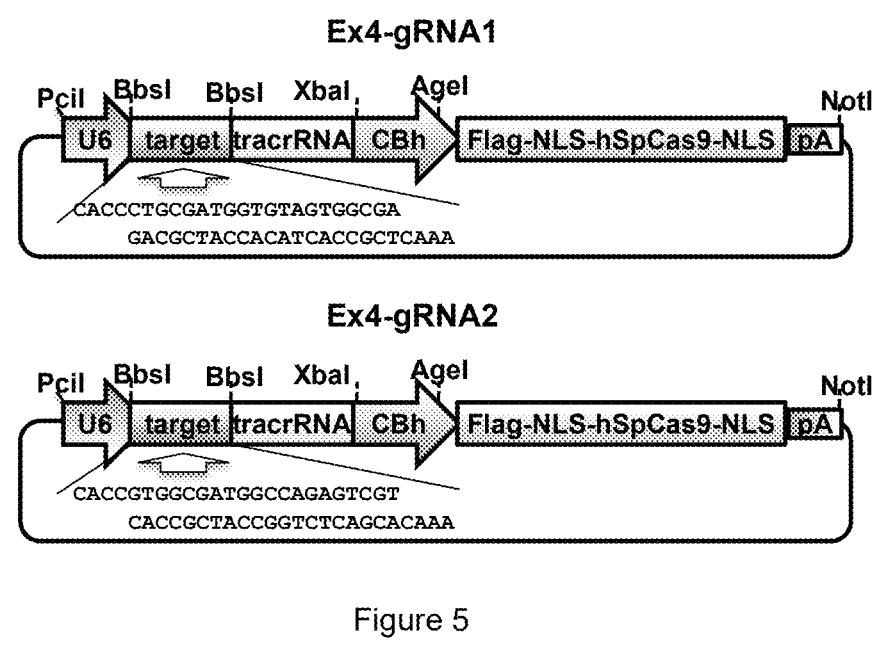

Ex4-gRNA1

```
CACCCTGCGATGGTGTAGTGGCGA
GACGCTACCACATCACCGCTCAAA
```

Ex4-gRNA2

```
CACCGTGGCGATGGCCAGAGTCGT
CACCGCTACCGGTCTCAGCACAAA
```

Figure 5

Positive control: a6221 ES genomic DNA
Negative control : Wild type mouse genomic DNA

```
Mouse      :  AAGCTCCTGACAGGATGGCTTCCCTTCGACTCTTCCTCCTTTGCCTCGCTGGACTGGTATTTGTGTCTGAAGCTGGCCCCGCGGTGAGTGATCCTGT
Humanized  :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-1       :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
F1-3       :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
F1-5       :  AAGCTCCTGACAGGATGGCTTCTCATCGTCTGCTCCTCCTCTGCCTTGCTGGACTGGTATTTGTGTCTGAGGCTGGCGCTACGGTGAGTGATCCTGT
F1-6       :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
F1-7       :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
F1-8       :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-9       :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
F1-12      :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-14      :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-15      :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
F1-19      :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-20      :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-25      :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
F1-28      :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-30      :  AAGCTCCTGACAGGATGGCTTCTCATCGTCTGCTCCTCCTCTGCCTTGCTGGACTGGTATTTGTGTCTGAGGCTGGCCCTACGGTGAGTGATCCTGT
F1-33      :  AAGCTCCTGACAGGATGGCTTCTCATCGTCTGCTCCTCCTCTGCCTTGCTGGACTGGTATTTGTGTCTGACGCTGGCCCTACGGTGAGTGATCCTGT
```

Sequences in red: Humanized sequences

Figure 10

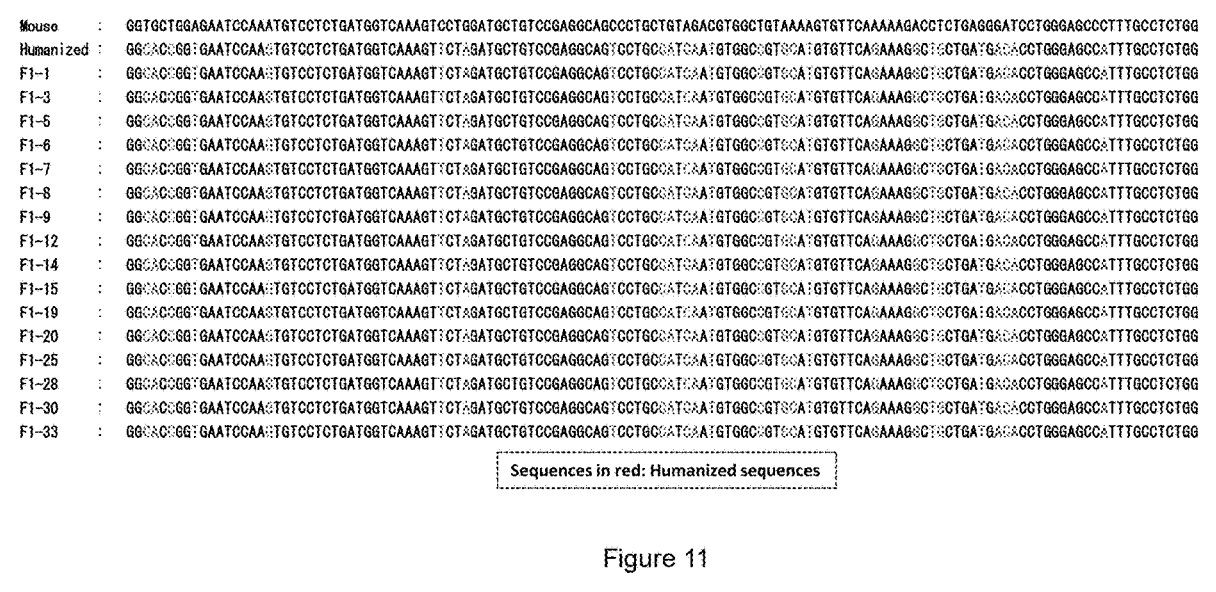

```
Mouse      :  GGTGCTGGAGAATCCAAATGTCCTCTGATGGTCAAAGTCCTGGATGCTGTCCGAGGCAGCCCTGCTGTAGACGTGGCTGTAAAAGTGTTCAAAAAGACCTCTGAGGGATCCTGGGAGCCCTTTGCCTCTGG
Humanized  :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-1       :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-3       :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGCTGCTGATGATCACCTGGGAGCCATTTGCCTCTGG
F1-5       :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-6       :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-7       :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-8       :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-9       :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-12      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-14      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-15      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-19      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-20      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-25      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-28      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-30      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
F1-33      :  GGCACGGGTGAATCCAACTGTCCTCTGATGGTCAAAGTCCTAGATGCTGTCCGAGGCAGTCCTGCCATCAATGTGGCGGTGCATGTGTTCAGAAAGGCTGCTGATGATCACCTGGGAGCCATTTGCCTCTGG
```

Sequences in red: Humanized sequences

Figure 11

```
Mouse     : AAGACCGCGGAGTCTGGAGAGCTGCACGGGCTCACCACAGATGAGAAGTTTGTAGAAGGAGTGTACAGAGTAGAACTGGACACCAAATCGTACTGGAAGACACTTGGCATTTCCCCGTTCCATGAATTCGCGGAT
Humanized : AAAACCXGGAGTCTGGAGAGCTGCAGGGCTCACAACGGAGGAGAATTTGTAGAAGGGATATACAAAGTGGAAATAGACACCAAATCGTACTGGAAGGCACTTGGCATGTCCCCATTCCATGAGCATGCAGAG
F1-1      : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-3      : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-5      : AAAACCXGGAGTCTGGAGAGCTGCAGGGCTCACAACGGAGGAGAATTTGTAGAAGGGATATACAAAGTGGAAATAGACACCAAATCGTACTGGAAGGCACTTGGCATGTCCCCATTCCATGAGCATGCAGAG
F1-6      : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-7      : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-8      : AAAACCXGGAGTCTGGAGAGCTGCAGGGCTCACAACGGAGGAGAATTTGTAGAAGGGATATACAAAGTGGAAATAGACACCAAATCGTACTGGAAGGCACTTGGCATGTCCCCATTCCATGAGCATGCAGAG
F1-9      : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-12     : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-14     : AAAACCXGGAGTCTGGAGAGCTGCAGGGCTCACAACGGAGGAGAATTTGTAGAAGGGATATACAAAGTGGAAATAGACACCAAATCGTACTGGAAGGCACTTGGCATGTCCCCATTCCATGAGCATGCAGAG
F1-15     : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-19     : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-20     : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-25     : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-28     : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
F1-30     : AAAACCXGGAGTCTGGAGAGCTGCAGGGCTCACAACGGAGGAGAATTTGTAGAAGGGATATACAAAGTGGAAATAGACACCAAATCGTACTGGAAGGCACTTGGCATGTCCCCATTCCATGAGCATGCAGAG
F1-33     : AAAACCXGGAGTCTGGAGAGCTGCAGGGCTCACAACGGAGGAGGAATTTGTAGAAGGGATATACAAAGTGGAAATAGACACCAAATCGTACTGGAAGGCACTTGGCATGTCCCCATTCCATGAGCATGCAGAG
```

Sequences in red: Humanized sequences

Figure 13

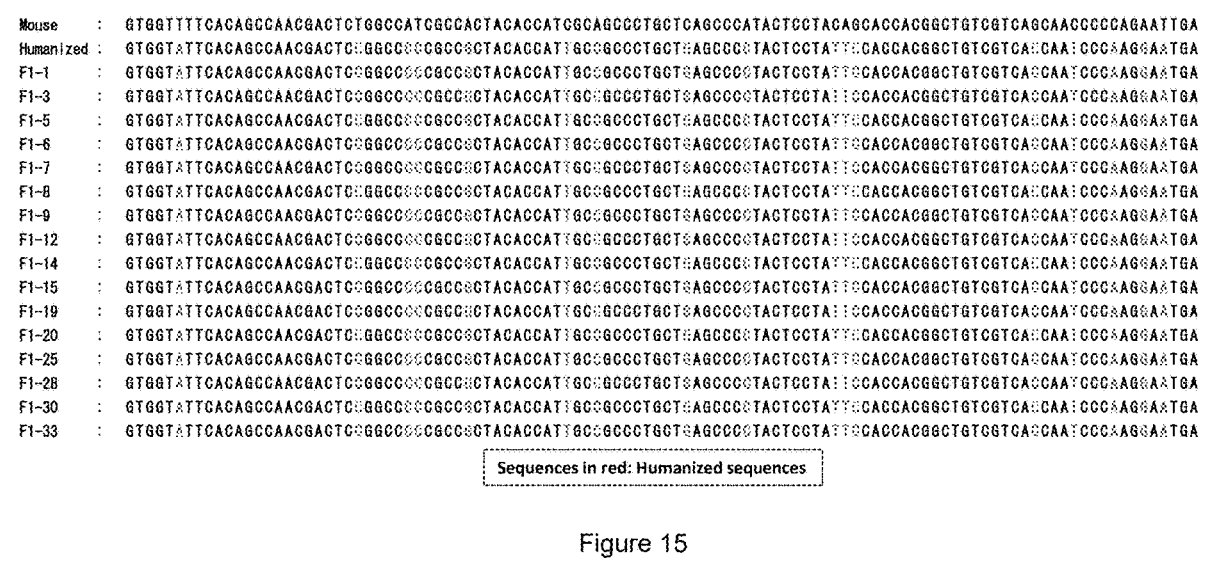

```
Mouse      : GTGGTTTTCACAGCCAACGACTCTGGCCATCGGCACTACACCATCGGCAGCCCTGCTCAGCCCATACTCCTACAGCACCACGGCTGTCGTCAGCAACGCCCAGAATTGA
Humanized  : GTGGTATTCACAGCCAACGACTC GGCC  CGCC CTACACCAT GC GCCCTGCT AGCCC TACTCCTA   CAGCACGGCTGTCGTCA CAA CCC AG  A TGA
F1-1       : GTGGTATTCACAGCCAACGAGTC GGCC  CGCC CTACACCAT GC GCCCTGCT AGCCC TACTCCTA   CACCACGGCTGTCGTCA CAA CCC AG  A TGA
F1-3       : GTGGTATTCACAGCCAACGACTC GGCC  CGCC CTACACCAT GC GCCCTGCT AGCCC TACTCCTA   CCACCACGGCTGTCGTCA CAA CCC AG  A TGA
F1-5       : GTGGTATTCACAGCCAACGACTC GGCC  CGCC CTACACCAT GC GCCCTGCT AGCCC TACTCCTA   CACCACGGCTGTCGTCA CAA CCC AG  A TGA
F1-6       : GTGGTATTCACAGCCAACGAGTC GGCC  CGCC CTACACCAT GC GCCCTGCT AGCCC TACTCCTA   CACCACGGCTGTCGTCA CAA CCC AG  A TGA
F1-7       : GTGGTATTCACAGCCAACGACTC GGGCC CGCC CTACACCAT GC GCCCTGCT AGCCC TACTCCTA   CACCACGGCTGTCGTCA CAA CCC AG  A TGA
F1-8       : GTGGTATTCACAGCCAACGACTC GGCC  CGCC CTACACCAT GC GCCCTGCT AGCCC TACTCCTA   CACCACGGCTGTCGTCA CAA CCC AG  A TGA
F1-9       : GTGGTATTCACAGCCAACGAGTC GGCC  CGCC CTACACCAT GC GCCCTGCT AGCCC TACTCCTA   CCACCACGGCTGTCGTCA CAA CCC AG  A TGA
F1-12      : GTGGTATTCACAGCCAACGAGTC GGCC  CGCC CTACACCAT GC GCCCTGCT AGCCC TACTCCTA   CCACCACGGCTGTCGTCA CAA CCC AG  A TGA
F1-14      : GTGGTATTCACAGCCAACGACTC GGCC  CGCC CTACACCAT GC GCCCTGCT AGCCC TACTCCTA   CACCACGGCTGTCGTCA CAA CCC AG  A TGA
F1-15      : GTGGTATTCACAGCCAACGAGTC GGCC  CGCC CTACACCAT GC GCCCTGCT AGCCC TACTCCTA   CCACCACGGCTGTCGTCA CAA CCC AG  A TGA
F1-19      : GTGGTATTCACAGCCAACGAGTC GGCC  CGCC CTACACCAT GC GCCCTGCT AGCCC TACTCCTA   CCACCACGGCTGTCGTCA CAA CCC AG  A TGA
F1-20      : GTGGTATTCACAGCCAACGACTC GGCC  CGCC CTACACCAT GC GCCCTGCT AGCCC TACTCCTA   CCACCACGGCTGTCGTCA CAA CCC AG  A TGA
F1-25      : GTGGTATTCACAGCCAACGACTC GGCC  CGCC CTACACCAT GC GCCCTGCT AGCCC TACTCCTA   CCACCACGGCTGTCGTCA CAA CCC AG  A TGA
F1-28      : GTGGTATTCACAGCCAACGAGTC GGCC  CGCC CTACACCAT GC GCCCTGCT AGCCC TACTCCTA   CCACCACGGCTGTCGTCA CAA CCC AG  A TGA
F1-30      : GTGGTATTCACAGCCAACGACTC GGCC  CGCC CTACACCAT GC GCCCTGCT AGCCC TACTCCTA   CACCACGGCTGTCGTCA CAA CCC AG  A TGA
F1-33      : GTGGTATTCACAGCCAACGAGTC GGCC  CGCC CTACACCAT GC GCCCTGCT AGCCC TACTCCTA   CCACCACGGCTGTCGTCA CAA CCC AG  A TGA
```

Sequences in red: Humanized sequences

Figure 15

Sequence around GTG encoding amino acid 30 of hTTR

GGCACCGGTGAATCCAAGTGTCCTCTGATGGTCAAAGTTCTAGATGCTGTCC

Sequences for crRNA (or sgRNA) synthesis

Target sequence: TGAATCCAAGTGTCCTCTGATGG

5'-TGAATCCAAGTGTCCTCTGAGUUUUAGAGCUAUGCUGUUUUG-3'

Sequence of tracrRNA

5'-AAACAGCAUAGCAAGUUAAAAUAAGGCUAGUCCGUUAUCAACUUGAAAAAGUGGCA
CCGAGUCGGUGCU-3'

Sequence of ssDNA (containing ATG and its flanking sequences of 60 bp for conversion of GTG into ATG)

tgacccatttcactgacatttctcttgtctcctctgtgcccagGGCACCGGTGAATCCAAAGTCCTCTGA
TGGTCAAAGTTCTAGATGCTGTCCGAGGCAGTCCTGCCATCAATGTGGCCGT

Figure 21

Target sequence
CTCATTCTTGGCAGGA(TGG)
(TGG at the right end serves as a PAM sequence, and the underlined part is ATG)

CACCCTCATTCTTGGCAGGA
GAGTAAGAACCGTCCTCAAA

Target sequence
TGAATCCAAATGTCCTCTGA TGG
(ATG in the center encodes methionine, and TGG
at the right end serves as a PAM sequence.)

CACCTGAATCCAAATGTCCTCTGA
AGGTGAGTAAGAACCGTCCTCAAA

EXON-HUMANIZED MOUSE

REFERENCE TO SEQUENCE LISTING SUBMITTED VIA EFS-WEB

This application includes an electronically submitted sequence listing in .txt format. The .txt file contains a sequence listing entitled "4456-0285PUS1_ST25.txt" created on May 15, 2022 and is 53,715 bytes in size. The sequence listing contained in this .txt file is part of the specification and is hereby incorporated by reference herein in its entirety.

TECHNICAL FIELD

The present invention relates to a vector having a mouse gene whose introns remain of mouse origin and only whose exons are replaced with human nucleotide sequences, and also relates to an embryonic stem cell (hereinafter referred to as "ES cell") having such an exon-humanized gene, and an exon-humanized mouse established using the same.

BACKGROUND ART

In 1980, Gordon et al. produced transgenic mice by injecting isolated foreign genes into fertilized eggs (Gordon et al. Proc. Natl. Acad. Sci. USA. 77:7380-7384, 1980). Since then, to introduce and express a human gene in mice, efforts have been made to inject an isolated human gene as a genomic gene (Nagata et al. J. Biochem. 117:169-175, 1995, by way of example), a minigene (Khiallan et al. J. Biol. Chem. 266:23373-23379, 1991, by way of example) or an artificial bacterial chromosome (Nieelsen et al. J. Biol. Chem. 272:29752-29758, 1997, by way of example), etc., into mouse fertilized eggs to thereby produce transgenic mice, and there have been many cases actually carried out.

In 1989, techniques were developed to allow targeted disruption at a certain gene by homologous recombination using mouse ES cells (Zijlstra et al. Nature 342:435-438, 1989; Schwartzberg et al. Science 246:799-803, 1989). In some known techniques, this homologous recombination is used to knock-in a human gene as cDNA (Zhao et al. Gene Cells 13:1257-1268, 2008; Liu et al. Lab. Invest. 97:395-408, 2017) or a minigene (Lewis et al. Matrix Biol 31:214-226, 2012), etc., into a mouse gene locus to cause the expression of the human gene. However, these techniques have many drawbacks in that the expression level of an introduced human gene is not always normal, i.e., may be a higher or lower level, and that the tissue specificity of expression also varies from case to case, etc.

In light of the foregoing, transgenic mice produced by the above techniques can be used, for example, as human disease models in pathological analyses. However, for use in the development of therapies and the verification of their effectiveness, the transgenic mice are required to show normal expression levels and expression patterns. Thus, in this respect, there is a limit to their use as models.

PRIOR ART DOCUMENTS

Non-Patent Documents

Non-patent Document 1: Gordon et al. Proc. Natl. Acad. Sci. USA. 77:7380-7384, 1980
Non-patent Document 2: Nagata et al. J. Biochem. 117:169-1175, 1995
Non-patent Document 3: Khillan et al. J. Biol. Chem. 266:23373-23379, 1991
Non-patent Document 4: Nielsen et al. J. Biol. Chem. 272:29752-29758, 1997
Non-patent Document 5: Zijlstra et al. Nature 342:435-438, 1989
Non-patent Document 6: Schwartzberg et al. Science 246:799-803, 1989
Non-patent Document 7: Zhao et al. Gene Cells 13:1257-1268, 2008
Non-patent Document 8: Liu et al. Lab. Invest. 97:395-408, 2017
Non-patent Document 9: Lewis et al. Matrix Biol 31:214-226, 2012

SUMMARY OF THE INVENTION

Problem to be Solved by the Invention

The present invention aims to provide a mouse in which only exons in a mouse gene are humanized. More specifically, to obtain a normal expression pattern in terms of the level and tissue specificity of gene expression, the present invention aims to provide an exon-humanized mouse carrying a gene whose introns still have mouse nucleotide sequences and only whose exons have human nucleotide sequences.

Means to Solve the Problem

To solve the problems described above, the inventors of the present invention have used the transthyretin (TTR) gene as a representative example and have made extensive and intensive efforts. As a result, the inventors of the present invention have prepared mouse ES cells having a mouse Ttr gene whose introns still have mouse nucleotide sequences and only whose exon segments are replaced with human nucleotide sequences, followed by chimeric mouse production to thereby successfully create a mouse in which only exons in the Ttr gene are humanized.

When analyzing the exon-humanized Ttr gene in this mouse for the tissue specificity of its expression, the inventors of the present invention have found that the exon-humanized Ttr gene shows the same expression pattern as the mouse Ttr gene and also ensures the same blood TTR level as the level of mouse TTR in wild-type mice. These findings led to the completion of the present invention.

Specifically, the present invention provides the followings:

(1) A donor vector comprising a fragment comprising n exons of a target gene, wherein the target gene is contained in the mouse genome and comprises the n exons, and wherein the n exons are replaced respectively with exons of the corresponding human target gene.

(2) The donor vector according to (1), wherein the target gene is the transthyretin gene.

(3) A vector expressing a guide RNA for cleaving genome at a site immediately upstream of the first exon, wherein the vector comprises a target sequence for cleavage, tracrRNA, and DNA encoding a DNA-cleaving enzyme.

(4) A vector expressing a guide RNA for cleaving genome at a site immediately downstream of the $n^{th}$ exon, wherein the vector comprises a target sequence for cleavage, tracrRNA, and DNA encoding a DNA-cleaving enzyme.

(5) An exon-humanized ES cell comprising intron segments having nucleotide sequences of the mouse gene and exon segments having nucleotide sequences replaced with nucleotide sequences of the human gene, obtained by introducing the donor vector according to (1) or (2) and the vectors according to (3) and (4) into an ES cell.

(6) A exon-humanized mouse created by using the ES cell according to (5).

(7) A method for producing an exon-humanized mouse comprising exons in the mouse gene replaced with exons in the human gene, which comprises the followings:

(a) introducing the donor vector according to (1) or (2) and the vectors according to (3) and (4) into ES cells;

(b) creating chimeric embryos from the ES cells obtained in the step (a) and transplanting the chimeric embryos into foster mothers to thereby create chimeric mice; and (c) selecting a male mouse and a female mouse from among the chimeric mice obtained in the step (b) and crossing them to produce pups.

(8) A method for producing a disease model mouse, comprising introducing a disease-related gene mutation into an exon in the exon-humanized mouse according to (6).

(9) A laboratory animal for gene therapy, which includes the exon-humanized mouse according to (6) or the disease model mouse produced by the method according to (8).

Effects of the Invention

The present invention provides ES cells having a gene comprising intron segments having nucleotide sequences of a mouse gene and exon segments having nucleotide sequences replaced with nucleotide sequences of a human gene. The ES cells of the present invention enable the establishment of an exon-humanized mouse expressing the human TTR protein at its normal level and with its normal tissue specificity. The exon-humanized mouse of the present invention shows an expression pattern which is normal in terms of not only expression level but also tissue specificity, and is therefore very useful in producing human disease model mice and in examining the efficacy of drugs and gene therapies.

BRIEF DESCRIPTION OF THE DRAWINGS

FIG. 3 is a diagram of ExT-gRNAs.

FIG. 5 is a diagram of Ex4-gRNAs.

FIG. 10 is a diagram showing the nucleotide sequence of exon 1.

FIG. 11 is a diagram showing the nucleotide sequence of exon 2.

FIG. 13 is a diagram showing the nucleotide sequence of exon 3.

FIG. 15 is a diagram showing the nucleotide sequence of exon 4.

FIG. 21 is a diagram showing the nucleotide sequences of crRNA, tracrRNA and donor oligo.

DESCRIPTION OF EMBODIMENTS

The present invention will be described in more detail below.

1. Summary

The present relates to ES cells having a gene comprising intron segments having mouse nucleotide sequences and exon segments having nucleotide sequences replaced with human nucleotide sequences, and also establishment of a mouse in which a human protein shows its normal expression pattern, starting from such ES cells.

In general, in transgenic mice carrying a human gene, the human gene injected into a fertilized egg is integrated at a random site on the chromosome, so that gene expression varies among individual mice, and it is rare to show a normal expression pattern. Moreover, even when cDNA or a mini-gene is inserted into a mouse gene, such insertion results in a change in the genome structure, and it is rare to show a normal expression pattern.

Thus, in the present invention, a mouse in which only exons are humanized is established for establishment of a mouse in which a human protein shows its normal expression pattern. To establish this exon-humanized mouse, the inventors of the present invention have constructed a donor vector comprising a gene whose introns have mouse nucleotide sequences and whose exons have human nucleotide sequences, and have succeeded in establishing ES cells in which original mouse gene locus is replaced with the donor vector. The inventors of the present invention have also succeeded in producing a chimeric mouse using the ES cells to thereby prepare a germ-line chimeric mouse for germ-line transmission.

The mouse of the present invention is a mouse in which only exons in a mouse target gene are replaced with human exons.

In a preferred embodiment of the present invention, the mouse of the present invention is a mouse which does not express a mouse protein and expresses only a human protein. In this embodiment, only introns have mouse nucleotide sequences; and hence the sequences involved in expression regulation remain of mouse origin, and mouse transcription factors and others normally bind and function. As a result, a normal expression level and a normal tissue-specific expression pattern can be obtained.

2. Preparation of Donor Vector

In the production of the mouse of the present invention, normal ES cells are first transfected by electroporation with guide RNAs prepared based on the CRISPR/Cas9 system and a donor vector having mouse nucleotide sequences for introns and having human nucleotide sequences for exons to cause homologous recombination, whereby a mouse endogenous gene is replaced with the donor vector to thereby create ES cells in which exons in the mouse genome are replaced with human exons.

In the present invention, the donor vector comprises a fragment comprising n exons of a target gene, wherein the target gene is contained in the mouse genome and comprises the n exons, and wherein the n exons are replaced respectively with exons of the corresponding human target gene. n represents the number of exons contained in the genome.

Figure 1:
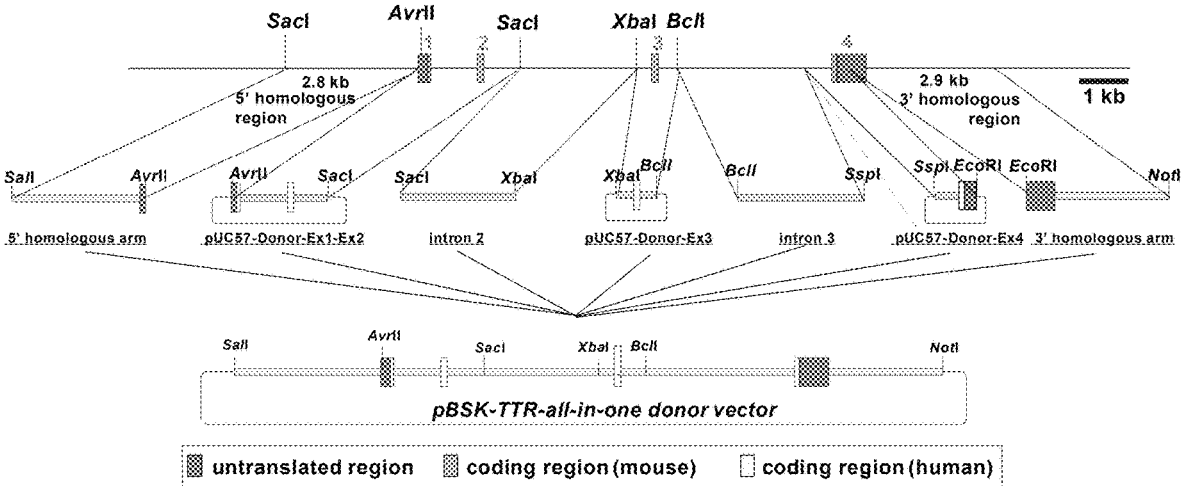
FIG. 1 is a schematic diagram showing donor vector preparation.

The upper panel of FIG. 1 shows a genome map comprising exons to be humanized and introns not to be humanized on the genome. FIG. 1 illustrates exons of the transthyretin gene, and the number of exons is 4 (n=4) (the boxes indicated with numbers 1 to 4 in FIG. 1). The present invention will be described below by taking this transthyretin gene as an example. It should be noted that the mouse transthyretin gene is expressed as the "Ttr gene" while the human transthyretin gene is expressed as the "TTR gene."

There are several methods to prepare a gene only whose exons have human nucleotide sequences and whose introns have mouse nucleotide sequences.

For example, human exons and mouse introns are cloned separately and then joined together in the final step. However, restriction enzyme sites required for joining do not always match, which makes the operations difficult.

A highly efficient method includes a method comprising synthesizing human exons and their upstream and downstream mouse intron segments all together as DNA, and this DNA is inserted into a vector, as shown in FIG. 1. Namely, in FIG. 1, the regions labeled "pUC57-Donor-Ex1-Ex2," "pUC57-Donor-Ex3" and "pUC57-Donor-Ex4" are synthesized as DNA, and the other regions (intron regions) are cloned. According to this method, restriction enzyme sites required for joining may be selected freely. These intron segments may be easily cloned from the mouse genome in a well-known manner. In the final step, these DNA fragments may be joined together.

Among genes of large size, some have a number of exons difficult to insert into a single vector. In such a case, exons may be divided and prepared in several donor vectors, but not a single donor vector. Namely, n exons in total may be divided into k subclasses ($n_1$, $n_2$, ... $n_k$) (where k represents the number of donor vectors), and a donor vector may be prepared for each subclass of exons in the same manner as described above. For example, if there are 10 exons (n=10), these exons are divided into, for example, three subclasses (k=3), 4 exons ($n_1$=4), 3 exons ($n_2$=3) and 3 exons ($n_3$=3), and a donor vector is prepared for each of these three subclasses.

3. Preparation of Guide RNAs

Expression vectors for the guide RNAs of the present invention are a vector expressing a guide RNA for cleaving genome at a site immediately upstream of the first exon and a vector expressing a guide RNA for cleaving genome at a site immediately downstream of the $n^{th}$ exon (the fourth exon in the case of the mouse Ttr gene), and these vectors each comprise a target sequence for cleavage, tracrRNA, and DNA encoding a DNA-cleaving enzyme. The phrase "immediately upstream" is intended to mean a site located 1 to 20 nucleotides upstream from the 5'-end of the first exon, while the phrase "immediately downstream" is intended to mean a site located 1 to 20 nucleotides downstream from the 3'-end of the $n^{th}$ exon. If n exons are divided into $n_1$, $n_2$, ... and $n_k$ subclasses, the above phrases are also defined as in the case where exons are not divided into subclasses. For example, in the respective subclasses, the phrases are defined to be a site located 1 to 20 nucleotides upstream from the 5'-end of the first exon and a site located 1 to 20 nucleotides downstream from the 3'-end of the $n_1^{th}$, $n_2^{th}$, ... or $n_k^{th}$ exon.

The CRISPR/Cas9 system is a defense mechanism used by bacteria and others to selectively disrupt the DNA of invading viruses and plasmids. For development of this mechanism, crRNA and tracrRNA and also a molecule called Cas9 that has DNA double-strand cleavage activity are required in principle. crRNA comprises a sequence complementarily binding to viral DNA, etc., and binds to tracrRNA via another portion. tracrRNA has been bound to Cas9 and eventually guides Cas9 to the viral DNA site bound with crRNA. Then, Cas9 claves the viral DNA at this site to thereby cause virus disruption (Jinek et al. Science 337:816-821, 2012). It has been indicated that once these three elements are expressed, DNA can be cleaved at a particular sequence site even in mammalian cells, i.e., gene can be disrupted even in mammalian cells (Ran et al. Nat Protoc. 8:2281-2308, 2013). Furthermore, vectors (e.g., pX330) have been developed such that these three elements can be expressed by a single vector (Sakuma et al. Sci. Rep. 4:5400, 2014).

Some home pages that allow one to search for which nucleotide sequence in a gene can be most easily disrupted are also open to the public. At present, for example, when CCTop-CRISPR/Cas9 target online predictor (https://crispr.cos.uni-heidelberg.de) is used to search for nucleotide sequences near a site targeted to be disrupted, candidate sequences of 20 bp are shown, along with sites where similar sequences are located, i.e., so-called off-target sites. From among them, about 3 sequences are selected in order of precedence and each integrated into pX330, and the efficiency of double-stranded DNA cleavage can be examined using cultured cells (Mashiko et al. Sci. Report 3:3355, 2013).

4. Isolation of Knock-In ES Cells

For establishment of an exon-humanized mouse, it is necessary to replace an endogenous gene with an exon-humanized gene at the ES cell stage but not in an adult mouse.

In the present invention, to replace an endogenous gene present in ES cells with an exon-humanized gene, conventional homologous recombination techniques or the CRISPR/Cas9 system can be used. In the CRISPR/Cas9 system, a specific nucleotide sequence can be specifically cleaved, allowing to efficiently create a knock-out mouse (Wang et al. Cell 153:910-918, 2013). In this case, it is shown that the DNA repair system is induced in cells, and homologous recombination also occurs with high probability, so that knock-in is also possible (Yang et al. Cell 154:1370-1379, 2013).

Examples of culture medium for ES cells include GMEM medium (Glasgow's Minimal Essential Medium), DMEM medium (Dulbecco's modified Eagle's medium), RPMI 1640 medium and so on. The culture medium may be supplemented as appropriate with an additional ingredient(s) selected from KSR (Knockout Serum Replacement), fetal bovine serum (FBS), basic fibroblast growth factor (bFGF), β-mercaptoethanol, nonessential amino acids, glutamic acid, sodium pyruvate and antibiotics (e.g., penicillin, streptomycin), etc.

ES cells are cultured for a given period of time and then incubated in a medium containing EDTA or collagenase IV to thereby collect the ES cells. The thus collected ES cells may optionally be subcultured for several passages in the presence or absence of feeder cells. It should be noted that inner cell mass culture under feeder-free conditions can be conducted in a MEF-conditioned medium.

The cultured ES cells may usually be identified using their marker genes. Examples of marker genes in ES cells include Oct3/4, alkaline phosphatase, Sox2, Nanog, GDF3, REX1, FGF4 and so on. The presence of marker genes or their gene products may be detected by any technique such as PCR or Western blotting, etc.

The replacement of a mouse gene with the above exon-humanized gene may be accomplished in accordance with the CRISPR/Cas9 system. First, the above donor vector and guide RNAs are introduced into the ES cells by electroporation.

When the donor vector and guide RNAs are introduced into ES cells, a specific sequence contained in each guide RNA binds to its complementary sequence on the genome, and Cas9-mediated double-strand cleavage of DNA occurs at this site. As a result, the so-called homology directed repair system is induced, and homologous recombination occurs between a mouse nucleotide sequence contained in the donor vector and its homologous sequence on the mouse genome, whereby an exon-humanized gene is inserted (FIG. 7).

According to these procedures, the endogenous mouse gene can be replaced with the exon-humanized gene. FIG. 7 shows the replaced allele.

Figure 7:
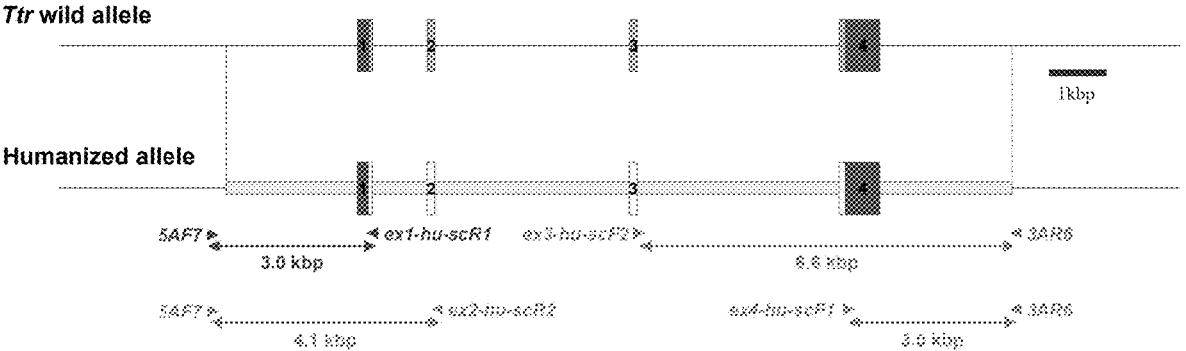
FIG. 7 is a diagram showing primers for gene determination.

In FIG. 7, numbers 1 to 4 appearing in "Ttr wild allele" represent exons 1 to 4 in the mouse transthyretin gene, while numbers 1 to 4 appearing in "Humanized allele" represent exons 1 to 4 in the human transthyretin gene.

Any genes other than the Ttr gene may also be replaced as in the above case of transthyretin. Namely, a gene is prepared to have human nucleotide sequences for exon segments and mouse nucleotide sequences for intron segments, and this gene and guide RNAs may be introduced into ES cells by the CRISPR/Cas9 system.

For example, in the case of producing a mouse in which only exons in the Rbp4 gene are humanized, an exon-humanized Rbp4$^{hRBP4exon}$ gene whose 4 exons have human nucleotide sequences and whose introns have mouse nucleotide sequences is prepared, and this gene is introduced together with guide RNAs into ES cells, whereby the Rbp4$^{hRP4exon}$ mouse can be produced.

5. Production of a Chimeric Mouse

Production of a chimeric mouse may be accomplished in a standard manner.

First, the above established ES cells are allowed to aggregate with an eight-cell embryo or are injected into a blastocyst. The thus prepared embryo is referred to as a chimeric embryo, and this chimeric embryo is transplanted into the uterus of a pseudopregnant foster mother, which is then allowed to give birth, thereby producing a chimeric mouse.

For example, to prepare a chimeric embryo, a female mouse treated with a hormone drug for superovulation may first be crossed with a male mouse. Then, after a given number of days have passed, an embryo at early development stage may be collected from the uterine tube or uterus. The collected embryo may be aggregated or injected with ES cells to prepare a chimeric embryo.

The term "embryo" as used herein is intended to mean an individual at any stage from fertilization to birth during ontogeny, including a two-cell embryo, a four-cell embryo, an eight-cell embryo, a morula stage embryo, a blastocyst and so on. An embryo at early development stage can be collected from the oviduct or uterus at 2.5 days after fertilization for use as an eight-cell embryo and at 3.5 days after fertilization for use as a blastocyst.

For preparation of an aggregate using ES cells and an embryo, known techniques such as the microinjection method, the aggregation method and so on can be used. The term "aggregate" is intended to mean an aggregate formed from ES cells and an embryo gathering together in the same space, and includes both cases where ES cells are injected into an embryo and where an embryo is dissociated into separate cells and aggregated with ES cells.

In the case of using the microinjection method, ES cells may be injected into the collected embryo to prepare a cell aggregate. Alternatively, in the case of using the aggregation method, ES cells may be aggregated by being sprinkled over a normal embryo whose zona pellucida has been removed.

On the other hand, a pseudopregnant female mouse for use as a foster mother can be obtained from a female mouse with normal sexual cycle by crossing with a male mouse vasectomized by ligation of deferent duct or other techniques. The thus created pseudopregnant mouse may be transplanted in the uterus with chimeric embryos prepared as described above and then allowed to give birth, thereby producing chimeric mice.

6. Production of Exon-Humanized Mouse

From among the thus produced chimeric mice, a male mouse derived from the ES cell-transplanted embryo is selected. After the selected male chimeric mouse has been matured, this mouse may be crossed with an inbred female mouse. Then, if the coat color of the ES cell-derived mouse appears in the born pups, it can be confirmed that the ES cells have been introduced into the germ line of the chimeric mouse.

Identification of whether the born pups have an exon-humanized gene and whether they have a normal sequence can be accomplished by determining whether a DNA fragment of desired size is detected upon cleavage of their DNA with restriction enzymes and by analyzing the nucleotide sequence of their DNA. When the born pups can be confirmed to have a normal sequence, an exon-humanized mouse in their subsequent generations may be identified by PCR analysis using human exon and mouse intron sequences as primers.

7. Evaluation of Exon-Humanized Mouse

Humanization of exons may be confirmed by measuring serum transthyretin by ELISA or Western blotting, as distinguished from mouse transthyretin. In cases where other genes are humanized, humanization of exons can also be confirmed by ELISA or Western blotting of the expressed proteins of these other genes.

8. Production of Mutated Exon-Humanized Mouse Using Exon-Humanized Mouse

There are many human hereditary diseases caused by a single genetic defect. For example, a point mutation in the TTR gene causes familial amyloid polyneuropathy, which is a dominant hereditary disease. When a fertilized egg of a mouse having wild-type human TTR exons (wild-type exon-humanized mouse) is injected with crRNA, tracrRNA, Cas9 and a donor oligo, GTG encoding valine at position 30 can be replaced with the sequence ATG (Yang et al. Cell 154:1370-1379, 2013). In this way, when human wild-type exon sequences are used to replace exons in a mouse gene to thereby produce a wild-type exon-humanized mouse, it is possible to produce a mouse having a mutated exon(s), i.e., a disease model mouse having the same mutated gene as human patients, by mutating the human exons possessed by this mouse.

9. Gene Therapy Experiment with Wild-Type Exon-Humanized Mouse and Mutated Exon-Humanized Mouse When crossing a wild-type exon-humanized mouse with a mutated exon-humanized mouse, a heterozygous mouse having both wild-type and mutant genes can be obtained. This mouse has the same genotype as human patients. This exon-humanized heterozygous mouse may be used for verification of therapies. In particular, this exon-humanized heterozygous mouse allows gene therapy experiments on hereditary diseases caused by defects in genes expressed in the liver which have received attention in recent years.

In conventional cases, mutations are caused in mouse genes and the resulting mice are used as models for therapy experiments (Yin et al. Nat Biotechnol. 32:551-553, 2014; Pankowicz et al. Nat Commun. 7:12642, 2016; Yang et al. Nat Biotechnol 34: 334-338, 2016; Yin et al. Nat Biotechnol. 34:328-333, 2016; Jarrett et al. Sci Rep. 7:44624, 2017; Villiger et al. Nat Med. 24:1519-1525, 2018). However, these models do not have the same nucleotide sequences as human genes, and when actually extrapolated to humans, therapy experiments with these models cannot always predict therapeutic effects precisely although they serve as references. In the exon-humanized mouse, its exons have the same sequences as human exons, and therapeutic effects can be predicted accurately, so that its usefulness is high.

The present invention will be further described in more detail by way of the following examples, although the present invention is not limited to these examples. It should be noted that these experiments and others were applied to and all approved by the animal research committee, and the safety committee on recombinant DNA experiments of class 2.

EXAMPLES

Example 1

Donor Vector

A donor vector comprising mouse sequences, whose coding regions of four exons are replaced with the corresponding human sequences, was prepared in the following manner (FIG. 1).

Since Exon 1 and Exon 2 are in proximity to each other, these exons were synthesized as a single donor DNA (pUC57-DonorEx1-Ex2). This donor DNA comprises a mouse nucleotide sequence covering from the AvrII site to the site immediately upstream of ATG, a human nucleotide sequence for exon 1 starting from ATG, a mouse nucleotide sequence for intron 1, a human nucleotide sequence for exon 2, and a mouse nucleotide sequence covering from the splice donor to the SacI site in intron 2. A donor DNA of Exon 3 (pUC57-Donor-Ex3) was synthesized to comprise a mouse nucleotide sequence covering from the XbaI site to the splice acceptor in mouse intron 2, a human nucleotide sequence for exon 3, and a mouse nucleotide sequence covering from the splice donor to BclI in intron 3. A donor DNA of Exon 4 (pUC57-Donorr-Ex4) was synthesized to comprise a mouse nucleotide sequence covering from the SspI site to the splice acceptor in intron 3, a human nucleotide sequence for exon 4, and a mouse nucleotide sequence covering from the site downstream of the termination codon to the EcoRI site in the 3' non-coding region. In addition to these, a 5' homologous arm (2.8 kb), intron 2 (3.4 kb), intron 3 (3.5 kb) and a 3' homologous arm (2.9 kb) were prepared such that the genomic DNA of the C57BL/6 ES cell line RENKA was used as a template to amplify these DNA fragments. The above seven DNA fragments were joined together to prepare the donor vector (pBSK-TTR-all-in-one donor vector) (SEQ ID NO: 1).

In the nucleotide sequence shown in SEQ ID NO: 1, the sequences constituting the donor vector (pBSK-TTR-all-in-one donor vector) are shown in Table 1 along with their SEQ ID NOs.

TABLE 1

| Nucleotide No. | Name and Sequence | SEQ ID NO |
|---|---|---|
| 1~679 | pBSK: CTAAATTGTAAGCGTTAATATTTTGT TAAAATTCGCGTTAAATTTTTGTTA AATCAGCTCATTTTTTAACCAATAG GCCGAAATCGGCAAAATCCCTTATA AATCAAAAGAATAGACCGAGATAGG GTTGAGTGTTGTTCCAGTTTGGAAC AAGAGTCCACTATTAAAGAACGTGG ACTCCAACGTCAAAGGGCGAAAAAC CGTCTATCAGGGCGATGGCCCACTA CGTGAACCATCACCCTAATCAAGTT TTTTGGGGTCGAGGTGCCGTAAAGC ACTAAATCGGAACCCTAAAGGGAGC CCCCGATTTAGAGCTTGACGGGGAA AGCCGGCGAACGTGGCGAGAAAGGA AGGGAAGAAAGCGAAAGGAGCGGGC GCTAGGGCGCTGGCAAGTGTAGCGG TCACGCTGCGCGTAACCACCACACC CGCCGCGCTTAATGCGCCGCTACAG GGCGCGTCCCATTCGCCATTCAGGC TGCGCAACTGTTGGGAAGGGCGATC GGTGCGGGCCTCTTCGCTATTACGC CAGCTGGCGAAAGGGGGATGTGCTG CAAGGCGATTAAGTTGGGTAACGCC AGGGTTTTCCCAGTCACGACGTTGT AAAACGACGGCCAGTGAGCGCGCGT AATACGACTCACTATAGGGCGAATT GGGTACCGGGCCCCCCCTCGAGGTC GAC | 2 |
| 680~3300 | 5' homologous arm: cctccaggtcttatccacctcaagg ggagctaacaaaattgaattctttg acctgcaaagattcagagccccaaa cactgctatttctcttctcctaact cccttaccaggaggcttagtgcaag catttggcccacctagtcccttcc tgctaatcagcttactgcactagca ttagcgagcattccagggcctacaa actgctggctaggtgtttgtttgga ccttcagaaaacaaatgaagagatt gtttaggagatgaaaagatgtattg aacgaggttgtacattttaagggag aaggccgagaagactctctaatcaa gagccagccagggttgttcattaac taccataaatttggtagtagggaga gagatgtggtcagtaactcaatctc tcattcacctaaatgaaacatgtaa gctatggcaccgcagccaggatgtg aagaaaaccagtaaagggctaagca aagacacctccttctaacttaaaca ctacctccaacacccttatgttctc taggtagttgctgttagtattaccc cagaacaggcaatgtcttcagcaga agccccacaaaggcggtgaattttg acacaagtccatccctcatcatgga ttcctgtaaccatcctctgagaaga gttttacaatttcaactcaatatg tgaaaccacaccttcctttctttag aaaagtatgattgattatccatggg acctattcacagcacaaagtgactc aaaggcaaaaagcacttgggcttct ctgggggcaactgccctttatctc acacccatgtcttggacaacaaatg ttttcttactctgtctgttttttct gtcctgctctgtcacataaaatcct gcccgacctttgactcaaactccag | 3 |

TABLE 1-continued

| Nucleotide No. | Name and Sequence | SEQ ID NO |
|---|---|---|
| | acagtctacctgctgatcgcccggc | |
| | ccctgttcaaacatgtcctaatact | |
| | ctgtctctgcaagggtcatcagtag | |
| | ttttccatcttactcaacatcctcc | |
| | cagtgcttcaaagcacctcacttta | |
| | tcttcacatccttgtctctttctaa | |
| | ttaaagtttaaaaagttggtttcta | |
| | aggctgatggaggtctaaaaaacaa | |
| | gcaaatcaaagacctgagggtgttc | |
| | taatttacttggtagttggtcagaa | |
| | ctaccagtatgttatggtcagagat | |
| | aaaattagggatactatacttagatc | |
| | aaaatttataaaaagacagagtaga | |
| | gaggatctctgtgagttcaaggtta | |
| | gcctggtcttcgtgcagcgagctcc | |
| | aggctagccaaaggtacaaaatgag | |
| | attctgtccctaaacagcaaaccaa | |
| | aaactaaataaaattgataaatgag | |
| | catagttcattatgatgaatgctct | |
| | ttacttgtgttagacacagggttgg | |
| | gtgaggcatcacagtgataacagtt | |
| | acagatgcacttagggtatgacact | |
| | gcctgcagagcacatttgtcaagga | |
| | agactaaagccttctggccatgtcc | |
| | tcagggtttacatgcaccttatctga | |
| | aatgtgtctccagttcaattatctg | |
| | gaatgtgtgtctgcttcagtgcctc | |
| | acattggtagagaaacattgaccag | |
| | tgggaggaagccagacaacaaagtc | |
| | ctgggaagagaggattccaggtcct | |
| | gtgtctgacgaggaatctctcaaag | |
| | aggtgggcatgcttatttagcaaaa | |
| | gaaaatatgctgtcagaagaccagt | |
| | aatcataacaaatttataaagaggc | |
| | tgcgctttgtcatggatcgagaata | |
| | tgggatgtacattaaaaacacacag | |
| | acaatcagacgtaccagtagtcatg | |
| | taatctggcttcagagtggggagaga | |
| | agtcaggaaaccgagatgtcccaac | |
| | atgggaccccatagattattttcat | |
| | gtgaatgtaaggcaactgctgtcat | |
| | cttccagtttctcaagacaagccaa | |
| | agtccaggttttaatgcaacgtggt | |
| | tcaatttgcaattttttgcagatatt | |
| | tcaaaatcctagagaaatggtagag | |
| | cctgtggtcaggtggcagtccagct | |
| | ttgccagtttacgagatcctgggag | |
| | gcaattcttagtttcaatggattgt | |
| | ggagttcagtagtgtggagttgaca | |
| | tgtgtggggtgagagattttactgga | |
| | tagtgattcctgtatgaagagggct | |
| | ttccatcacattctgagcaatggaa | |
| | agtaatgatgtcaaccttggttgac | |
| | aatgcacaagagattctggagaaag | |
| | catctccttcttaggcacagatatt | |
| | gaatggaatcatctgacatttgtat | |
| | tttccagtttataaaatgcctttat | |
| | atcttgtcacatttaaagttcttag | |
| | aaaatcctccttcaaagagaaatgcg | |
| | atatttctgatttacaaatgtgtgg | |
| | tctgatatctgagataggaaatcat | |
| | ttccagaagcaagcaggacattgag | |
| | tagcagatctgggattgggtgtgtc | |
| | agagcctccaacactgtcagactca | |
| | aaggtgcaggacaataagtagtctt | |
| | actctggctgtatcttctcattgtt | |
| | gcttttggacggttgccctctttcc | |
| | caaaggtgtctgtctgcacatttcg | |
| | tagagcgagtgttccgatact | |
| 3301~3558 | Exon 1(human sequence; the coding region is underlined and the remainder is a 5' untranslated region): ctaatctccctaggcaaggttcata | 4 |

TABLE 1-continued

| Nucleotide No. | Name and Sequence | SEQ ID NO |
|---|---|---|
| | tttgtgtaggttacttattctcctt | |
| | ttgttgactaagtcaataatcagaa | |
| | tcagcaggtttggagtcagcttggc | |
| | agggatcagcagcctgggttggaag | |
| | gaggggggtataaaagccccttcacc | |
| | aggagaagccgtcacacagatccac | |
| | aagctcctgacaggatggcttctca | |
| | tcgtctgctcctcctctgccttgct | |
| | ggactggtatttgtgtctgaggctg | |
| | gccctacg | |
| 3559~4506 | Intron 1: gtgagtgatcctgtgagcgatccag acatggcagttagaccttagataaa gaagaagtgccttcttccagatgtg agaactagagtactcagactctata tttaccattagactccaaagagaag agctggagtgcctctggctcttcct tctattgctttagcgcattgggtct gtagtgctcagtctctggtgtcctt agataataaagatatgagattaaca tagaaataaagatataaaagggctg gatgtatagtttagtggtccagtgt atgcctagtatgtgaaaagccttct gttcaacctctagcaatagaaaaac aagatatattctcggtggggctgtt aatattgaattctcataaaatctttt aatatatttagtatgcctattatgt tgttatattttagttctttagctaa tcaaaatgcattattgatctttctt tgtctttttttggccaacactctat tccagtctttgaaaaagtcctttaa aagagttaatcagtataattaaatg agtcaggaagtatgtgagggttatt ttacaaccagagggaattactatag caacagctgattagaatgatctcaa gaaaaagcccattctgtcttttttgc accatgcacctttcagtggctccat tcagatggagaggcaaacagagcaa tggctctcagagggcctattttccc tttgaacattcattatccatatcd ggtgcacagcagtgcatctggggggc agaaactgttcttgctttggaaaca atgdgtctatgtcatactggataaa gaagctcattaattgtcaacactta tgttatcataatgggatcagcatgt acttttggtttttgttccagagtcta tcaccggaaagaacaagccggttta ctctgacccatttcactgacatttc tcttgtctcctctgtgcccag | 5 |
| 4507~4637 | Exon 2 (human sequence; the coding region is underlined): ggcaccggtgaatcc aagtgtcctctgatggtcaaagttc tagatgctgtccgaggcagtcctgc catcaatgtggccgtgcatgtgttc agaaaggctgctgatgacacctggg agccatttgcctctgg | 6 |
| 4638~8029 | Intron 2: gtaagcttgtagaaa gcccaccatgggaccggttccaggt tcccatttgctcttattcgtgttag attcagacacacacaacttaccagc tagagggctcagagagagggctcag gggcgaagggcacgtattgctcttg taagagacacaggtttaattcctag caccagaatggcagctcataaccat ctgaaactcacagtcttaggagatc tgggtatctgacattctcttctacc caccatgtgtgtggtgcacaaattc acatgcaggcatcaaatcttataaa caacaacaaaaaaccaacaaacctg | 7 |

13

TABLE 1-continued

| Nucleotide No. | Name and Sequence | SEQ ID NO |
|---|---|---|
| | gtagcaaaagaagattagaaggtta | |
| | aacatatgagccgagagcttttgtt | |
| | ttgttttgttttgttttgttttgtt | |
| | tacatttcaaatgttatcccctttc | |
| | tcggtcccctccccaaaccctcta | |
| | ccccattctctcctcccctcttct | |
| | atgagggtgttccccaccaacccac | |
| | tcccaccttcctgctctcgaattcc | |
| | cctatactgggacatcaagccttca | |
| | cagaatcaagggcctctcctcccat | |
| | tgatgcccgacaatgtcatcctctg | |
| | ctacctatgtggctggagccatggg | |
| | tcccttcatgtatcctccttggttg | |
| | gtggtttagtctctgggaggtctgg | |
| | gggatctggttgattgatattattg | |
| | ttcttcctatgagattgcaaacccc | |
| | ttcagctccttcggtccttttaactc | |
| | ctccactggggaccccgagctcagt | |
| | ccaatggttggctgtgagcatccac | |
| | cagcagaggcctttttttttttttt | |
| | taacaaagctgctttattatgtgttgc | |
| | ttagagcatgaccaggaaccagagc | |
| | acagtccaagactgaagggaggaaa | |
| | aggggggggagtcaataaccccactg | |
| | tttcatagtggtttgcaaccctttt | |
| | atatcacagcccactttaggcaaat | |
| | aatgaaaattatagtctccagggac | |
| | agagaagatggtgcaggaagtgaag | |
| | tgcctgctcagaaaatgggggcttg | |
| | aatgtgagttcccagactctgtgta | |
| | agatgcccagcatcgaagtgcatgc | |
| | ttataacaccagcctggaggtagaa | |
| | gcttagaaacaggggtaccctgaag | |
| | ttgcttgttcaccagtgtccctgaa | |
| | tgggtaggtgcatgtttggtgagag | |
| | accctgtctcaaaaatcaaggtgta | |
| | ggataattgaaaatacctagctttg | |
| | agcttagatcatgcaaatgtgtaca | |
| | cacactcacacacaccacacacaca | |
| | aaaaaatgcagagacagagagatac | |
| | agagagacagagagatacagagaca | |
| | gagacagagagaaaaggagaaagta | |
| | aaaaacaaataatttaaagacccat | |
| | ggccacaaagaggctcaaagacaag | |
| | cacgtataaaaccatacacatgtaa | |
| | ttttaggagttttcagattccctgg | |
| | tacccgtgggtgatgcacaagcttt | |
| | gaatcccagtcttaaaatcttacga | |
| | agaacgtgttcgtgtgtgctaattt | |
| | attgatgagaggaaaggaattgaca | |
| | aagtgccttccggagcttcctgca | |
| | ttaccagactcagggttttttttaa | |
| | atgtacactcagaacagagtagctc | |
| | tgtgcaagggtagcaaccacgaagc | |
| | ttaataagaaacatatcgtgagaga | |
| | tctgcaaggcaaatctaggggctga | |
| | ccaatctcacagtcacccactagca | |
| | tgtcaacacaacttccacctgtgc | |
| | tagccacttagcaataccttgtgttgt | |
| | tctgttttgtttttgttttaacaa | |
| | agcaatttcaaagagatttctaatt | |
| | c | |
| | atctaaacaaacaaaccaaaaggaa | |
| | aacagcaaagacgccctgagcactt | |
| | agcagagcagctatgcagttatgac | |
| | tcctgggtggagactttatatcagg | |
| | cttcaactgaataacctagaacctac | |
| | tagtgctcttcatcaatccttggga | |
| | aggtcattttcttttggtgctgttt | |
| | tgagtttctatttgttaatgtcttc | |
| | ataattatacacgtgttgagcacag | |
| | catgcaaagtgattaggggaatcta | |
| | gttggagtggaatggatacccaaat | |
| | attcagactttcttgtgactcttct | |
| | ttcttgtacccacatcaaaaaaaaa | |
| | aaaatggagatgagacatggtcag | |

14

TABLE 1-continued

| Nucleotide No. | Name and Sequence | SEQ ID NO |
|---|---|---|
| | agtcactaaaaccagctgctacttt | |
| | taattacgtggggagcagtttctaa | |
| | cattgccattattgaactgatgctg | |
| | cctgggtggaaatggaaatcactta | |
| | gtatttcttgttggcaaagaattac | |
| | tgaatggattaaatttccaaaggga | |
| | gaagtcagttacaagtcttttcttt | |
| | gtttattaggctttctgctatgata | |
| | aattacactacttccagaagttacc | |
| | cttaggccatgggacactggactat | |
| | cactctgctgtcacaagagattaca | |
| | gagttagtcaaggcagcttgtgaca | |
| | ccttcagggactgtcataaacttcc | |
| | agcaagtcattaatcctgaatgcaa | |
| | tactgtgtgtgtgtgtgtctatgtgtg | |
| | tttgtatgtctgtgtgtgtcttatg | |
| | tctgtgtctctgtgtgtgtgtctgt | |
| | ttgtgtgtgtgtgtgtatgtatgcc | |
| | tgtgtgtgtcttatgtctgtgtttg | |
| | tgtgtctgtgtgtgtgtcttatgtctg | |
| | tgtttgtatgtctgtgtgtgtctgt | |
| | gtgtgtcttatgtctgtgtctctgt | |
| | gtgtgtgtgtgtgtatgtatgtatg | |
| | tatgtatgtatgtgtatgtgtttgc | |
| | atctctctgtgtgtctgcgcttata | |
| | tatttgtgtatgtgtttatgtgttc | |
| | gcctttgtgcgttgttgtggggattga | |
| | atccaggggaatacaaatgttaaga | |
| | aagaacgttaccactaagcttcacc | |
| | tgtaggccttaaagcttttctttct | |
| | tttaaaaattgtaattaattcattt | |
| | tcagtcaggatctccacacctcgtc | |
| | cctgctgctctagaactcactattt | |
| | aaacacaatcgccctcaaacctgca | |
| | gcaaccctcccgcctctaccctgcg | |
| | agcactagaataataacaggtgacc | |
| | ccacacgcctagattaagaccttta | |
| | aggtaaacattttactatattttag | |
| | tctcataagacaagatgctacaata | |
| | aagctgtacataaagttccctcgaa | |
| | tttcttgctattttaactcaaacat | |
| | aaggatttcctcctttttgattcag | |
| | gtaacagaaaaaatacacaggtaca | |
| | tacatgtacacacatgaacacacac | |
| | gcatcacaaccacatatgcgcacgc | |
| | ttgtgtgatctatcatttaccatgc | |
| | cactgaactcttctttccccataaa | |
| | ttcctctggacttgtgtgccctcca | |
| | g | |
| 8030~8165 | Exon 3 (human sequence; the entire sequence (underlined) is the coding region): gaaaaccagtgagtctgga gagctgcatgggctcacaactgagg aggaatttgtagaagggatatacaa agtggaaatagacaccaaatcttac tggaaggcacttggcatctccccat tccatgagcatgcagag | 8 |
| 8166~11681 | Intron 3: gtaagtggacacacca agttgtttggattttgttttttagtc tcaggaaattcccttcgctcttgct gtacgatgggcatgagtggaaagta gattccacagccagaatccacagtg ctgggaaagcaagccttctgaattt ttctaaaactcatttagcaacatgg cctgaacctgttcacactgcttatg gtcagctaactatatttatgtaaat attcattttctctgttgaggaaatgt tagtatttgcttttgaggcaacctc cagataccatggagggcatgtcata gtcaaagagagggctccctatggta | 9 |

15

TABLE 1-continued

| Nucleotide No. | Name and Sequence | SEQ ID NO |
|---|---|---|
| | tttctctaaattctggcatttcctt | |
| | tattccaaagcacatctagtgtccc | |
| | cagaagtttgggtagacaattcttg | |
| | gcaacacagagaattacaacatgtt | |
| | caaaacccaacagcttaatatctaa | |
| | atcatcaagcaaacatcacatggca | |
| | aagggatttctgaatcaaaactgtt | |
| | tcatccttatgatcaacctatggag | |
| | gtctagcctcgacttacacccattt | |
| | taccaataagctaagagaagctaag | |
| | ttcctcatcaaggacacaaggctag | |
| | catgtgtgagcaagtgacagagttg | |
| | ccctctatgttggttagtgtgcctt | |
| | agccagtgtctcagtaagaaatgga | |
| | gctaaatcaaaacccaaggccaaca | |
| | gccaaaggcacatgagtaacctttg | |
| | cttggcactgggctcagtttccctg | |
| | gctcctctcagtcctcagttcacag | |
| | aggcagctgtcatgcaaatagaatc | |
| | caagcttgttggtcagacctggaga | |
| | taacaaattccatcaaaaatagctc | |
| | ctcatgtgacctagtttgctgtctg | |
| | ttgctatgatacacaccatgaccga | |
| | aaagcaaccctggggagagaagggt | |
| | ttatttcatcttacagcttacagtt | |
| | caccatggaggaaagccaggtggga | |
| | acctggaagtggaaattgaagcaga | |
| | gaccagaaaggaatgctgtttactg | |
| | gctggcttagctccttttcttatac | |
| | agcttaggtctatgtgcccaggggga | |
| | tggtactgccgagcataggctgagc | |
| | ccgcctacatcaaccattagtcaaa | |
| | aaaaggtccatagacttgcctacag | |
| | gccaatctcatggaggcaataccc | |
| | agtggagggtccctcttcgcaggtt | |
| | actctagtttgtgtcaagttgacaa | |
| | aacctaaccacaaagcacaaacagg | |
| | gtctgcccttgtggcttagccatgg | |
| | atgacactctcagatgatggtgtta | |
| | ccagacaaaccagaggggctcacca | |
| | agagtctgccacctaccaaggtagt | |
| | actctactcctcactgggcaccaac | |
| | acccatattagctgggccagtacag | |
| | gacccttgctgtttcctgcatgaat | |
| | tgtccatagaccctgggtctcagcc | |
| | tgccgggagtacctgtaagtagtcg | |
| | cctcaaacacattattcctgttgga | |
| | agacttgtctgattctcttttagaa | |
| | ctcaatcaacaaacgttttttatttt | |
| | gttttggcttttttggagacaagatc | |
| | tctcataggccagcctgacttgaat | |
| | gtagctgaggatgacctgtgctgct | |
| | aatcttctcgcctcttcctcccaag | |
| | tggtaggataataggcataagacac | |
| | cacagcagttttactccataccagg | |
| | gctctgaacccagactttaaacact | |
| | ctatcaactgattcacattcccacc | |
| | ccatcattcaacaaacatttgaaaa | |
| | ataaaacccttctgccttgagcact | |
| | ctgctaaatacagcctttgagtgcg | |
| | gagtatttcctcacaaccagggtcc | |
| | aagatgaccccatcatacataccac | |
| | ggaaaattaggagatgtttttaggt | |
| | ctctttgcttggggtaatttttatg | |
| | tgtgtgtgtacacagccctgtgcgt | |
| | gtgtgtgtgtgtgtgtgtgtgtgtg | |
| | tacaggcacacacgtgtatgcatgt | |
| | agaggctacataaaaaccttaggtg | |
| | tcattctcaggcactctgttcaccc | |
| | cttcacacagcccgaacacacaaaa | |
| | tttgaggcattagcctggagctcac | |
| | cagttaggctagactgacttgccag | |
| | cagaccccaggctgtctccatctcc | |
| | ccagctctgggattacaaactctat | |
| | cataccagacattttttatacatatt | |
| | ctgagcataaaattcatgtcttcag | |

16

TABLE 1-continued

| Nucleotide No. | Name and Sequence | SEQ ID NO |
|---|---|---|
| | gctaacaagtcaagagcttaaatga | |
| | ctgagctctcttacgtggtggattt | |
| | tttttaaaactacataatatctttt | |
| | tttttttttttcacttctggggaaga | |
| | aacaaatgagcctgagtgacaatgc | |
| | gacagaaaagaaattttgaggagtg | |
| | tgtgtgtctgtgtgtgtggtggcac | |
| | atgcctctcatctaatgctagaggc | |
| | tacagtagaatgctcctgaattagt | |
| | ggccagccaaggccaagggctaggg | |
| | ttgtaactcagtggcagagggcttg | |
| | cctagcattcgcaggatttgatcca | |
| | tagcgctataaataataataaataa | |
| | atacaacagtctaagatgattctcc | |
| | ctttcatttatctggatgttatttt | |
| | tgtgttagttttactctgtcatcca | |
| | atcattgtttgccctatatttggac | |
| | atttaaaaaaaaatctttattccaag | |
| | tgtgttcaaagctgtatccaaaacc | |
| | tgtccaccaaatgagtccaatgaca | |
| | tacatcttctatattaccatctgtt | |
| | ccagatttggctgactcccggcacc | |
| | tgggctgttgctgcacccatgtctc | |
| | agatagtctagtgatttgagaagtg | |
| | actagtaattgcaaaatccagactt | |
| | tgtccagaaacttctatgagctcca | |
| | aaactttcatttacatttctgccag | |
| | ccacaaaccgcttgtgttgtggaga | |
| | gaaccctgtgatgtcttcccacagc | |
| | atctcagccttgtttcttcccttaa | |
| | aatattcatctttttcacattagaac | |
| | atgcaaagggacagtgggagcgaaa | |
| | cccctggactgggacgcacgaagcc | |
| | ttccttttctggtcaggctctcactg | |
| | tagaaacttaggccggtttcagcat | |
| | gcagtctgctggagaatggctcctg | |
| | ccaacattccaggtctggaagtttg | |
| | tagtggagttgttgataaccactgt | |
| | tcgccacaggtcttttgtttgtggg | |
| | tgtcagtgtttctactctcctgact | |
| | tttatctgaacccaagaaagggaac | |
| | aatagccttcaagctctctgtgact | |
| | ctgatctgaccagggccacccacac | |
| | tgcagaaggaaacttgcaaagagag | |
| | acctgcaattctctaagagctccac | |
| | acagctccaaagacttaggcagcat | |
| | attttaatctaattattcgtccccc | |
| | aaccccaccccagaggacagttaga | |
| | caataaaaggaagattaccagctta | |
| | gcatcctgtgaacactttgtctgca | |
| | gctcctacctctgggctctgttaga | |
| | actagctgtctctcctctctcctag | |
| 11682~12377 | Exon 4 (human sequence; the coding region is underlined and the remainder is a 3' untranslated region): gtggtattcacagccaacgactccgg cccccgccgctacaccattgccgcc ctgctgagccccactcctattccac cacggctgtcgtcaccaatcccaag gaatgagagactcagcccaggagga ccaggatcttgccaaagcagtagca tcccatttgtaccaaaacagtgttc ttgctctataaaccgtgttagcagc tcaggaagatgccgtgaagcattct tattaaaccacctgctatttcattc aaactgtgtttctttttttatttcct cattttttctccctgctcctaaaac ccaaaatcttctaaagaattctaga aggtatgcgatcaaactttttaaag aaagaaaatactttttgactcatgg tttaaaggcatcctttccatcttgg ggaggtcatgggtgctcctggcaac ttgcttgaggaagataggtcagaaa | 10 |

TABLE 1-continued

| Nucleotide No. | Name and Sequence | SEQ ID NO |
|---|---|---|
| | gcagagtggaccaaccgttcaatgt ttttacaagcaaaacatacactaagc atggtctgtagctattaaaagcaca caatctgaagggctgtagatgcaca gtagtgtttcccagagcatgttca aaagccctgggttcaatcacaatac tgaaaagtaggccaaaaaacattct gaaaatgaaatatttgggtttttt ttataacctttagtgactaaataaa gacaaatctaagagactaa | |
| 12378~14685 | 3' homologous arm: ctgtggc tgcttatatcatgttaatttgggtc cccaaaattgtttgtatgaacatcc acactggtaaataaagttgtggcac ccaatggctgggcagggtagatgga ggcaggacttttagattcctggggg agggagaaagaaggaggaatcacca tgcctagagaaggagaggagaaaca ccatgcctggaaaggtgcgggacag agaacatagccaccatgtaggagca ggaggatagcagccaaagagggctg tacgtctgggtctggggtggccaag agagaatgtaggagttagtaaagta ataactcgggaatatcggagggagg tggattagccacatggaggttagga agtggcccagccattgagctgatta aagcatatcaaaatataaagaccct gtgcgtgtgtgtgtgtgtgtgtgtg tgtgtgtgtgtgtgtgtgtgtttca tttgagaaccaagaacattcgggca agtagtgaggaatgagcctcagcag gtgggatctattaaagtatttaatt gggtatactacaactgattcttcag gcatttcttgttaagcactttactc atttgagggccataacagtttcttt gcacaagaatgggcctatccgcagt caggcctgggactccgggccccacc ccttgctgctgagctatttataatg atacattcaggtagaaggggagtca tggtcttcagttgtgtgctcactgg tgactccaccaggctctgatggaca gttccaagccaaaatgaagaaacaa gccacaaaacgacatgaatctggga gaagggttggtggtaacgtgcggag gggttgggaggtgggaggcagctaa gagatgacaaggaagggagcatcag cgtgggctgtgtgcatgcataaaac gaaagcaaacaaaatcaatcactaa accatgtttaagaacagtgagttcc aaaagggataaacctgcagcaaccca gcttcacttcccaggcaattcctac cttcccatcacagttcatagaacat attcctcctaaactggcaattttcc ttccagtctttcaaaatgaaataag cttggaatcaattccacttcccag atctctctaccccctctaatccactt tagaccaattctacctgaatcagaa cccagctctcaggagacagaagcag agacaggaggatgtccatgagttca aggccattctagtgagttctaagcc aaccaaaactacataatgagacctt gtctaacaacaacttagtcaaatcc taaatccatgtttaattgatacaca cactcatgcacacgcacacacacgt gtaatatgaacaaaacgaaacaaaa tagatttgtaatggacgagaataaa ttcaatttttaaccactctgggtt aatataatcagactggtttttaaac tctaaagttggcagtgtgtgcacac acatgtccaacgcatgaggtgtgt ctcaaaaagcataattataagtatt gaactcctacctgcaacatttgata gcacctgtcaaacaaggaaatgaag catatcttttgcctcaagctatatt | 11 |

TABLE 1-continued

| Nucleotide No. | Name and Sequence | SEQ ID NO |
|---|---|---|
| | ttatccaccgagcgctcgtagcaga ggcagaattatttctccccgatccg tcgtttccccggcgattccttcctt tacttcacagtccatagagcttcct aagcgctgttcgttttccctccagc ctttcaaaatggaaataagcttaga agcaattccatttccccggctctcc atttctctgggtgggagctgcccc agttaatttaagccaaagcagatg gtaattcatctttggcaaaaccaag taaatactgaaggtccactctggag cctctgtgagcaagaaggtgggttg cacttggacttttctaaaataaaccc tagggatgtgcacacagccccccagt gcagcagtcaaccacttgctgttgc ttcctcttatttactcccaggaagc aggtggttagagacacgggtacaag gtatgatggaagagaaggcccagac agatgctacaaggtgaaaccccagaac agctgtcaccatgagaacgtgtgct cagttaaaagaacaacactgctcat ctcaggtaacctcaggagctagcat ttggaaagcactttagatgtgtttc ccagactccagaaaatagcacctac cacacagggcttttaaatgtttgag catcatatagcatcccttctaagta tgtggaatgaattaatgaatgaacc aatagatgaatgaagtaaaggatta gttctaggtaggcaaatctgagcct tc | |
| 14686~16913 | pBSK: GCGGCCGCCACCGCGGTGGA GCTCCAGCTTTTGTTCCCTTTAGTG AGGGTTAATTGCGCGCTTGGCGTAA TCATGGTCATAGCTGTTTCCTGTGT GAAATTGTTATCCGCTCACAATTCC ACACAACATACGAGCCGGAAGCATA AAGTGTAAAGCCTGGGGTGCCTAAT GAGTGAGCTAACTCACATTAATTGC GTTGCGCTCACTGCCCGCTTTCCAG TCGGGAAACCTGTCGTGCCAGCTGC ATTAATGAATCGGCCAACGCGCGGG GAGAGGCGGTTTGCGTATTGGGCGC TCTTCCGCTTCCTCGCTCACTGACT CGCTGCGCTCGGTCGTTCGGCTGCG GCGAGCGGTATCAGCTCACTCAAAG GCGGTAATACGGTTATCCACAGAAT CAGGGGATAACGCAGGAAAGAACAT GTGAGCAAAAGGCCAGCAAAAGGCC AGGAACCGTAAAAAGGCCGCGTTGC TGGCGTTTTTCCATAGGCTCCGCCC CCCTGACGAGCATCACAAAAATCGA CGCTCAAGTCAGAGGTGGCGAAACC CGACAGGACTATAAAGATACCAGGC GTTTCCCCCTGGAAGCTCCCTCGTG CGCTCTCCTGTTCCGACCCTGCCGC TTACCGGATACCTGTCCGCCTTTCT CCCTTCGGGAAGCGTGGCGCTTTCT CATAGCTCACGCTGTAGGTATCTCA GTTCGGTGTAGGTCGTTCGCTCCAA GCTGGGCTGTGTGCACGAACCCCCC GTTCAGCCCGACCGCTGCGCCTTAT CCGGTAACTATCGTCTTGAGTCCAA CCCGGTAAGACACGACTTATCGCCA CTGGCAGCAGCCACTGGTAACAGGA TTAGCAGAGCGAGGTATGTAGGCGG TGCTACAGAGTTCTTGAAGTGGTGG CCTAACTACGGCTACACTAGAAGGA CAGTATTTGGTATCTGCGCTCTGCT GAAGCCAGTTACCTTCGGAAAAAGA GTTGGTAGCTCTTGATCCGGCAAAC AAACCACCGCTGGTAGGGATCCAA GAAGATCCTTTGATCTTTTCTACGG GGTCTGACGCTCAGTGGAACGAAAA CTCACGTTAAGGGATTTTGGTCATG | 12 |

TABLE 1-continued

| Nucleotide No. | Name and Sequence | SEQ ID NO |
|---|---|---|
| | AGATTATCAAAAAGGATCTTCACCT | |
| | AGATCCTTTTAAATTAAAAATGAAG | |
| | TTTTAAATCAATCTAAAGTATATAT | |
| | GAGTAAACTTGGTCTGACAGTTATT | |
| | ACCAATGCTTAATCAGTGAGGCACC | |
| | TATCTCAGCGATCTGTCTATTTCGT | |
| | TCATCCATAGTTGCCTGACTCCCCG | |
| | TCGTGTAGATAACTACGATACGGGA | |
| | GGGCTTACCATCTGGCCCCAGTGCT | |
| | GCAATGATACCGCGAGACCCACGCT | |
| | CACCGGCTCCAGATTTATCAGCAAT | |
| | AAACCAGCCAGCCGGAAGGGCCGAG | |
| | CGCAGAAGTGGTCCTGCAACTTTAT | |
| | CCGCCTCCATCCAGTCTATTAATTG | |
| | TTGCCGGGAAGCTAGAGTAAGTAGT | |
| | TCGCCAGTTAATAGTTTGCGCAACG | |
| | TTGTTGCCATTGCTACAGGCATCGT | |
| | GGTGTCACGCTCGTCGTTTGGTATG | |
| | GCTTCATTCAGCTCCGGTTCCCAAC | |
| | GATCAAGGCGAGTTACATGATCCCC | |
| | CATGTTGTGCAAAAAAGCGGTTAGC | |
| | TCCTTCGGTCCTCCGATCGTTGTCA | |
| | GAAGTAAGTTGGCCGCAGTGTTATC | |
| | ACTCATGGTTATGGCAGCACTGCAT | |
| | AATTCTCTTACTGTCATGCCATCCG | |
| | TAAGATGCTTTTCTGTGACTGGTGA | |
| | GTACTCAACCAAGTCATTCTGAGAA | |
| | TAGTGTATGCGGCGACCGAGTTGCT | |
| | CTTGCCCGGCGTCAATACGGGATAA | |
| | TACCGCGCCACATAGCAGAACTTTA | |
| | AAAGTGCTCATCATTGGAAAACGTT | |
| | CTTCGGGGCGAAAACTCTCAAGGAT | |
| | CTTACCGCTGTTGAGATCCAGTTCG | |
| | ATGTAACCCACTCGTGCACCCAACT | |
| | GATCTTCAGCATCTTTTACTTTCAC | |
| | CAGCGTTTCTGGGTGAGCAAAAACA | |
| | GGAAGGCAAAATGCCGCAAAAAAGG | |
| | GAATAAGGGCGACACGGAAATGTTG | |
| | AATACTCATACTCTTCCTTTTTCAA | |
| | TATTATTGAAGCATTTATCAGGGTT | |
| | ATTGTCTCATGAGCGGATACATATT | |
| | TGAATGTATTTAGAAAAATAAACAA | |
| | ATAGGGGTTCCGCGCACATTTCCCC | |
| | GAAAAGTGCCAC | |

Figure 2:
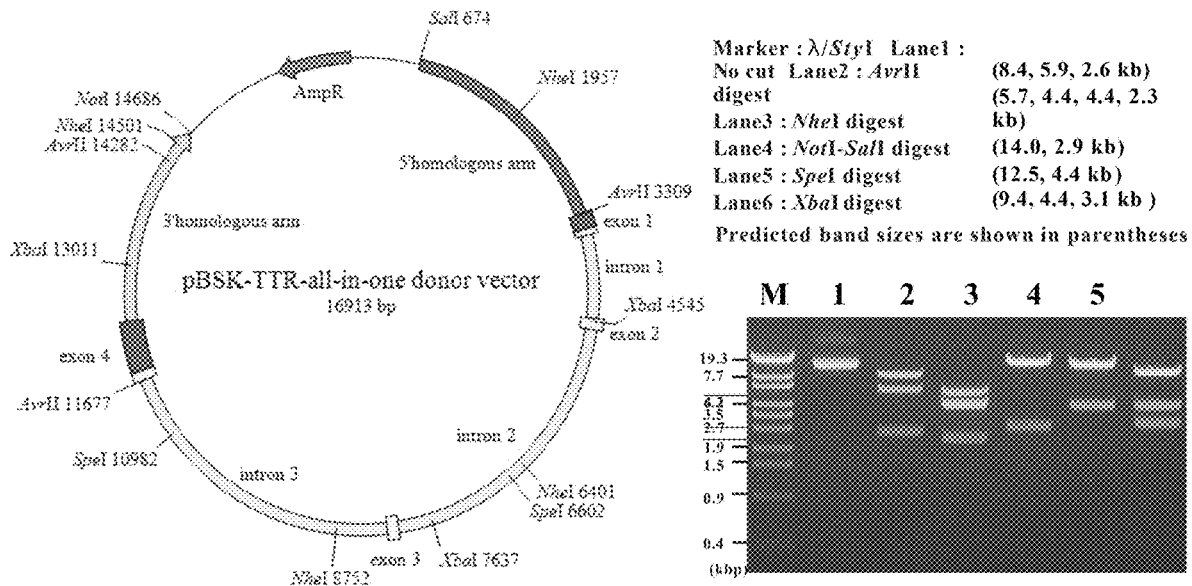
FIG. 2 is a diagram showing the restriction map of pBSK-TTR-all-in-one donor vector.

To confirm the structure of the prepared donor vector, the donor vector was digested with restriction enzymes and its electrophoresis pattern was analyzed. The observed DNA cleavage pattern was in good agreement with the pattern expected from the vector design (FIG. 2). Moreover, the nucleotide sequences of all the PCR-amplified DNA fragments were determined and compared with the C57BL/6J mouse genomic nucleotide sequence registered with NCBJ, indicating that they were completely identical with each other. This proves that a gene only whose exons have been humanized can be prepared in the above manner.

Guide RNAs

The nucleotide sequences and others required for guide RNA preparation have already been reported in detail (Ran et al. Nat. Protoc. 8:2281-2308, 2013). Moreover, vectors (e.g., pX330), which can express crRNA, tracrRNA and Cas9 in a single vector, have been developed (Sakuma et al. Sci. Rep. 4:5400, 2014), and are available from Addgene or elsewhere.

Based on the above documents, etc., 20 bp nucleotide sequences capable of efficiently disrupting exon 1 were analyzed by search software (Crispr design tool). For guide RNA selection, from among nucleotide sequences showing high scores, those with many mismatches were selected so as to avoid gRNA-mediated cleavage of the humanized coding region. As a result, the following two candidate sequences were selected (FIG. 3).

Ex1-gRNA1:
(SEQ ID NO: 13)
CTGCTCCTCCTCTGCCTTGC TGG

Ex1-gRNA2:
(SEQ ID NO: 14)
GCAGAGGAGGAGCAGACGAT GAG

Figure 4:
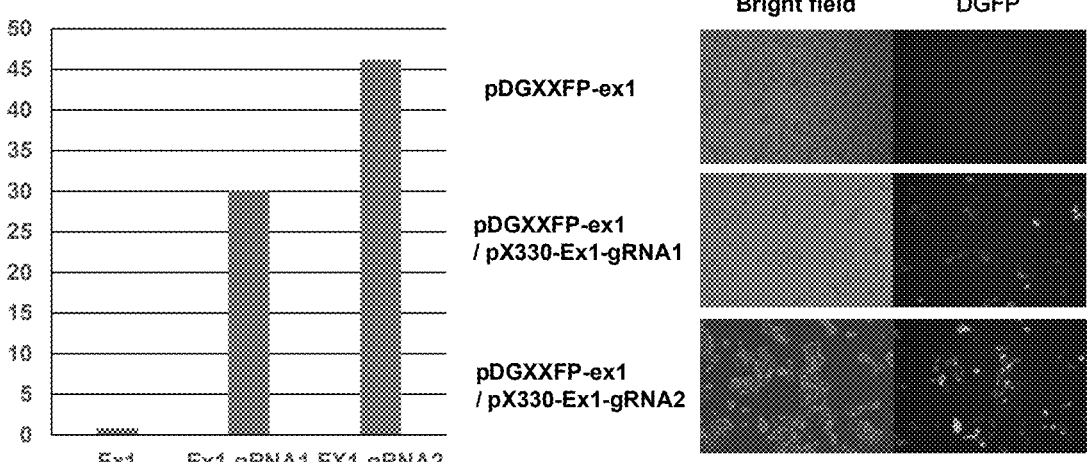
FIG. 4 is a diagram showing the evaluation of gRNAs for exon 1.

To evaluate the efficiency of guide RNAs carrying these two sequences, the procedures of Mashiko et al. were used (Mashiko et al. Sci. Rep. 3: 3355, 2013). First, approximately 500 bp Ttr genomic fragments containing the target sequences of Cas9 (SEQ ID NOs: 15 and 16) were each inserted between the 5'- and 3'-sequences of the DasherGFP gene (DNA2.0 Inc.) located downstream of the CMV promoter to construct non-fluorescent DasherGXXFP expression vectors (pDGXXFP-ex1 and pDGXXFP-ex4). These expression vectors were introduced into HEK293T cells together with guide RNA-Cas9 expression vectors targeting the corresponding regions (pX330-Ex1-gRNA1, pX330-Ex1-gRNA2, pX330-Ex4-gRNA1 and pX330-Ex4-gRNA2). Once the gRNA-guided Cas9 protein has cleaved the target sequence and the generated ends have been repaired by homology-directed repair, the nucleotide sequence of DasherGXXFP will be reconstructed into DasherGFP and the expressed protein will emit fluorescence. It was pX330-Ex1-gRNA2 that was determined to be higher in the proportion of fluorescence-emitting cells and high in the cleavage activity of Cas9 (FIG. 4).

The same search was made for exon 4 to select the following two candidate sequences (FIG. 5).

Ex4-gRNA1:
(SEQ ID NO: 17)
CTGCGATGGTGTAGTGGCGA TGG

Ex4-gRNA2:
(SEQ ID NO: 18)
GTGGCGATGGCCAGAGTCGT TGG

The target sequences of Cas9 are shown in SEQ ID NOs: 19 and 20 (FIG. 5).

Figure 6:
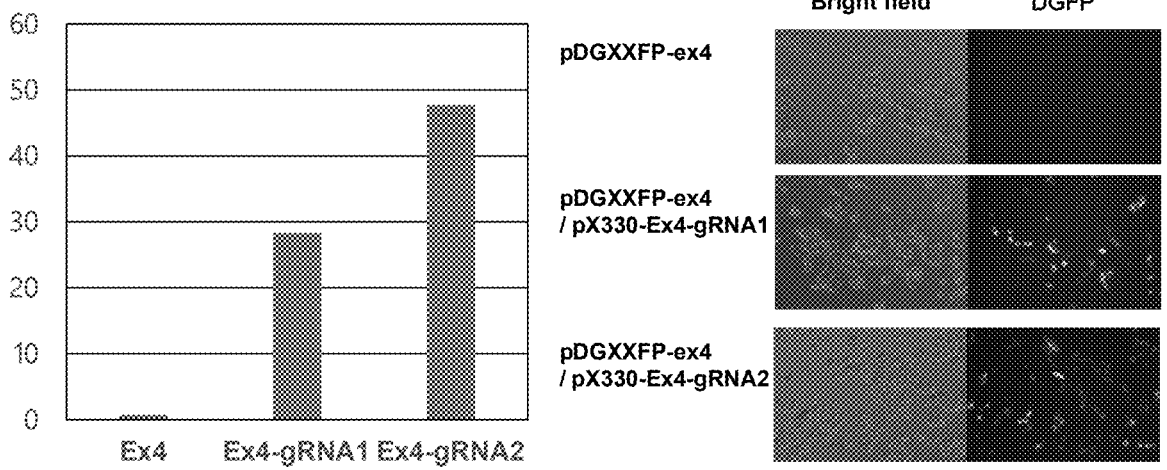
FIG. 6 is a diagram showing the evaluation of gRNAs for exon 4.

The efficiency of guide RNAs carrying these two sequences was evaluated in the same manner as above. The results obtained are shown in FIG. 6. It was pX330-Ex4-gRNA2 that was determined to be higher in the proportion of fluorescence-emitting cells and high in the cleavage activity of Cas9 (FIG. 6).

Establishment of ES cells

In this example, for establishment of an exon-humanized mouse, the donor vector and the guide RNAs (pX330-Ex1-gRNA2 and pX330-Ex4-gRNA2) were used to establish ES cells. The donor DNA, the vector (pBSK-TTR-all-in-one donor vector) and the puro expression vector were co-transfected by electroporation into ES cells (C57BL/6N-derived cell line RENKA). As a result, 10 clones were obtained in which all the four exons have been replaced with human TTR gene exons (Table 2). However, it was only three clones (a6221, a6226 and a6232) in which only the DNA fragments expected after restriction enzyme cleavage were detected, and the other clones were found to have unexpected mutations and/or deletions.

The above three clones were analyzed for their nucleotide sequences. As a result of the analysis, a6221 was found to have a so-called mosaic allele because we found not only an allele in which all the exons have been replaced with human TTR gene exons, but also an allele in which only exon 1, exon 2 and exon 4 have been replaced with human TTR gene exons, an allele in which all the exons have been replaced with human TTR gene exons, except that only a single nucleotide in exon 2 has not been humanized, and an allele in which all the exons have been replaced with human TTR gene exons, except that intron 1 has a single nucleotide mutation.

a6226 was also found to have a mosaic allele because we found not only an allele in which all the exons have been replaced with human TTR gene exons, but also an allele in which all the exons have been replaced with human TTR gene exons, except that intron 2 has a single nucleotide mutation.

a6232 was found to have only an allele in which all the exons have been replaced with human TTR gene exons.

Moreover, the wild-type allele was not observed in these ES cell clones.

As can be seen from the above results, a6221, a6226 and a6232 were all found to have an allele in which all the exons have been replaced with human TTR gene exons.

TABLE 2

| gRNA-Cas9 (μg) | Donor vector (μg) | Puro vector (μg) | Number of clones analyzed | Number of positive clones | Fully replaced |
|---|---|---|---|---|---|
| 5.0 | 38.0 | 2.0 | 20 | 3 | 3 |
| 10.0 | 28.0 | 2.0 | 20 | 7 | |

Establishment of Mouse Strain (Ttr$^{hTTRexon}$)

The above homologous recombinant ES cell clones (a6221, a6226 and a6232) and eight-cell embryos of the ICR strain were used to prepare chimeric embryos by the aggregation method. At the expected date of delivery, recipient female mice transplanted with these chimeric embryos were confirmed to give birth, and pregnant mice which had not given birth were subjected to cesarean section. The resulting chimeric mice were kept until weaning, and the chimeric rate was determined based on their coat color at the time of weaning. It should be noted that the chimeric rate was determined by visual inspection of coat color distribution over the whole body. Five 100% chimeric mice were obtained from a6221-derived ES cells, although the chimeric rate was low in the other cases (Table 3).

TABLE 3

| Clone No. | Number of recipient females | Number of pups born | Number of chimeras at the time of weaning | Coat color chimeric rate | | | | | |
|---|---|---|---|---|---|---|---|---|---|
| | | | | 100% | | 60% | | 50% or less | |
| | | | | ♂ | ♀ | ♂ | ♀ | ♂ | ♀ |
| a6221 | 4 | 16 | 5 | 5 | | | | | |
| a6226 | 4 | 12 | 1 | | | | 1 | | |
| a6232 | 8 | 14 | 4 | | | | | | 4 |

Figure 8:
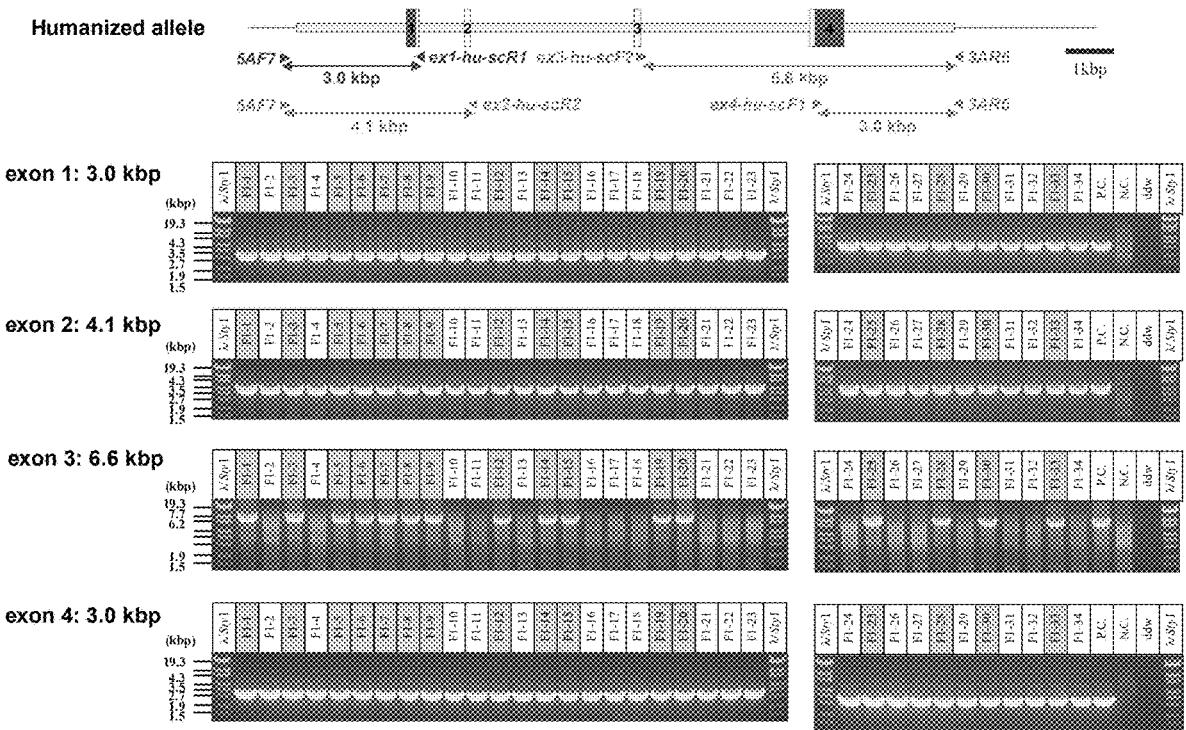
FIG. 8 is a diagram showing the PCR analysis of F1 mice.

F1 pups were produced by crossing the above 100% chimeric mice obtained from a6211 with wild-type mice. As a result, ES-derived pups were obtained from all the chimeras. After DNA extraction from the body tissue of each F1 pup, humanized exons were detected under PCR conditions using primers specific to the humanized allele (FIG. 7). As a result, exon 1, exon 2 and exon 4 were confirmed to be humanized in all pups, while exon 3 was confirmed to be humanized in 16 pubs (♂ 8 and ♀ 8) (FIG. 8). Then, nucleotide sequence analysis was conducted by direct sequencing to confirm the absence of any unexpected mutation in the humanized sequence for each exon in these 16 pups in which all the exons had been humanized (Nos. F1-1, F1-3, F1-5, F1-6, F1-7, F1-8, F1-9, F1-12, F1-14, F1-15, F1-19, F1-20, F1-25, F1-28, F1-30 and F1-33).

Figure 9:
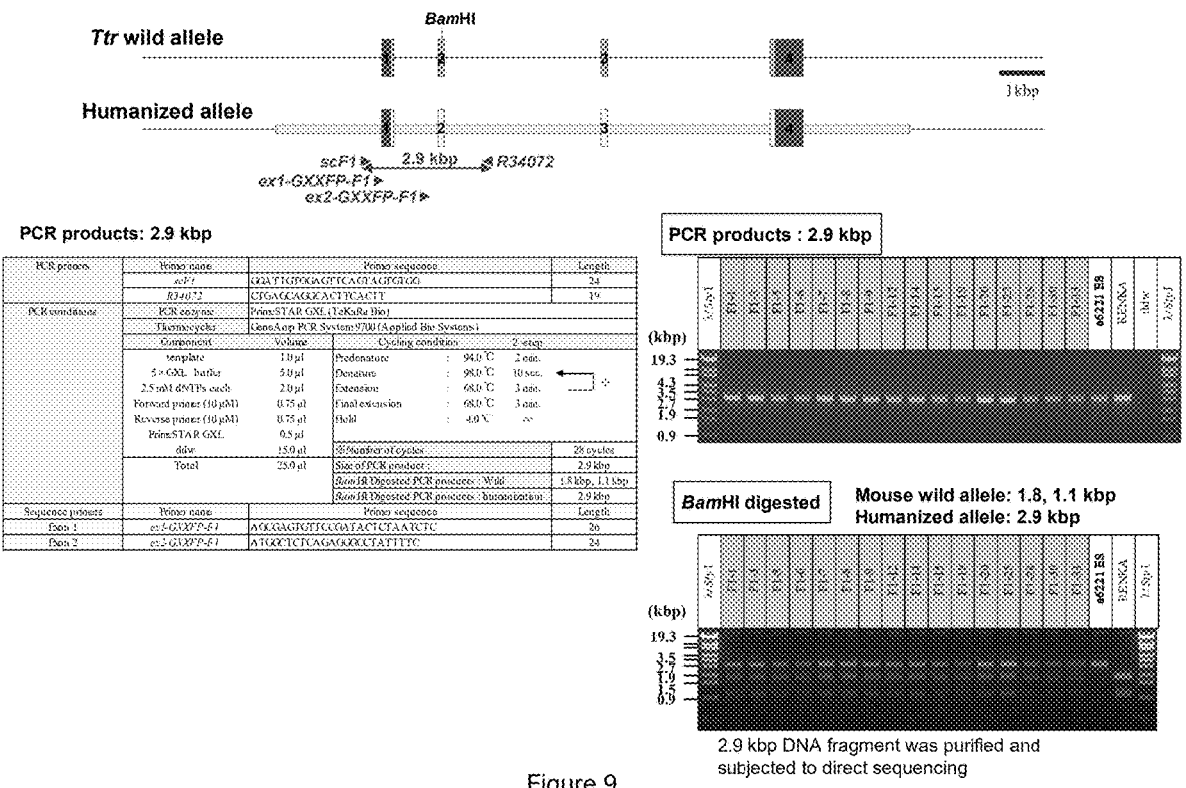
FIG. 9 is a diagram showing the amplification of exons 1 and 2.

First, a 2.9 kbp DNA region containing exon 1 and exon 2 was amplified with the primers shown in the upper panel of FIG. 9 and under the PCR conditions shown in the left panel of FIG. 9.

```
scF1:
                                    (SEQ ID NO: 21)
ggattgtggagttcagtagtgtgg R34072:
                                    (SEQ ID NO: 22)
ctgagcaggcacttcactt ex1-GXXFP-F1:
                                    (SEQ ID NO: 23)
agcgagtgttccgatactctaatctc ex2-GXXFP-F1:
                                    (SEQ ID NO: 24)
atggctctcagagggcctattttc
```

A 2.9 kb band was detected in all pups (FIG. 9, right panel). These PCR products were treated with BamHI to digest mouse sequences (1.8 kbp and 1.1 kbp) (FIG. 9, bottom right panel), and the humanized sequence (2.9 kbp) not cleaved with BamHI was purified and then subjected to direct sequencing. As a result, the humanized 16 pups were confirmed to have the same sequences as expected for both exon 1 (FIG. 10) and exon 2 (FIG. 11). In FIG. 10, the nucleotide sequence of mouse exon 1 is shown in SEQ ID NO: 25 and the nucleotide sequence of human exon 1 is shown in SEQ ID NO: 26. In FIG. 11, the nucleotide sequence of mouse exon 2 is shown in SEQ ID NO: 27 and the nucleotide sequence of human exon 2 is shown in SEQ ID NO: 28.

Figure 12:
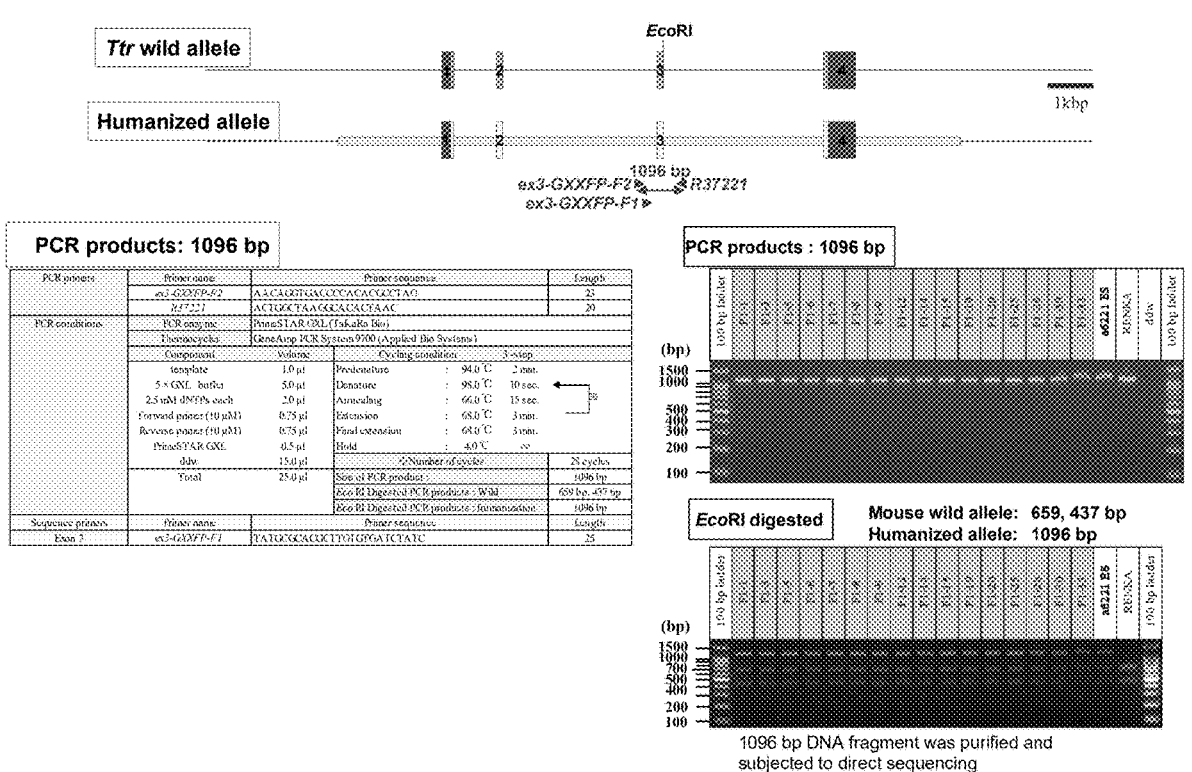
FIG. 12 is a diagram showing the amplification of exon 3.

It should be noted that the mutation in intron 1 confirmed in the ES cell clone (a6221) was not observed. Thus, this mutation is deemed to be an error during PCR amplification. Likewise, a 1096 bp DNA region containing exon 3 was amplified with the primers shown in the upper panel of FIG. 12 (show below) and under the PCR conditions shown in the left panel of FIG. 12.

```
ex3-GXXFP-F2:
                                    (SEQ ID NO: 29)
aacaggtgaccccacacgcctag R37221:
                                    (SEQ ID NO: 30)
actggctaaggcacactaac ex3-GXXFP-F1:
                                    (SEQ ID NO: 31)
tatgcgcacgcttgtgtgatctatc
```

These PCR products were treated with EcoRI to digest mouse sequences (659 bp and 437 bp) (FIG. 12, bottom right panel), and the humanized sequence (1096 bp) not cleaved with EcoRI was purified and then subjected to direct sequencing. As a result, the 16 pups in which all the exons had been humanized were confirmed to have the same sequence as expected (FIG. 13). In FIG. 13, the nucleotide sequence of mouse exon 3 is shown in SEQ ID NO: 32, and the nucleotide sequence of human exon 3 is shown in SEQ ID NO: 33.

Figure 14:
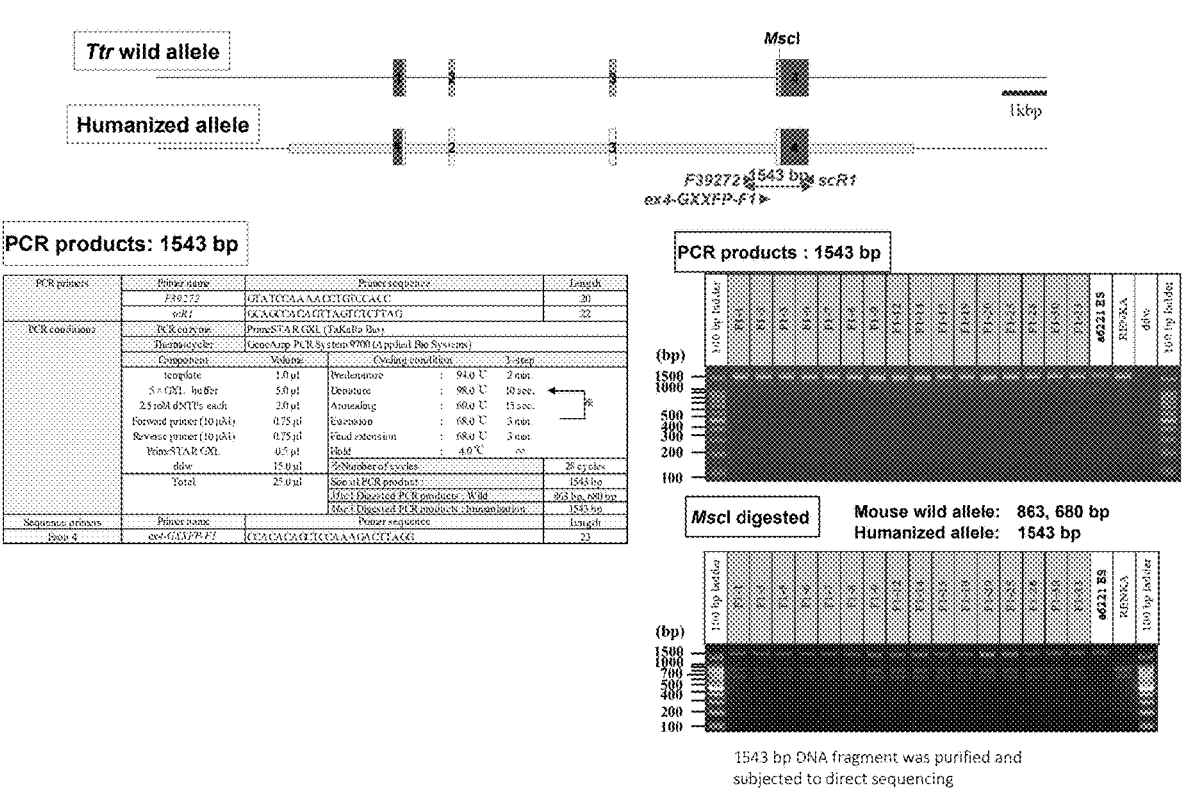
FIG. 14 is a diagram showing the amplification of exon 4.

Furthermore, a 1543 bp DNA region containing exon 4 was amplified with the primers shown in the upper panel of FIG. 14 (shown below) and under the PCR conditions shown in the left panel of FIG. 14 (FIG. 14, right panel).

```
F39272:
                                (SEQ ID NO: 34)
gtatccaaaacctgtccacc scR1:
                                (SEQ ID NO: 35)
gcagccacagttagtctcttag ex4-GXXFP-F1:
                                (SEQ ID NO: 36)
ccacacagctccaaagacttagg
```

These PCR products were treated with MscI to digest mouse sequences (863 bp and 680 bp) (FIG. 14, bottom right panel), and the humanized sequence (1543 bp) not cleaved with MscI was purified and then subjected to direct sequencing. As a result, the 16 pups in which all the exons had been humanized were confirmed to have the same sequence as expected (FIG. 15). In FIG. 15, the nucleotide sequence of mouse exon 4 is shown in SEQ ID NO: 37, and the nucleotide sequence of human exon 4 is shown in SEQ ID NO: 38.

Figure 16:
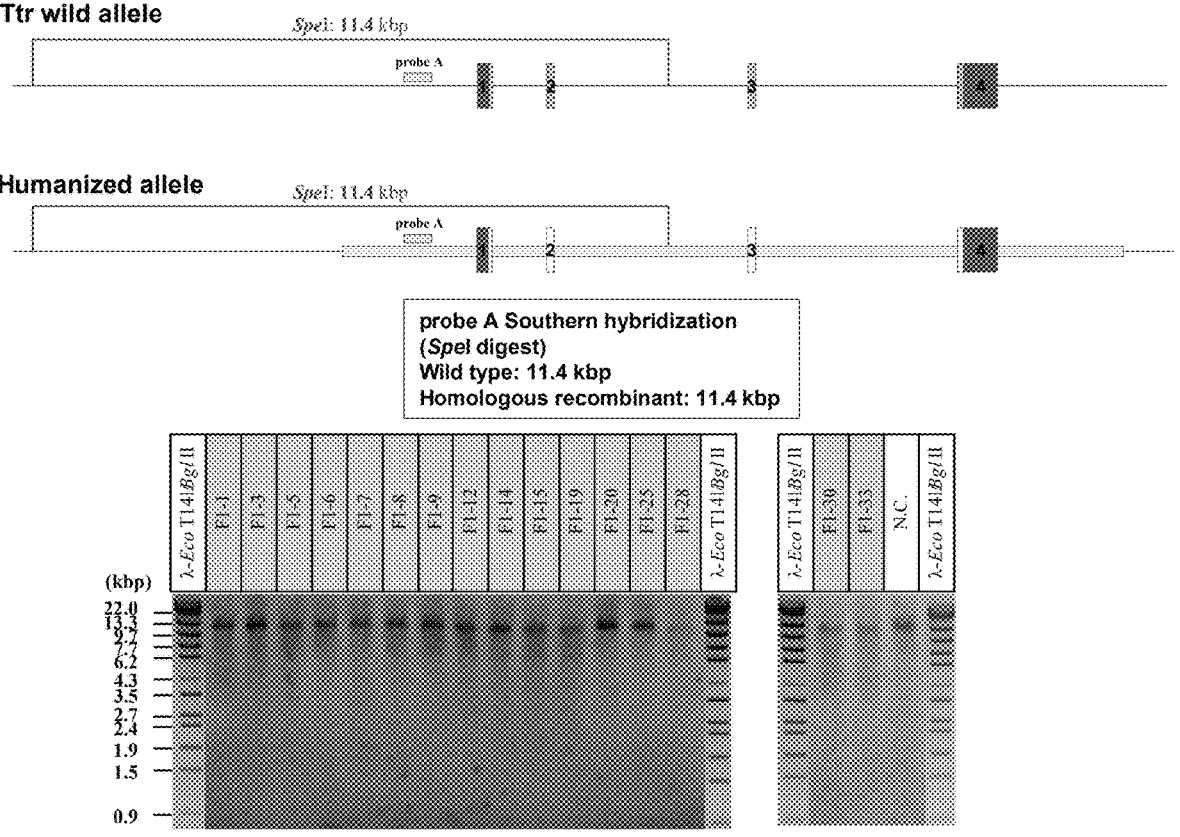
FIG. 16 is a diagram showing Southern blot analysis on the 5'-side.
Figure 17:
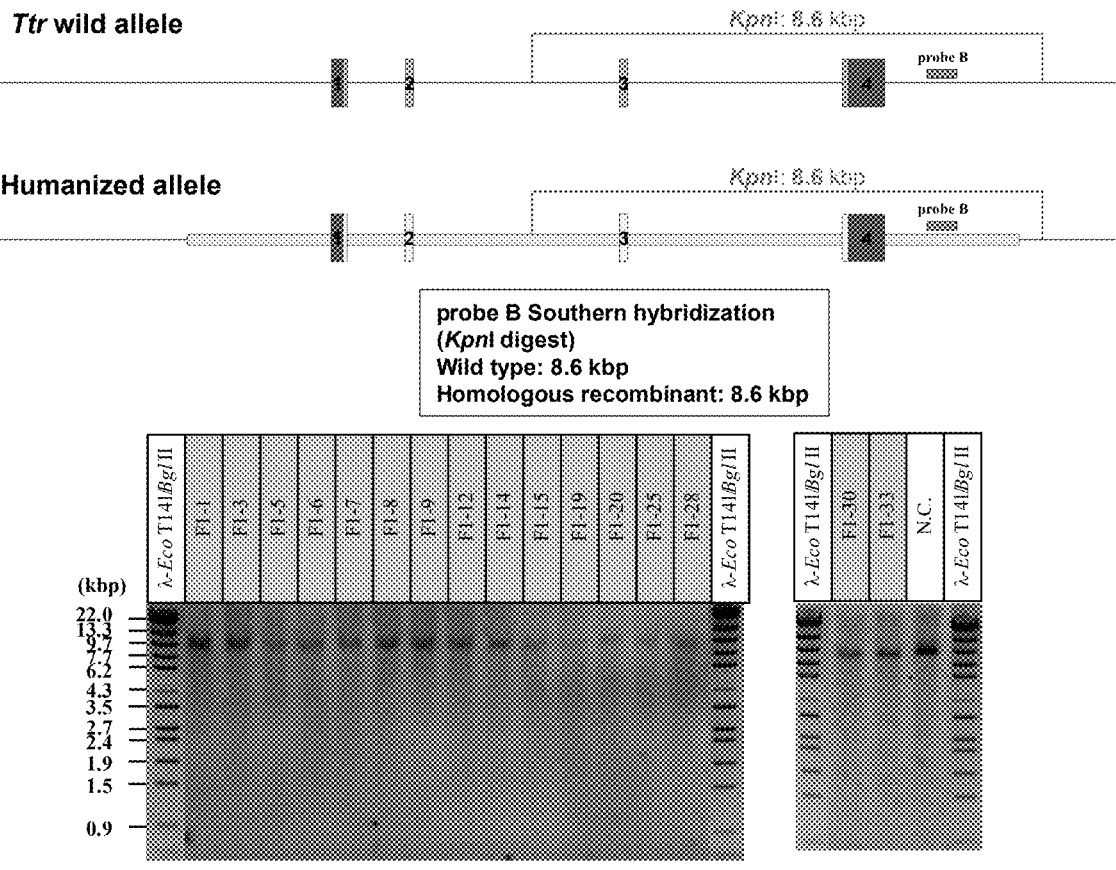
FIG. 17 is a diagram showing Southern blot analysis on the 3'-side.

Moreover, to analyze the presence or absence of a large genomic defect which cannot be analyzed only by sequencing, the 16 pups in which all the exons had been humanized were analyzed by Southern blot hybridization. As a result of this analysis, only the expected DNA fragments (11.4 kb for 5' probe and 8.6 kb for 3'-side) were detected at both 5'-side (FIG. 16) and 3'-side (FIG. 17) upon digestion with the respective restriction enzymes. Based on the above results, these 16 F1 mice (♂ 8 and ♀ 8) were determined to be heterozygous. The analysis results obtained are summarized in Table 4.

TABLE 4

| Clone | Number of pups | Number of pups analyzed | | Number of heterozygous pups | |
|---|---|---|---|---|---|
| No. | born | ♂ | ♀ | ♂ | ♀ |
| a6221 | 4 | 4 | 0 | 2 | 0 |
| a6221 | 6 | 2 | 4 | 1 | 4 |
| a6221 | 9 | 5 | 4 | 2 | 2 |
| a6221 | 8 | 4 | 4 | 1 | 1 |
| a6221 | 7 | 5 | 2 | 2 | 1 |
| Total | 34 | 20 | 14 | 8 | 8 |

Evaluation of exon-humanized mouse (Ttr$^{hTTRexon}$)

The expression of the exon-humanized gene can be confirmed by the following items alone or in combination as appropriate.

The expression of the exon-humanized gene was analyzed for tissue specificity by Northern blotting with RNAs extracted from various organs and tissues. From wild-type (Ttr$^{+/+}$) and TTR gene exon-humanized (Tt$^{rhTTRexon/hTTRexon}$) mice at 12 weeks of age after birth, the brain, eyeball, heart, lung, liver, kidney, spleen and skeletal muscle were excised, and RNAs were then extracted to prepare total RNA in an amount of 2 μg or 10 μg for each organ. To the total RNA, an equal amount of Northern-Max®-Gly Sample Loading Dye (Thermo Fisher Scientific Inc., #AM8551) was added and mixed, followed by electrophoresis on a 1% formalin-denatured gel. After electrophoresis, the gel was transferred onto a nylon membrane by capillary blotting with 20×SSC. After blotting, the membrane was air-dried and RNAs were fixed on the membrane with a UV crosslinker. The membrane obtained with 2 μg RNA was decided for use in beta-actin probing, while the membrane obtained with 10 g RNA was decided for use in Ttr probing.

Figure 18:
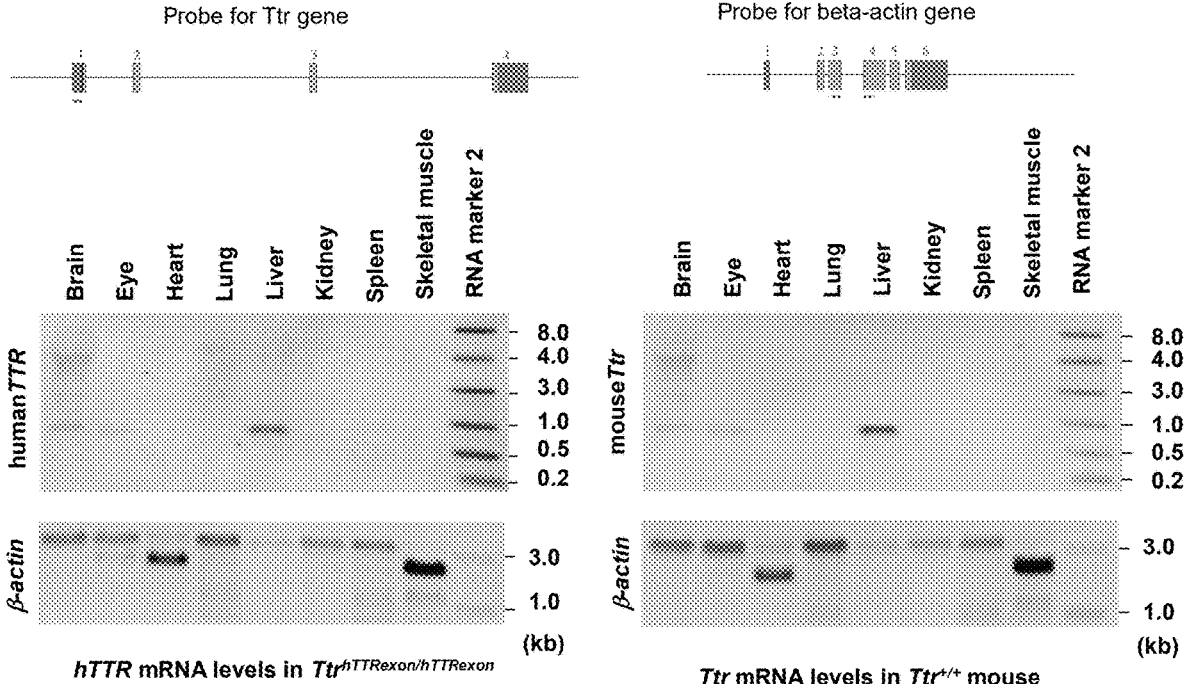
FIG. 18 is a diagram showing the analysis for tissue specificity of expression.

To detect mouse Ttr in the wild-type mouse and human TTR in the TTR gene exon-humanized mouse by Northern blotting, a Ttr probe was designed in 5'UTR, which is a sequence common to both (FIG. 18, top left panel). A probe for detecting the Ttr gene was prepared as follows: wild-type mouse cDNA was used as a template for PCR with primers Ttr-5'UTR-F1 (5'-CTA ATC TCC CTA GGC AAG GTT CAT A-3' (SEQ ID NO: 39)) and Ttr-5'UTR-R2 (5'-AAG CCA TCC TGT CAG GAG CTT GTG G-3' (SEQ ID NO: 40)), and the amplified 196 bp fragment was purified. After purification of the fragment, an AlkPhos Direct Labelling and Detection System (GE Healthcare) was used to label the probe in accordance with the protocol attached to the kit. This labeled Ttr probe was used for hybridization at 55° C. for 18 hours with the membrane obtained when 10 μg RNA extracted from the wild-type mouse liver was electrophoresed and then blotted. As a result, specific signals were detected in the brain, eye and liver in the Ttr$_{hTTRexon/hTTRexon}$ and Ttr$^{+/+}$ mice (FIG. 18, middle panel). The exon-humanized gene showed the same expression pattern for the mouse endogenous Ttr gene.

As an internal control, hybridization was conducted using beta-actin as a probe. The position of the beta-actin probe is shown in the top right panel of FIG. 18. Mouse liver cDNA was used as a template for PCR with primers 5'-GGT CAG AAG GAC TCC TAT GTG GG-3' (SEQ ID NO: 41) and 5'-ATG AGG TAG TCT GTC AGG TC-3' (SEQ ID NO: 42), and the amplified fragment was cloned into pBluescript SK. The probe DNA was excised from the plasmid with restriction enzymes and then labeled in the same manner as used for preparation of the Ttr probe, followed by hybridization at 55° C. for 18 hours. As a result, the same pattern was detected in the exon-humanized mouse and the wild-type mouse (FIG. 18, bottom panel).

The TTR protein is produced in the liver and secreted into the blood. For this reason, its expression level can be precisely analyzed by measuring blood TTR. For this purpose, ELISA (Enzyme-Linked Immuno Sorbent Assay) or Western blotting is used, but human TTR was measured with a commercially available ELISA assay kit.

For measurement of human TTR concentration by ELISA, the following ELISA kit for TTR measurement, i.e., Human Prealbumin (Transthyretin, TTR) ELISA kit (manufacturer, catalog #: AssayPro, EP3010-1) was used to measure the human TTR concentration in the sera of Ttr$^{hTTRexon/hTTRexon}$ female and male (five each) mice at 12 weeks of age after birth.

Figure 19:
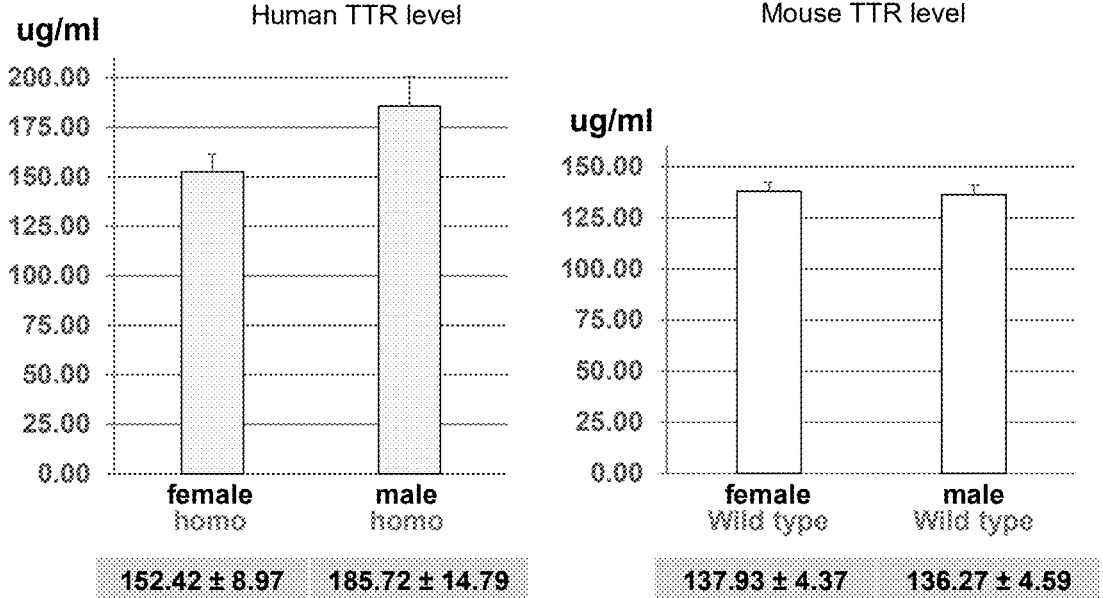
FIG. 19 is a diagram showing the blood levels of human TTR and mouse TTR.

The measured concentration of each analyte was determined from the calibration curve (31.25, 7.81, 1.95, 0.49, 0.12, 0 ng/ml) obtained with the reference standard attached to the kit. The serum concentration of each analyte was calculated from its measured concentration by correction with the dilution factor. As a result, the human TTR concentration was 152.42±8.97 μg/ml in the Ttr$_{hTTRexon/hTTRexon}$ female mice and 185.72±14.79 μg/ml in the Ttr$_{hTTRexon/hTTRexon}$ male mice (FIG. 19, left panel).

Mouse TTR was measured by Western blotting. The sera of wild-type Ttr$^{+/+}$ mice at 12 weeks of age after birth were used and measured for their mouse TTR concentration by Western blot analysis. As an antibody for detection of mouse TTR, anti-TTR antibody (Proteintech, 11891-1-AP) was used, and recombinant mouse TTR (mTTR: LifeSpan Bio-Sciences, LS-G12719) was used for preparation of a calibration curve. As a result, the mouse TTR concentration was $137.93\pm4.37$ μg/ml in the $Ttr^{+/+}$ female mice and $136.27\pm4.59$ μg/ml in the $Ttr^{+/+}$ male mice (FIG. 19, right panel). In view of the foregoing, human TTR levels in $Ttr^{hTTRexon/hTTRexon}$ mice were found to be almost the same as mouse TTR levels.

Example 2

Production of homozygous mouse $(Ttr^{hV30exon/hV30exon})$ from wild-type exon-humanized heterozygous mouse $(Ttr_{+/hV30exon})$ When crossing the established wild-type exon-humanized heterozygous mice $(Ttr^{+/hV30exon})$, many wild-type exon-humanized homozygous mice $(Ttr_{hV30exon/hV30exon})$ can be obtained.

Figure 20:
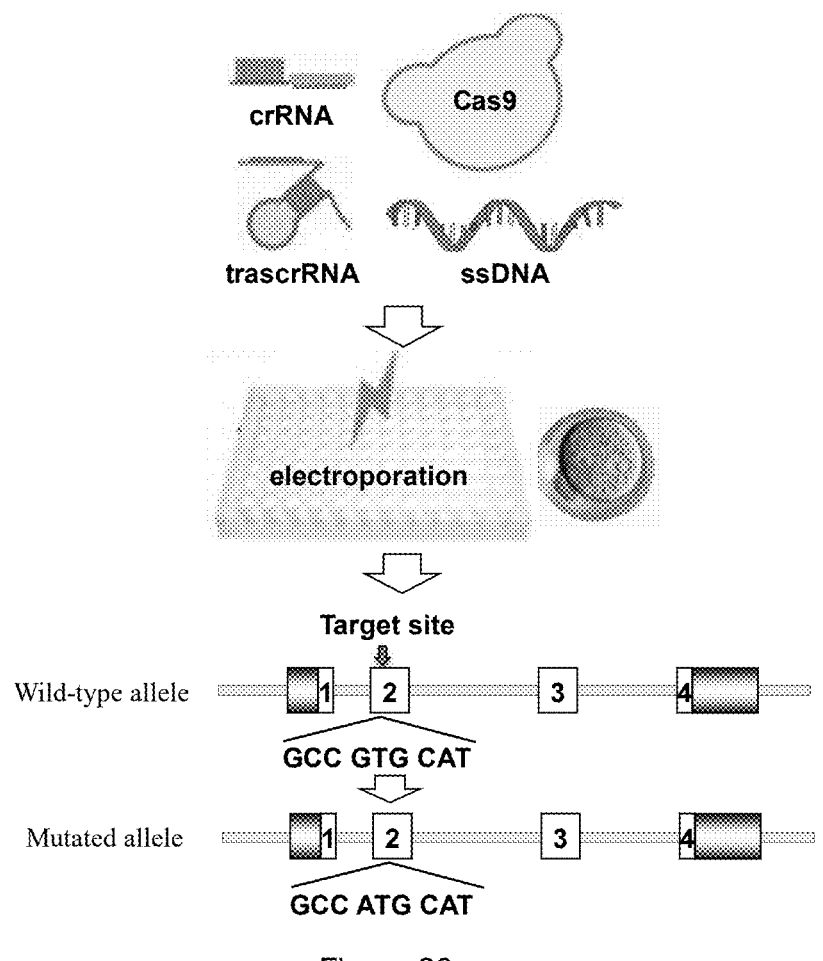
FIG. 20 is a diagram showing how to produce a mouse having a mutated allele.

Production of Mutated Exon-Humanized Heterozygous Mouse $(Ttr^{hV30exon/hM30exon})$ from $Ttr^{hV30exon/hV30exon}$ Mouse Ova obtained upon superovulation of female $Ttr^{hV30exon/hV30exon}$ mice and sperms from male $Ttr^{hV30exon/hV30exo}$ mice are used for in vitro fertilization to obtain many $Ttr^{hV30exon/hV30exon}$ fertilized eggs. These fertilized eggs are injected with crRNA, tracrRNA, Cas9 mRNA and single strand DNA (ssDNA) by electroporation which has already been established (FIG. 20). The sequences of crRNA, tracrRNA and ssDNA are shown in FIG. 21 (SEQ ID NOs: 43 to 47). In the injected fertilized eggs, homologous recombination occurs between the donor oligo and the human TTR gene on the genome to replace GTG at position 30 with ATG. At the stage of two-cell embryos, they are transplanted into the oviducts of foster mothers to obtain pups. The born mice are genotyped to select $Ttr^{hV30exon/hM30exon}$ mice heterozygous in having wild-type and mutated exons.

Increased Production of $Ttr^{hM30exon/hM30exon}$ and $Ttr^{hV30exon/hM30exon}$ Mice from $Ttr^{hV30exon/hM30exon}$ Mouse Simply when crossing the $Ttr^{hV30exon/hM30exon}$ mice obtained above, only ½ of their pups will be $Ttr^{hV30exon/hM30exon}$ mice, and the efficiency is low in this case. For this reason, $Ttr_{hV30exon/hM30exon}$ mice are first crossed to obtain many $Ttr_{hM30exon/hM30exon}$ mice. Then, ova and sperms from $Ttr^{hV30exon/hv30exon}$ and $Ttr_{hM30exon/hM30exon}$ mice are used to conduct in vitro fertilization, as a result of which all pups will have the $Ttr^{hV30exon/hM30exon}$ genotype. This allows increased production of $Ttr^{hV30exon/hM30exon}$ mice. The thus obtained $Ttr^{hV30exon/hM30exon}$ mice have the same genotype as human patients, and can be used for the gene therapy experiments described later.

Example 3

Simultaneous disruption of human wild-type TTR gene (TTRVal30) and human mutated TTR gene (TTRMet30)

$Ttr_{hV30exon/hM30exon}$ mice can be used to conduct an experiment in which the wild-type and mutated genes are both disrupted, and an experiment in which only the mutated gene is disrupted. First, the former will be described.

The CRISPR/Cas9 system is used to disrupt the TTR gene in the liver of $Ttr^{hV30exon/hM30exon}$ mice. To completely suppress gene expression, it is most reliable to disrupt the translation initiation codon ATG. For this purpose, the website CCTop (https://crispr.cos.uni-heidelberg.de) on the internet was used to search for target sequences. Since double-strand cleavage is deemed to occur at 3 bp upstream of the PAM sequence (Jinek et al. Science 337:816-821, 2012), the following sequence containing ATG, i.e., TCCACTCATTCTTGGCAGGA(TGG) (SEQ ID NO: 48; TGG at the right end serves as a PAM sequence, and the underlined part is ATG) was found to be the best sequence.

Figure 22:
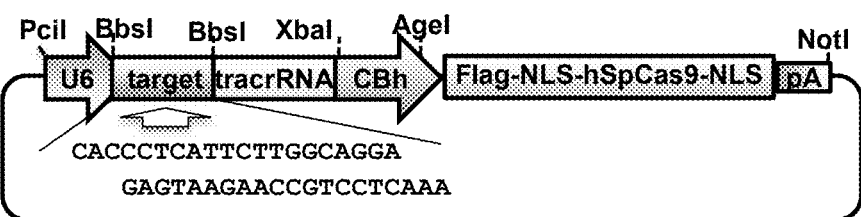
FIG. 22 is a diagram showing pX330-ATG.

This cleavage activity can be evaluated by the method of Mashiko et al. which has already been mentioned above (Mashiko et al. Sci. Rep. 3: 3355, 2013). An approximately 0.5 kb to 1.0 kb gene fragment containing a target sequence near its center is introduced into the multicloning site of plasmid pCAG-EGxxFP (available from Addgene). pCAG-EGxxFP contains the N-terminal and C-terminal sequences of the EGFP gene, which share an approximately 500 bp sequence, and is structured such that a target sequence (0.5 to 1.0 kb) is flanked by these N-terminal and C-terminal sequences. pCAG-EGxxFP carrying the target sequence and pX330 carrying the guide RNA sequence are co-transfected into HEK293 cells. In the HEK293 cells, gRNA and CAS9 are expressed and bind to the target sequence in pCAG-EGxxFP to cause double-strand cleavage. Then, gene homologous recombination or single strand annealing occurs in the region shared between the N-terminal EGFP sequence and the C-terminal EGFP sequence to cause recombination as the full EGFP sequence, so that EGFP is expressed and green fluorescence is emitted. Namely, upon comparison of the number of green fluorescence-emitting cells, cleavage activity on each target sequence can be relatively evaluated, whereby the most efficient target sequence can be determined. The sequences mentioned above were integrated into pX330 to prepare pX330-ATG (FIG. 22). In FIG. 22, the target sequence of Cas9 is shown in SEQ ID NO: 49, and the sequence comprising "cacc" at the 5'-side and "caaa" at the 3'-side of the target sequence is shown in SEQ ID NO: 50.

Delivery of pX330-ATG into the Liver $Ttr^{hV30econ/hM30exon}$ mice at around 6 weeks of age are each injected through the tail vein with a solution containing 50 μg of pX330-ATG in a volume of 2 ml (1/10 volume of mouse body weight which is assumed to be 20 g) within 5 to 7 seconds (hydrodynamic gene delivery: Lewis et al. Nat. Genet. 32: 107-108, 2002). This technique allows pX330-ATG to be introduced into up to 80% of liver cells.

Evaluation of TTR Gene Disruption

The degree of TTR gene disruption in the liver can be evaluated in the following manner.

(1) DNA analysis of the liver: The liver is partially excised at around 8 weeks of age. DNA is extracted, a nucleotide sequence around ATG is analyzed, and remaining wild-type TTR, mutated TTR and the frequency of insertion or deletion mutation are analyzed.

(2) Blood TTR level: Human TTR in serum is measured by ELISA assay at 3 months of age, 6 months of age, 12 months of age, 18 months of age and 24 months of age. Blood level measurement also makes it possible to predict what degree of TTR gene disruption has occurred. The results obtained are compared with the analysis data of DNA.

(3) Analysis of non-fibrillar TTR deposits: Prior to amyloid deposits, non-fibrillar TTR deposits are observed at the earliest at around 1 month of age, and amyloid deposits appear at the earliest from one year after birth. Thus, autopsy is conducted at 3 months of age, 6 months of age, 12 months of age, 18 months of age and 24 months of age (10 mice for each group, if possible) to excise the digestive tract, kidney, heart, sciatic nerve and spleen, which are then fixed and prepared into tissue sections. These sections are used for immunostaining with anti-TTR antibody and anti-serum amyloid A (SAA) antibody. The use of anti-SAA antibody allows analysis of amyloid deposits associated with inflammation, etc., and thereby allows differential diagnosis. In addition, Congo red staining will further be conducted to analyze amyloid deposits.

(4) Taking all the above data into consideration, the correlation of the percentage of disrupted TTR gene with blood TTR levels or with non-fibrillar TTR levels is analyzed to clarify the possibility of gene disruption therapy.

Example 4

Disruption of Only Human Mutated TTR Gene (TTRMet30)

Ttr$^{hV30exon/hM30exon}$ mice can be used to conduct an experiment in which only the mutated gene is disrupted.

Figure 23:
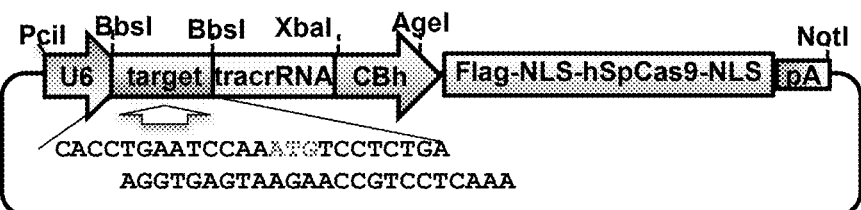
FIG. 23 is a diagram showing pX330-Met30.

The CRISPR/Cas9 system is used to disrupt the TTR gene in the liver of Ttr$^{hV30exon/hM30exon}$ mice. To disrupt only the mutated gene, only those having ATG which encodes methionine as the amino acid at position 30 are disrupted. For this purpose, the website CCTop (https://crispr.cos.uni-heidelberg.de) on the internet was used to search for target sequences. Since double-strand cleavage is deemed to occur at 3 bp upstream of the PAM sequence (Jinek et al. Science 337:816-821, 2012), the following sequence containing ATG, i.e., TCCACTCATTCTTGGCAGGA(TGG) (SEQ ID NO: 48; TGG at the right end serves as a PAM sequence, and the underlined part is ATG) was found to be the best sequence (FIG. 23). In FIG. 23, the target sequence of Cas9 is shown in SEQ ID NO: 51, and the sequence comprising "cacc" at the 5'-side and "caaa" at the 3'-side of the target sequence is shown in SEQ ID NO: 52. This cleavage activity can be evaluated by the method of Mashiko et al. which has already been mentioned above (Mashiko et al. Sci. Rep. 3: 3355, 2013).

Delivery of pX330-MET30 into the Liver

Ttr$^{hV30exon/hM30exon}$ mice at around 6 weeks of age are each injected through the tail vein with a solution containing 50 μg of pX330-ATG in a volume of 2 ml (¹⁄₁₀ volume of mouse body weight which is assumed to be 20 g) within 5 to 7 seconds (hydrodynamic gene delivery: Lewin et al. Nat. Genet. 32: 107-108, 2002). This technique allows pS330-ATG to be introduced into up to 80% of liver cells.

Evaluation of TTR Gene Disruption

The degree of TTR gene disruption in the liver can be evaluated in the following manner.

(1) DNA analysis of the liver: The liver is partially excised at around 8 weeks of age. DNA is extracted, a nucleotide sequence around ATG at position 30 is analyzed, and remaining wild-type TTR, mutated TTR and the frequency of insertion or deletion mutation are analyzed.

(2) Blood TTR level: Human TTR in serum is measured by ELISA assay at 3 months of age, 6 months of age, 12 months of age, 18 months of age and 24 months of age. Blood level measurement also makes it possible to predict what degree of TTR gene disruption has occurred. The results obtained are compared with the analysis data of DNA.

(3) Analysis of non-fibrillar TTR deposits: Prior to amyloid deposits, non-fibrillar TTR deposits are observed at the earliest at around 1 month of age, and amyloid deposits appear at the earliest from one year after birth. Thus, autopsy is conducted at 3 months of age, 6 months of age, 12 months of age, 18 months of age and 24 months of age (10 mice for each group, if possible) to excise the digestive tract, kidney, heart, sciatic nerve and spleen, which are then fixed and prepared into tissue sections. These sections are used for immunostaining with anti-TTR antibody and anti-serum amyloid A (SAA) antibody. The use of anti-SAA antibody allows analysis of amyloid deposits associated with inflammation, etc., and thereby allows differential diagnosis. In addition, red staining will further be conducted to analyze amyloid deposits.

(4) Taking all the above data into consideration, the correlation of the percentage of disrupted TTR gene with blood TTR levels or with non-fibrillar TTR levels is analyzed to clarify the possibility of gene disruption therapy.

INDUSTRIAL APPLICABILITY

The present invention provides an exon-humanized TTR gene in which exons in the Ttr gene have been humanized, an ES cell engineered to carry the same, and an exon-humanized mouse derived from the ES cell. A mutation in the human TTR gene causes familial amyloid polyneuropathy, which is a dominant hereditary disease. The mouse of the present invention can be used to prepare a human disease model mouse by introducing a mutation into the human TTR gene. This mouse can be used to conduct a so-called gene therapy experiment in which the human TTR gene is disrupted in the liver, and thus allows non-clinical trials for study of therapeutic efficacy.

SEQUENCE LISTING FREE TEXT

SEQ ID NO: 1: synthetic DNA
SEQ ID NO: 2: synthetic DNA
SEQ ID NOs: 12 to 24: synthetic DNAs
SEQ ID NOs: 29 to 31: synthetic DNAs
SEQ ID NOs: 34 to 36: synthetic DNAs
SEQ ID NOs: 39 to 44: synthetic DNAs
SEQ ID NO: 45: synthetic DNA/RNA
SEQ ID NO: 46: synthetic RNA
SEQ ID NOs: 47 to 52: synthetic DNAs

The invention claimed is:

1. A donor vector comprising a fragment of a target gene, wherein the fragment of the target gene comprises four exons and three introns, wherein the four exons are human nucleotide sequences of the target gene as set forth in SEQ ID NOs: 4, 6, 8, and 10, and the three introns are mouse nucleotide sequences as set forth in SEQ ID NOs: 5, 7, 9 wherein the target gene is a transthyretin gene, wherein the four exons and the three introns are arranged in the follow-ing order; Exon 1 as set forth in SEQ ID NO: 4, Intron 1 as set forth in SEQ ID NO:5, Exon 2 as set forth in SEQ ID NO:6, Intron 2 as set forth in SEQ ID NO:7, Exon 3 as set forth in SEQ ID NO:8, Intron 3 as set forth in SEQ ID NO:9, and Exon 4 as set forth in SEQ ID NO: 10.

2. A method for producing an exon-humanized mouse comprising exons in a mouse transthyretin gene replaced with exons in a human transthyretin gene, which comprises:

(a) introducing the donor vector according to claim 1 and a first vector comprising a guide RNA comprising a target sequence complementary to a site immediately upstream of Exon 1 in the transthyretin gene, tracrRNA, and DNA encoding a DNA-cleaving CRISPR-Cas enzyme and a second vector comprising a guide RNA comprising a target sequence complementary to a site immediately downstream of Exon 4 in the transthyretin gene, tracrRNA, and DNA encoding a DNA-cleaving CRISPR-Cas enzyme into mouse embryonic stem(ES) cells; wherein the Cas enzyme cleaves the sites immediately upstream of the Exon 1 and immediately downstream of the Exon 4 and the donor vector replaces the exons in the mouse transthyretin gene with exons in the human transthyretin gene through recombination;

(b) creating chimeric embryos from the ES cells obtained in the step (a) and transplanting the chimeric embryos into foster mothers to thereby create chimeric mice; and (c) selecting a male mouse and a female mouse from among the chimeric mice obtained in the step (b) and crossing them to produce pups.

3. The donor vector according to claim 1, wherein the donor vector, when introduced into mouse ES cells, expresses transthyretin that is encoded by said exons.

4. The method according to claim 2, wherein the donor vector, when introduced into said mouse ES cells, expresses said transthyretin that is encoded by said exons.

5. The donor vector according to claim 1, wherein the donor vector, when introduced into mouse ES cells, expresses said transthyretin that is encoded by said exons in a normal expression level and a normal tissue-specific expression pattern when expressed in a mouse.

6. The method according to claim 4, wherein the donor vector, when introduced into said mouse ES cells, expresses said transthyretin that is encoded by said exons in a normal expression level and a normal tissue-specific expression pattern in the mouse.

\* \* \* \* \*

SEQUENCE LISTING

<160> NUMBER OF SEQ ID NOS: 52

<210> SEQ ID NO 1
<211> LENGTH: 16913
<212> TYPE: DNA
<213> ORGANISM: Artificial
<220> FEATURE:
<223> OTHER INFORMATION: Synthetic DNA

<400> SEQUENCE: 1

-continued

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tgggtaccgg     660
gccccccctc gaggtcgacc ctccaggtct tatccacctc aaggggagct aacaaaattg     720
aattctttga cctgcaaaga ttcagagccc caaacactgc tatttctctt ctcctaactc     780
ccttaccagg aggcttagtg caagcatttg gcccacctag tccccttcct gctaatcagc     840
ttactgcact agcattagcg agcattccag ggcctacaaa ctgctggcta ggtgtttgtt     900
tggaccttca gaaacaaat gaagagattg tttaggagat gaaagatgt attgaacgag     960 gttgtacatt ttaagggaga aggccgagaa gactctctaa tcaagagcca gccagggttg    1020
ttcattaact accataaatt tggtagtagg gagagagatg tggtcagtaa ctcaatctct    1080
cattcaccta aatgaaacat gtaagctatg gcaccgcagc caggatgtga agaaaaccag    1140
taaagggcta agcaaagaca cctccttcta acttaaacac tacctccaac acccttatgt    1200
tctctaggta gttgctgtta gtattacccc agaacaggca atgtcttcag cagaagcccc    1260
acaaaggcgg tgaattttga cacaagtcca tccctcatca tggattcctg taaccatcct    1320
ctgagaagag ttttttacaat ttcaactcaa tatgtgaaac cacaccttcc tttctttaga    1380
aaagtatgat tgattatcca tgggacctat tcacagcaca aagtgactca aaggcaaaaa    1440
gcacttgggc ttctctgggg ggcaactgcc ctttatctca cacccatgtc ttggacaaca    1500 aatgtttttct tactctgtct gttttttctg tcctgctctg tcacataaaa tcctgcccga    1560
cctttgactc aaactccaga cagtctacct gctgatcgcc cggcccctgt tcaaacatgt    1620
cctaatactc tgtctctgca agggtcatca gtagttttcc atcttactca acatcctccc    1680
agtgcttcaa agcacctcac tttatcttca catccttgtc tctttctaat taaagtttaa    1740
aaagttggtt tctaaggctg atggaggtct aaaaaacaag caaatcaaag acctgagggt    1800
gttctaattt acttggtagt tggtcagaac taccagtatg ttatggtcag agataaatta    1860
gggatactat acttagatca aaatttataa aaagacagag tagagaggat ctctgtgagt    1920
tcaaggttag cctggtcttc gtgcagcgag ctccaggcta gccaaaggta caaaatgaga    1980
ttctgtccct aaacagcaaa ccaaaaacta aataaaattg ataaatgagc atagttcatt    2040
atgatgaatg ctctttactt gtgttagaca cagggttggg tgaggcatca cagtgataac    2100
agttacagat gcacttaggg tatgacactg cctgcagagc acatttgtca aggaagacta    2160
aagccttctg gccatgtcct cagggtttac atgaccttat ctgaaatgtg tctccagttc    2220
aattatctgg aatgtgtgtc tgcttcagtg cctcacattg gtagagaaac attgaccagt    2280
gggaggaagc cagacaacaa agtcctggga agagaggatt ccaggtcctg tgtctgacga    2340
```

-continued

```
ggaatctctc aaagaggtgg gcatgcttat ttagcaaaag aaaatatgct gtcagaagac      2400
cagtaatcat aacaaattta taaagaggct gcgctttgtc atggatcgag aatatgggat      2460
gtacattaaa aacacacaga caatcagacg taccagtagt catgtaatct ggcttcagag      2520
tgggagagaa gtcaggaaac cgagatgtcc caacatggga ccccatagat tattttcatg      2580
tgaatgtaag gcaactgctg tcatcttcca gtttctcaag acaagccaaa gtccaggttt      2640
taatgcaacg tggttcaatt tgcaattttt gcagatattt caaaatccta gagaaatggt      2700
agagcctgtg gtcaggtggc agtccagctt tgccagttta cgagatcctg ggaggcaatt      2760
cttagtttca atggattgtg gagttcagta gtgtggagtt gacatgtgtg ggtgagagat      2820
tttactggat agtgattcct gtatgaagag ggctttccat cacattctga gcaatggaaa      2880
gtaatgatgt caaccttggt tgacaatgca caagagattc tggagaaagc atctccttct      2940
taggcacaga tattgaatgg aatcatctga catttgtatt ttccagttta taaaatgcct      3000
ttatatcttg tcacatttaa agttcttaga aaatctcctt caaagagaaa tgcgatattt      3060
ctgatttaca aatgtgtggt ctgatatctg agataggaaa tcatttccag aagcaagcag      3120
gacattgagt agcagatctg ggattgggtg tgtcagagcc tccaacactg tcagactcaa      3180
aggtgcagga caataagtag tcttactctg gctgtatctt ctcattgttg cttttggacg      3240
gttgccctct ttcccaaagg tgtctgtctg cacatttcgt agagcgagtg ttccgatact      3300
ctaatctccc taggcaaggt tcatatttgt gtaggttact tattctcctt ttgttgacta      3360
agtcaataat cagaatcagc aggtttggag tcagcttggc agggatcagc agcctgggtt      3420
ggaaggaggg ggtataaaag ccccttcacc aggagaagcc gtcacacaga tccacaagct      3480
cctgacagga tggcttctca tcgtctgctc ctcctctgcc ttgctggact ggtatttgtg      3540
tctgaggctg gccctacggt gagtgatcct gtgagcgatc cagacatggc agttagacct      3600
tagataaaga agaagtgcct tcttccagat gtgagaacta gagtactcag actctatatt      3660
taccattaga ctccaaagag aagagctgga gtgcctctgg ctcttccttc tattgcttta      3720
gcgcattggg tctgtagtgc tcagtctctg gtgtccttag ataataaaga tatgagatta      3780
acatagaaat aaagatataa aagggctgga tgtatagttt agtggtccag tgtatgccta      3840
gtatgtgaaa agccttctgt tcaacctcta gcaatagaaa aacaagatat attctcggtg      3900
gggctgttaa tattgaattc tcataaaatc tttaatatat ttagtatgcc tattatgttg      3960
ttatatttta gttctttagc taatcaaaat gcattattga tctttctttg tctttttttg      4020
gccaacactc tattccagtc tttgaaaaag tcctttaaaa gagttaatca gtataattaa      4080
atgagtcagg aagtatgtga gggttatttt acaaccagag ggaattacta tagcaacagc      4140
tgattagaat gatctcaaga aaaagcccat tctgtctttt tgcaccatgc acctttcagt      4200
ggctccattc agatggagag gcaaacagag caatggctct cagagggcct attttccctt      4260
tgaacattca ttatccatat ccctggtgca cagcagtgca tctgggggca gaaactgttc      4320
ttgctttgga aacaatgctg tctatgtcat actggataaa gaagctcatt aattgtcaac      4380
acttatgtta tcataatggg atcagcatgt acttttggtt ttgttccaga gtctatcacc      4440
ggaaagaaca agccggttta ctctgaccca tttcactgac atttctcttg tctcctctgt      4500
gcccagggca ccggtgaatc caagtgtcct ctgatggtca aagttctaga tgctgtccga      4560
ggcagtcctg ccatcaatgt ggccgtgcat gtgttcagaa aggctgctga tgacacctgg      4620
gagccatttg cctctgggta agcttgtaga aagcccacca tgggaccggt tccaggttcc      4680
catttgctct tattcgtgtt agattcagac acacacaact taccagctag agggctcaga      4740
```

```
gagagggctc aggggcgaag ggcacgtatt gctcttgtaa gagacacagg tttaattcct      4800
agcaccagaa tggcagctca taaccatctg aaactcacag tcttaggaga tctgggtatc      4860
tgacattctc ttctacccac catgtgtgtg gtgcacaaat tcacatgcag gcatcaaatc      4920
ttataaacaa caacaaaaaa ccaacaaacc tggtagcaaa agaagattag aaggttaaac      4980
atatgagccg agagcttttg ttttgttttg ttttgttttg ttttgtttac atttcaaatg      5040
ttatcccctt tctcggtccc cctccccaaa ccctctaccc cattctctcc tcccttctt       5100 ctatgagggt gttccccacc aacccactcc caccttcctg ctctcgaatt ccctatact        5160 gggacatcaa gccttcacag aatcaagggc ctctcctccc attgatgccc gacaatgtca      5220
tcctctgcta cctatgtggc tggagccatg ggtcccttca tgtatcctcc ttggttggtg      5280
gtttagtctc tgggaggtct gggggatctg gttgattgat attattgttc ttcctatgag      5340
attgcaaacc ccttcagctc cttcggtcct ttaactcctc cactggggac cccgagctca      5400
gtccaatggt tggctgtgag catccaccag cagaggcctt ttttttttt tttaacaaag      5460 ctgctttatt atgttgctta gagcatgacc aggaaccaga gcacagtcca agactgaagg      5520
gaggaaaagg gggggagtca ataacccac tgtttcatag tggtttgcaa ccctttata        5580 tcacagccca ctttaggcaa ataatgaaaa ttatagtctc cagggacaga gaagatggtg      5640
caggaagtga agtgcctgct cagaaaatgg gggcttgaat gtgagttccc agactctgtg      5700
taagatgccc agcatcgaag tgcatgctta taacaccagc ctggaggtag aagcttagaa      5760
acaggggtac cctgaagttg cttgttcacc agtgtccctg aatgggtagg tgcatgtttg      5820
gtgagagacc ctgtctcaaa aatcaaggtg taggataatt gaaaatacct agctttgagc      5880
ttagatcatg caaatgtgta cacacactca cacacaccac acacacaaaa aaatgcagag      5940
acagagagat acagagagac agagagatac agagacagag acagagagaa aaggagaaag      6000
taaaaaacaa ataatttaaa gacccatggc cacaaagagg ctcaaagaca agcacgtata      6060
aaaccataca catgtaattt taggagtttt cagattccct ggtacccgtg ggtgatgcac      6120
aagctttgaa tcccagtctt aaaatcttac gaagaacgtg ttcgtgtgtg ctaatttatt      6180
gatgagagga aaggaattga caaagtgccc ttccggagct tcctgcatta cccagactca      6240
gggttttttt aaatgtacac tcagaacaga gtagctctgt gcaagggtag caaccacgaa      6300
gcttaataag aaacatatcg tgagagatct gcaaggcaaa tctaggggct gaccaatctc      6360
acagtcaccc actagcatgt caacacaact tcccacctgt gctagccact tagcaatttt      6420
gtgttgttct gtttttgtttt tgtttttaac aaagcaattt caaagagatt tctaattcat     6480
ctaaacaaac aaaccaaaag gaaaacagca aagacgccct gagcacttag cagagcagct      6540
atgcagttat gactcctggg tggagacttt atatcaggct tcaactgaat acctagaacc      6600
tactagtgct cttcatcaat ccttgggaag gtcattttct tttggtgctg ttttgagttt      6660
ctatttgtta atgtcttcat aattatacac gtgttgagca cagcatgcaa agtgattagg      6720
ggaatctagt tggagtggaa tggatacccca aatattcaga ctttcttgtg actcttcttt      6780
cttgtaccca catcaaaaaa aaaaaaaatg gagatgagac atggtcagag tcactaaaac      6840
cagctgctac ttttaattac gtggggagca gtttctaaca ttgccattat tgaactgatg      6900
ctgcctgggt ggaaatggaa atcacttagt atttcttgtt ggcaaagaat tactgaatgg      6960
attaaatttc caaagggaga agtcagttac aagtctttte tttgtttatt aggctttctg      7020
ctatgataaa ttacactact tccagaagtt acccttaggc catgggacac tggactatca      7080
```

-continued

```
ctctgctgtc acaagagatt acagagttag tcaaggcagc ttgtgacacc ttcagggact    7140
gtcataaact tccagcaagt cattaatcct gaatgcaata ctgtgtgtgt gtgtctatgt    7200
gtgtttgtat gtctgtgtgt gtcttatgtc tgtgtctctg tgtgtgtgtg tgtttgtgtg    7260
tgtgtgtgta tgtatgcctg tgtgtgtctt atgtctgtgt ttgtgtgtct gtgtgtgtct    7320
tatgtctgtg tttgtatgtc tgtgtgtgtc tgtgtgtgtc ttatgtctgt gtctctgtgt    7380
gtgtgtgtgt gtatgtatgt atgtatgtat gtatgtgtat gtgtttgcat ctctctgtgt    7440
gtctgcgctt atatatttgt gtatgtgttt atgtgttcgc ctttgtgcgt tgttgggdat    7500
tgaatccagg ggaatacaaa tgttaagaaa gaacgttacc actaagcttc acctgtaggc    7560
cttaaagctt ttctttcttt taaaaattgt aattaattca ttttcagtca ggatctccac    7620
acctcgtccc tgctgctcta gaactcacta tttaaacaca atcgccctca aacctgcagc    7680
aaccctcccg cctctaccct gcgagcacta gaataataac aggtgacccc acacgcctag    7740
attaagacct ttaaggtaaa cattttacta tattttagtc tcataagaca agatgctaca    7800
ataaagctgt acataaagtt ccctcgaatt tcttgctatt ttaactcaaa cataaggatt    7860
tcctcctttt tgattcaggt aacagaaaaa atacacaggt acatacatgt acacacatga    7920
acacacacgc atcacaacca catatgcgca cgcttgtgtg atctatcatt taccatgcca    7980
ctgaactctt cttcccccat aaaattcctct ggacttgtgt gccctccagg aaaaccagtg    8040
agtctggaga gctgcatggg ctcacaactg aggaggaatt tgtagaaggg atatacaaag    8100
tggaaataga caccaaatct tactggaagg cacttggcat ctcccattc catgagcatg     8160 cagaggtaag tggacacacc aagttgtttg gattttgttt ttagtctcag gaaattccct    8220
tcgctcttgc tgtacgatgg gcatgagtgg aaagtagatt ccacagccag aatccacagt    8280
gctgggaaag caagccttct gaattttct aaaactcatt tagcaacatg gcctgaacct      8340
gttcacactg cttatggtca gctaactata tttatgtaaa tattcatttc tctgttgagg    8400
aaatgttagt atttgctttt gaggcaacct ccagatacca tggagggcat gtcatagtca    8460
aagagagggc tccctatggt atttctctaa attctggcat ttcctttatt ccaaagcaca    8520
tctagtgtcc ccagaagttt gggtagacaa ttcttggcaa cacagagaat tacaacatgt    8580
tcaaaaccca acagcttaat atctaaatca tcaagcaaac atcacatggc aaagggattt    8640
ctgaatcaaa actgtttcat ccttatgatc aacctatgga ggtctagcct cgacttacac    8700
ccattttacc aataagctaa gagaagctaa gttcctcatc aaggacacaa ggctagcatg    8760
tgtgagcaag tgacagagtt gccctctatg ttggttagtg tgccttagcc agtgtctcag    8820
taagaaatgg agctaaatca aaacccaagg ccaacagcca aaggcacatg agtaacctt     8880 gcttggcact gggctcagtt tccctggctc ctctcagtcc tcagttcaca gaggcagctg    8940
tcatgcaaat agaatccaag cttgttggtc agacctggag ataacaaatt ccatcaaaaa    9000
tagctcctca tgtgacctag tttgctgtct gttgctatga tacacaccat gaccgaaaag    9060
caaccctggg gagagaaggg tttatttcat cttacagctt acagttcacc atggaggaaa    9120
gccaggtggg aacctggaag tggaaattga agcagagacc agaaaggaat gctgtttact    9180
ggctggctta gctccttttc ttatacagct taggtctatg tgcccagggg atggtactgc    9240
cgagcatagg ctgagcccgc ctacatcaac cattagtcaa aaaaaggtcc atagacttgc    9300
ctacaggcca atctcatgga ggcaataccc cagtggaggg tccctcttcg caggttactc    9360
tagtttgtgt caagttgaca aaacctaacc acaaagcaca aacagggtct gcccttgtgg    9420
cttagccatg gatgacactc tcagatgatg gtgttaccag acaaaccaga ggggctcacc    9480
```

-continued

```
aagagtctgc cacctaccaa ggtagtactc tactcctcac tgggcaccaa cacccatatt    9540
agctgggcca gtacaggacc cttgctgttt cctgcatgaa ttgtccatag accctgggtc    9600
tcagcctgcc gggagtacct gtaagtagtc gcctcaaaca cattattcct gttggaagac    9660
ttgtctgatt ctcttttaga actcaatcaa caaacgtttt tattttgttt tggctttttg    9720
gagacaagat ctctcatagg ccagcctgac ttgaatgtag ctgaggatga cctgtgctgc    9780
taatcttctc gcctcttcct cccaagtggt aggataatag gcataagaca ccacagcagt    9840
tttactccat accagggctc tgaacccaga ctttaaacac tctatcaact gattcacatt    9900 cccacccat cattcaacaa acatttgaaa aataaaaccc ttctgccttg agcactctgc    9960
taaatacagc ctttgagtgc ggagtatttc ctcacaacca gggtccaaga tgaccccatc    10020
atacatacca cggaaaatta ggagatgttt ttaggtctct ttgcttgggg taattttat    10080 gtgtgtgtgt acacagccct gtgcgtgtgt gtgtgtgtgt gtgtgtgtgt gtacaggcac    10140
acacgtgtat gcatgtagag gctacataaa aaccttaggt gtcattctca ggcactctgt    10200 tcacccttc acacagcccg aacacacaaa atttgaggca ttagcctgga gctcaccagt    10260
taggctagac tgacttgcca gcagacccca ggctgtctcc atctccccag ctctgggatt    10320
acaaactcta tcataccaga cattttttata catattctga gcataaaatt catgtcttca    10380
ggctaacaag tcaagagctt aaatgactga gctctcttac gtggtggatt tttttttaaaa    10440 ctacataata tcttttttttt tttttttcact tctggggaag aaacaaatga gcctgagtga    10500
caatgcgaca gaaaagaaat tttgaggagt gtgtgtgtct gtgtgtgtgg tggcacatgc    10560
ctctcatcta atgctagagg ctacagtaga atgctcctga attagtggcc agccaaggcc    10620
aagggctagg gttgtaactc agtggcagag ggcttgccta gcattcgcag gatttgatcc    10680
atagcgctat aaataataat aaataaatac aacagtctaa gatgattctc cctttcattt    10740
atctggatgt tattttttgtg ttagtttttac tctgtcatcc aatcattgtt tgccctatat    10800
ttggacattt aaaaaaaatc tttattccaa gtgtgttcaa agctgtatcc aaaacctgtc    10860
caccaaatga gtccaatgac atacatcttc tatattacca tctgttccag atttggctga    10920
ctcccggcac ctgggctgtt gctgcaccca tgtctcagat agtctagtga tttgagaagt    10980
gactagtaat tgcaaaatcc agactttgtc cagaaacttc tatgagctcc aaaactttca    11040
tttacatttc tgccagccac aaaccgcttg tgttgtggag agaaccctgt gatgtcttcc    11100
cacagcatct cagccttgtt tcttcccttta aaatattcat cttttcacat tagaacatgc    11160
aaagggacag tgggagcgaa acccctggac tgggacgcac gaagccttcc tttctggtca    11220
ggctctcact gtagaaactt aggccggttt cagcatgcag tctgctggag aatggctcct    11280
gccaacattc caggtctgga agtttgtagt ggagttgttg ataaccactg ttcgccacag    11340
gtcttttgtt tgtgggtgtc agtgtttcta ctctcctgac ttttatctga acccaagaaa    11400
gggaacaata gccttcaagc tctctgtgac tctgatctga ccaggccac ccacactgca    11460 gaaggaaact tgcaaagaga gacctgcaat tctctaagag ctccacacag ctccaaagac    11520
ttaggcagca tattttaatc taattattcg tcccccaacc ccaccccaga ggacagttag    11580
acaataaaag gaagattacc agcttagcat cctgtgaaca ctttgtctgc agctcctacc    11640
tctgggctct gttagaacta gctgtctctc ctctctccta ggtggtattc acagccaacg    11700
actccggccc ccgccgctac accattgccg ccctgctgag cccctactcc tattccacca    11760
cggctgtcgt caccaatccc aaggaatgag agactcagcc caggaggacc aggatcttgc    11820
```

-continued

```
caaagcagta gcatcccatt tgtaccaaaa cagtgttctt gctctataaa ccgtgttagc   11880
agctcaggaa gatgccgtga agcattctta ttaaaccacc tgctatttca ttcaaactgt   11940
gtttcttttt tatttcctca tttttctccc ctgctcctaa aacccaaaat cttctaaaga   12000
attctagaag gtatgcgatc aaactttta aagaaagaaa atactttttg actcatggtt   12060
taaaggcatc ctttccatct tggggaggtc atgggtgctc ctggcaactt gcttgaggaa   12120
gataggtcag aaagcagagt ggaccaaccg ttcaatgttt tacaagcaaa acatacacta   12180
agcatggtct gtagctatta aaagcacaca atctgaaggg ctgtagatgc acagtagtgt   12240
tttcccagag catgttcaaa agccctgggt tcaatcacaa tactgaaaag taggccaaaa   12300
aacattctga aaatgaaata tttgggtttt tttttataac ctttagtgac taaataaaga   12360
caaatctaag agactaactg tggctgctta tatcatgtta atttgggtcc ccaaaattgt   12420
ttgtatgaac atccacactg gtaaataaag ttgtggcacc caatggctgg gcagggtaga   12480
tggaggcagg acttttagat tcctggggga gggagaaaga aggaggaatc accatgccta   12540
gagaaggaga ggagaaacac catgcctgga aaggtgcggg acagagaaca tagccaccat   12600
gtaggagcag gaggatagca gccaaagagg gctgtacgtc tgggtctggg gtggccaaga   12660
gagaatgtag gagttagtaa agtaataact cgggaatatc ggagggaggt ggattagcca   12720
catggaggtt aggaagtggc ccagccattg agctgattaa agcatatcaa aatataaaga   12780
ccctgtgcgt gtgtgtgtgt gtgtgtgtgt gtgtgtgtgt gtgtgtgtgt ttcatttgag   12840
aaccaagaac attcgggcaa gtagtgagga atgagcctca gcaggtggga tctattaaag   12900
tatttaattg ggtatactac aactgattct tcaggcattt cttgttaagc actttactca   12960
tttgagggcc ataacagttt ctttgcacaa gaatgggcct atccgcagtc aggcctggga   13020
ctccgggccc cacccccttgc tgctgagcta tttataatga tacattcagg tagaagggga   13080
gtcatggtct tcagttgtgt gctcactggt gactccacca ggctctgatg gacagttcca   13140
agccaaaatg aagaaacaag ccacaaaacg acatgaatct gggagaaggg ttggtggtaa   13200
cgtgcggagg ggttgggagg tgggaggcag ctaagagatg acaaggaagg gagcatcagc   13260
gtgggctgtg tgcatgcata aaacgaaagc aaacaaaatc aatcactaaa ccatgtttaa   13320
gaacagtgag ttccaaaggg ataaacctgc agcaacccag cttcacttcc caggcaattc   13380
ctaccttccc atcacagttc atagaacata ttcctcctaa actggcaatt ttccttccag   13440
tctttcaaaa tgaaataagc ttggaatcaa ttccacttcc ccagatctct ctacccctct   13500
aatccacttt agaccaattc tacctgaatc agaacccagc tctcaggaga cagaagcaga   13560
gacaggagga tgtccatgag ttcaaggcca ttctagtgag ttctaagcca accaaaacta   13620
cataatgaga ccttgtctaa caacaactta gtcaaatcct aaatccatgt ttaattgata   13680
cacacactca tgcacacgca cacacacgtg taatatgaac aaaacgaaac aaaatagatt   13740
tgtaatggac gagaataaat tcaatttaa ccactctggg tttaatataa tcagactggt   13800
ttttaaactc taaagttggc agtgtgtgca cacacatgtc caacgcatgg aggtgtgtct   13860
caaaaagcat aattataagt attgaactcc tacctgcaac atttgatagc acctgtcaaa   13920
caaggaaatg aagcatatct tttgcctcaa gctatatttt atccaccgag cgctcgtagc   13980
agaggcagaa ttatttctcc ccgatccgtc gtttccccgg cgattccttc ctttacttca   14040
cagtccatag agcttcctaa gcgctgttcg ttttccctcc agcctttcaa aatggaaata   14100
agcttagaag caattccatt tccccggctc tccattttct ctgggtggga gctgccccag   14160
ttaattttaa gccaaagcag atggtaattc atctttggca aaaccaagta aatactgaag   14220
```

```
gtccactctg gagcctctgt gagcaagaag gtgggttgca cttggacttt ctaaaataaa   14280
ccctagggat gtgcacacag cccccagtgc agcagtcaac cacttgctgt tgcttcctct   14340
tatttactcc caggaagcag gtggttagag acacgggtac aaggtatgat ggaagagaag   14400
gcccagacag atgctacaag gtgaacccag aacagctgtc accatgagaa cgtgtgctca   14460
gttaaaagaa caacactgct catctcaggt aacctcagga gctagcattt ggaaagcact   14520
ttagatgtgt ttcccagact ccagaaaata gcacctacca cacagggctt ttaaatgttt   14580
gagcatcata tagcatccct tctaagtatg tggaatgaat taatgaatga accaatagat   14640
gaatgaagta aaggattagt tctaggtagg caaatctgag ccttcgcggc cgccaccgcg   14700
gtggagctcc agcttttgtt ccctttagtg agggttaatt gcgcgcttgg cgtaatcatg   14760
gtcatagctg tttcctgtgt gaaattgtta tccgctcaca attccacaca acatacgagc   14820
cggaagcata aagtgtaaag cctggggtgc ctaatgagtg agctaactca cattaattgc   14880
gttgcgctca ctgcccgctt tccagtcggg aaacctgtcg tgccagctgc attaatgaat   14940
cggccaacgc gcggggagag gcggtttgcg tattgggcgc tcttccgctt cctcgctcac   15000
tgactcgctg cgctcggtcg ttcggctgcg gcgagcggta tcagctcact caaaggcggt   15060
aatacggtta tccacagaat caggggataa cgcaggaaag aacatgtgag caaaaggcca   15120
gcaaaaggcc aggaaccgta aaaaggccgc gttgctggcg tttttccata ggctccgccc   15180
ccctgacgag catcacaaaa atcgacgctc aagtcagagg tggcgaaacc cgacaggact   15240
ataaagatac caggcgtttc cccctggaag ctccctcgtg cgctctcctg ttccgaccct   15300
gccgcttacc ggatacctgt ccgcctttct cccttcggga agcgtggcgc tttctcatag   15360
ctcacgctgt aggtatctca gttcggtgta ggtcgttcgc tccaagctgg gctgtgtgca   15420 cgaaccccc  gttcagcccg accgctgcgc cttatccggt aactatcgtc ttgagtccaa   15480
cccggtaaga cacgacttat cgccactggc agcagccact ggtaacagga ttagcagagc   15540
gaggtatgta ggcggtgcta cagagttctt gaagtggtgg cctaactacg gctacactag   15600
aaggacagta tttggtatct gcgctctgct gaagccagtt accttcggaa aaagagttgg   15660
tagctcttga tccggcaaac aaaccaccgc tggtagcggt ggtttttttg tttgcaagca   15720
gcagattacg cgcagaaaaa aaggatctca agaagatcct ttgatctttt ctacggggtc   15780
tgacgctcag tggaacgaaa actcacgtta agggattttg gtcatgagat tatcaaaaag   15840
gatcttcacc tagatccttt taaattaaaa atgaagtttt aaatcaatct aaagtatata   15900
tgagtaaact tggtctgaca gttattacca atgcttaatc agtgaggcac ctatctcagc   15960
gatctgtcta tttcgttcat ccatagttgc ctgactcccc gtcgtgtaga taactacgat   16020
acgggagggc ttaccatctg gccccagtgc tgcaatgata ccgcgagacc cacgctcacc   16080
ggctccagat ttatcagcaa taaaccagcc agccggaagg gccgagcgca gaagtggtcc   16140
tgcaacttta tccgcctcca tccagtctat taattgttgc cgggaagcta gagtaagtag   16200
ttcgccagtt aatagtttgc gcaacgttgt tgccattgct acaggcatcg tggtgtcacg   16260
ctcgtcgttt ggtatggctt cattcagctc cggttcccaa cgatcaaggc gagttacatg   16320
atcccccatg ttgtgcaaaa aagcggttag ctccttcggt cctccgatcg ttgtcagaag   16380
taagttggcc gcagtgttat cactcatggt tatggcagca ctgcataatt ctcttactgt   16440
catgccatcc gtaagatgct tttctgtgac tggtgagtac tcaaccaagt cattctgaga   16500
atagtgtatg cggcgaccga gttgctcttg cccggcgtca atacgggata taccgcgcc    16560
```

```
acatagcaga actttaaaag tgctcatcat tggaaaacgt tcttcggggc gaaaactctc    16620
aaggatctta ccgctgttga gatccagttc gatgtaaccc actcgtgcac ccaactgatc    16680
ttcagcatct tttactttca ccagcgtttc tgggtgagca aaaacaggaa ggcaaaatgc    16740
cgcaaaaaag ggaataaggg cgacacggaa atgttgaata ctcatactct tcctttttca    16800
atattattga agcatttatc agggttattg tctcatgagc ggatacatat ttgaatgtat    16860
ttagaaaaat aaacaaatag gggttccgcg cacatttccc cgaaaagtgc cac           16913

<210> SEQ ID NO 2
<211> LENGTH: 679
<212> TYPE: DNA
<213> ORGANISM: Artificial
<220> FEATURE:
<223> OTHER INFORMATION: Synthetic DNA

<400> SEQUENCE: 2
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tgggtaccgg     660
gccccccctc gaggtcgac                                                  679

<210> SEQ ID NO 3
<211> LENGTH: 2621
<212> TYPE: DNA
<213> ORGANISM: Mus musculus

<400> SEQUENCE: 3
cctccaggtc ttatccacct caaggggagc taacaaaatt gaattctttg acctgcaaag      60
attcagagcc ccaaacactg ctatttctct tctcctaact cccttaccag gaggcttagt     120
gcaagcattt ggcccaccta gtcccttcc tgctaatcag cttactgcac tagcattagc     180
gagcattcca gggcctacaa actgctggct aggtgtttgt ttggaccttc agaaaacaaa     240
tgaagagatt gtttaggaga tgaaaagatg tattgaacga ggttgtacat tttaagggag     300
aaggccgaga agactctcta atcaagagcc agccaggggt tgttcattaac taccataaat     360 ttggtagtag ggagagagat gtggtcagta actcaatctc tcattcacct aaatgaaaca     420
tgtaagctat ggcaccgcag ccaggatgtg aagaaaacca gtaaagggct aagcaaagac     480
acctccttct aacttaaaca ctacctccaa cacccttatg ttctctaggt agttgctgtt     540
agtattaccc cagaacaggc aatgtcttca gcagaagccc acaaaggcg gtgaattttg     600 acacaagtcc atccctcatc atggattcct gtaaccatcc tctgagaaga gtttttacaa     660
tttcaactca atatgtgaaa ccacaccttc ctttctttag aaaagtatga ttgattatcc     720
atgggaccta ttcacagcac aaagtgactc aaaggcaaaa agcacttggg cttctctggg     780
```

-continued

```
gggcaactgc cctttatctc acacccatgt cttggacaac aaatgttttc ttactctgtc      840 tgtttttct gtcctgctct gtcacataaa atcctgcccg acctttgact caaactccag       900
acagtctacc tgctgatcgc ccggcccctg ttcaaacatg tcctaatact ctgtctctgc      960
aagggtcatc agtagttttc catcttactc aacatcctcc cagtgcttca aagcacctca     1020
ctttatcttc acatccttgt ctctttctaa ttaaagttta aaagttggt ttctaaggct      1080 gatggaggtc taaaaaacaa gcaaatcaaa gacctgaggg tgttctaatt tacttggtag     1140
ttggtcagaa ctaccagtat gttatggtca gagataaatt agggatacta tacttagatc     1200
aaaatttata aaaagacaga gtagagagga tctctgtgag ttcaaggtta gcctggtctt     1260
cgtgcagcga gctccaggct agccaaaggt acaaaatgag attctgtccc taaacagcaa     1320
accaaaaact aaataaaatt gataaatgag catagttcat tatgatgaat gctctttact     1380
tgtgttagac acagggttgg gtgaggcatc acagtgataa cagttacaga tgcacttagg     1440
gtatgacact gcctgcagag cacatttgtc aaggaagact aaagccttct ggccatgtcc     1500
tcagggttta catgacctta tctgaaatgt gtctccagtt caattatctg gaatgtgtgt     1560
ctgcttcagt gcctcacatt ggtagagaaa cattgaccag tgggaggaag ccagacaaca     1620
aagtcctggg aagagaggat tccaggtcct gtgtctgacg aggaatctct caaagaggtg     1680
ggcatgctta tttagcaaaa gaaaatatgc tgtcagaaga ccagtaatca taacaaattt     1740
ataaagaggc tgcgctttgt catggatcga gaatatggga tgtacattaa aaacacacag     1800
acaatcagac gtaccagtag tcatgtaatc tggcttcaga gtgggagaga agtcaggaaa     1860
ccgagatgtc ccaacatggg accccataga ttattttcat gtgaatgtaa ggcaactgct     1920
gtcatcttcc agtttctcaa gacaagccaa agtccaggtt ttaatgcaac gtggttcaat     1980
ttgcaatttt tgcagatatt tcaaaatcct agagaaatgg tagagcctgt ggtcaggtgg     2040
cagtccagct ttgccagttt acgagatcct gggaggcaat tcttagtttc aatggattgt     2100
ggagttcagt agtgtggagt tgacatgtgt gggtgagaga ttttactgga tagtgattcc     2160
tgtatgaaga gggctttcca tcacattctg agcaatggaa agtaatgatg tcaaccttgg     2220
ttgacaatgc acaagagatt ctggagaaag catctccttc ttaggcacag atattgaatg     2280
gaatcatctg acatttgtat tttccagttt ataaaatgcc tttatatctt gtcacattta     2340
aagttcttag aaaatctcct tcaaagagaa atgcgatatt tctgatttac aaatgtgtgg     2400
tctgatatct gagataggaa atcatttcca gaagcaagca ggacattgag tagcagatct     2460
gggattgggt gtgtcagagc ctccaacact gtcagactca aaggtgcagg acaataagta     2520
gtcttactct ggctgtatct tctcattgtt gcttttggac ggttgccctc tttcccaaag     2580
gtgtctgtct gcacatttcg tagagcgagt gttccgatac t                        2621
```

<210> SEQ ID NO 4
<211> LENGTH: 258
<212> TYPE: DNA
<213> ORGANISM: Homo sapiens

<400> SEQUENCE: 4

```
ctaatctccc taggcaaggt tcatatttgt gtaggttact tattctcctt ttgttgacta       60
agtcaataat cagaatcagc aggtttggag tcagcttggc agggatcagc agcctgggtt      120
ggaaggaggg ggtataaaag ccccttcacc aggagaagcc gtcacacaga tccacaagct      180
cctgacagga tggcttctca tcgtctgctc ctcctctgcc ttgctggact ggtatttgtg      240
```

-continued

```
tctgaggctg gccctacg                                                    258

<210> SEQ ID NO 5
<211> LENGTH: 948
<212> TYPE: DNA
<213> ORGANISM: Mus musculus

<400> SEQUENCE: 5
gtgagtgatc ctgtgagcga tccagacatg gcagttagac cttagataaa gaagaagtgc     60
cttcttccag atgtgagaac tagagtactc agactctata tttaccatta gactccaaag    120
agaagagctg gagtgcctct ggctcttcct tctattgctt tagcgcattg ggtctgtagt    180
gctcagtctc tggtgtcctt agataataaa gatatgagat taacatagaa ataaagatat    240
aaaagggctg gatgtatagt ttagtggtcc agtgtatgcc tagtatgtga aaagccttct    300
gttcaacctc tagcaataga aaaacaagat atattctcgg tggggctgtt aatattgaat    360
tctcataaaa tctttaatat atttagtatg cctattatgt tgttatattt tagttcttta    420
gctaatcaaa atgcattatt gatctttctt tgtctttttt tggccaacac tctattccag    480
tctttgaaaa agtcctttaa aagagttaat cagtataatt aaatgagtca ggaagtatgt    540
gagggttatt ttacaaccag agggaattac tatagcaaca gctgattaga atgatctcaa    600
gaaaaagccc attctgtctt tttgcaccat gcacctttca gtggctccat tcagatggag    660
aggcaaacag agcaatggct ctcagagggc ctatttttccc tttgaacatt cattatccat    720
atccctggtg cacagcagtg catctggggg cagaaactgt tcttgctttg gaaacaatgc    780
tgtctatgtc atactggata aagaagctca ttaattgtca acacttatgt tatcataatg    840
ggatcagcat gtactttggg ttttgttcca gagtctatca ccggaaagaa caagccggtt    900
tactctgacc catttcactg acatttctct tgtctcctct gtgcccag                 948

<210> SEQ ID NO 6
<211> LENGTH: 131
<212> TYPE: DNA
<213> ORGANISM: Homo sapiens

<400> SEQUENCE: 6
ggcaccggtg aatccaagtg tcctctgatg gtcaaagttc tagatgctgt ccgaggcagt     60
cctgccatca atgtggccgt gcatgtgttc agaaaggctg ctgatgacac ctgggagcca    120
tttgcctctg g                                                         131

<210> SEQ ID NO 7
<211> LENGTH: 3392
<212> TYPE: DNA
<213> ORGANISM: Mus musculus

<400> SEQUENCE: 7
gtaagcttgt agaaagccca ccatgggacc ggttccaggt tcccatttgc tcttattcgt     60
gttagattca gacacacaca acttaccagc tagagggctc agagagaggg ctcaggggcg    120
aagggcacgt attgctcttg taagagacac aggtttaatt cctagcacca gaatggcagc    180
tcataaccat ctgaaactca cagtcttagg agatctgggt atctgacatt ctcttctacc    240
caccatgtgt gtggtgcaca aattcacatg caggcatcaa atcttataaa caacaacaaa    300
aaaccaacaa acctggtagc aaaagaagat tagaaggtta aacatatgag ccgagagctt    360 ttgtttttgtt ttgtttttgtt ttgtttttgtt tacatttcaa atgttatccc ctttctcggt    420
cccctccccc aaaccctcta ccccattctc tcctcccctt cttctatgag ggtgttcccc    480
```

-continued

```
accaacccac tcccaccttc ctgctctcga attcccctat actgggacat caagccttca     540
cagaatcaag ggcctctcct cccattgatg cccgacaatg tcatcctctg ctacctatgt     600
ggctggagcc atgggtccct tcatgtatcc tccttggttg gtggtttagt ctctgggagg     660
tctgggggat ctggttgatt gatattattg ttcttcctat gagattgcaa accccttcag     720
ctccttcggt cctttaactc ctccactggg gaccccgagc tcagtccaat ggttggctgt     780
gagcatccac cagcagaggc cttttttttt tttttaaca aagctgcttt attatgttgc     840
ttagagcatg accaggaacc agagcacagt ccaagactga agggaggaaa agggggggag     900
tcaataaccc cactgtttca tagtggtttg caaccctttt atatcacagc ccactttagg     960
caaataatga aaattatagt ctccagggac agagaagatg gtgcaggaag tgaagtgcct    1020
gctcagaaaa tggggggcttg aatgtgagtt cccagactct gtgtaagatg cccagcatcg    1080
aagtgcatgc ttataacacc agcctggagg tagaagctta gaaacagggg taccctgaag    1140
ttgcttgttc accagtgtcc ctgaatgggt aggtgcatgt ttggtgagag accctgtctc    1200
aaaaatcaag gtgtaggata attgaaaata cctagctttg agcttagatc atgcaaatgt    1260
gtacacacac tcacacacac cacacacaca aaaaaatgca gagacagaga gatacagaga    1320
gacagagaga tacagagaca gagacagaga gaaaaggaga aagtaaaaaa caaataattt    1380
aaagacccat ggccacaaag aggctcaaag acaagcacgt ataaaaccat acacatgtaa    1440
ttttaggagt tttcagattc cctggtaccc gtgggtgatg cacaagcttt gaatcccagt    1500
cttaaaatct tacgaagaac gtgttcgtgt gtgctaattt attgatgaga ggaaaggaat    1560
tgacaaagtg cccttccgga gcttcctgca ttacccagac tcagggtttt tttaaatgta    1620
cactcagaac agagtagctc tgtgcaaggg tagcaaccac gaagcttaat aagaaacata    1680
tcgtgagaga tctgcaaggc aaatctaggg gctgaccaat ctcacagtca cccactagca    1740
tgtcaacaca acttcccacc tgtgctagcc acttagcaat tttgtgttgt tctgttttgt    1800
ttttgttttt aacaaagcaa tttcaaagag atttctaatt catctaaaca aacaaaccaa    1860
aaggaaaaca gcaaagacgc cctgagcact tagcagagca gctatgcagt tatgactcct    1920
gggtggagac tttatatcag gcttcaactg aatacctaga acctactagt gctcttcatc    1980
aatccttggg aaggtcattt tcttttggtg ctgttttgag tttctatttg ttaatgtctt    2040
cataattata cacgtgttga gcacagcatg caaagtgatt aggggaatct agttggagtg    2100
gaatggatac ccaaatattc agactttctt gtgactcttc tttcttgtac ccacatcaaa    2160 aaaaaaaaa atggagatga gacatggtca gagtcactaa aaccagctgc tacttttaat    2220
tacgtgggga gcagtttcta acattgccat tattgaactg atgctgcctg ggtggaaatg    2280
gaaatcactt agtatttctt gttggcaaag aattactgaa tggattaaat ttccaaaggg    2340
agaagtcagt tacaagtctt ttctttgttt attaggcttt ctgctatgat aaattacact    2400
acttccagaa gttacccctta ggccatggga cactggacta tcactctgct gtcacaagag    2460
attacagagt tagtcaaggc agcttgtgac accttcaggg actgtcataa acttccagca    2520
agtcattaat cctgaatgca atactgtgtg tgtgtgtcta tgtgtgtttg tatgtctgtg    2580
tgtgtcttat gtctgtgtct ctgtgtgtgt gtgtgtttgt gtgtgtgtgt gtatgtatgc    2640
ctgtgtgtgt cttatgtctg tgtttgtgtg tctgtgtgtg tcttatgtct gtgtttgtat    2700
gtctgtgtgt gtctgtgtgt gtcttatgtc tgtgtctctg tgtgtgtgtg tgtgtatgta    2760
tgtatgtatg tatgtatgtg tatgtgtttg catctctctg tgtgtctgcg cttatatatt    2820
```

-continued

```
tgtgtatgtg tttatgtgtt cgcctttgtg cgttgttggg gattgaatcc aggggaatac    2880
aaatgttaag aaagaacgtt accactaagc ttcacctgta ggccttaaag cttttctttc    2940 tttttaaaaat tgtaattaat tcattttcag tcaggatctc cacacctcgt ccctgctgct   3000
ctagaactca ctatttaaac acaatcgccc tcaaacctgc agcaaccctc ccgcctctac    3060
cctgcgagca ctagaataat aacaggtgac cccacacgcc tagattaaga cctttaaggt   3120
aaacatttta ctatatttta gtctcataag acaagatgct acaataaagc tgtacataaa   3180
gttccctcga atttcttgct attttaactc aaacataagg atttcctcct ttttgattca    3240
ggtaacagaa aaaatacaca ggtacataca tgtacacaca tgaacacaca cgcatcacaa    3300
ccacatatgc gcacgcttgt gtgatctatc atttaccatg ccactgaact cttctttccc    3360
cataaattcc tctggacttg tgtgccctcc ag                                  3392

<210> SEQ ID NO 8
<211> LENGTH: 136
<212> TYPE: DNA
<213> ORGANISM: Homo sapiens

<400> SEQUENCE: 8
gaaaaccagt gagtctggag agctgcatgg gctcacaact gaggaggaat ttgtagaagg      60
gatatacaaa gtggaaatag acaccaaatc ttactggaag gcacttggca tctccccatt     120
ccatgagcat gcagag                                                      136

<210> SEQ ID NO 9
<211> LENGTH: 3516
<212> TYPE: DNA
<213> ORGANISM: Mus musculus

<400> SEQUENCE: 9
gtaagtggac acaccaagtt gtttggattt tgtttttagt ctcaggaaat tcccttcgct      60
cttgctgtac gatgggcatg agtggaaagt agattccaca gccagaatcc acagtgctgg     120
gaaagcaagc cttctgaatt tttctaaaac tcatttagca acatggcctg aacctgttca     180
cactgcttat ggtcagctaa ctatatttat gtaaatattc atttctctgt tgaggaaatg     240
ttagtatttg cttttgaggc aacctccaga taccatggag ggcatgtcat agtcaaagag     300
agggctccct atggtatttc tctaaattct ggcatttcct ttattccaaa gcacatctag     360
tgtccccaga agtttgggta gacaattctt ggcaacacag agaattacaa catgttcaaa     420
acccaacagc ttaatatcta aatcatcaag caaacatcac atggcaaagg gatttctgaa     480
tcaaaactgt ttcatcctta tgatcaacct atggaggtct agcctcgact tacacccatt     540
ttaccaataa gctaagagaa gctaagttcc tcatcaagga cacaaggcta gcatgtgtga     600
gcaagtgaca gagttgccct ctatgttggt tagtgtgcct tagccagtgt ctcagtaaga     660
aatggagcta aatcaaaacc caaggccaac agccaaaggc acatgagtaa cctttgcttg     720
gcactgggct cagtttccct ggctcctctc agtcctcagt tcacagaggc agctgtcatg     780
caaatagaat ccaagcttgt tggtcagacc tggagataac aaattccatc aaaaatagct     840
cctcatgtga cctagtttgc tgtctgttgc tatgatacac accatgaccg aaaagcaacc     900
ctggggagag aagggtttat ttcatcttac agcttacagt tcaccatgga ggaaagccag     960 gtggaacct ggaagtggaa attgaagcag agaccagaaa ggaatgctgt ttactggctg     1020
gcttagctcc ttttcttata cagcttaggt ctatgtgccc aggggatggt actgccgagc    1080
ataggctgag cccgcctaca tcaaccatta gtcaaaaaaa ggtccataga cttgcctaca    1140
```

-continued

```
ggccaatctc atggaggcaa taccccagtg gagggtccct cttcgcaggt tactctagtt   1200
tgtgtcaagt tgacaaaacc taaccacaaa gcacaaacag ggtctgccct tgtggcttag   1260
ccatggatga cactctcaga tgatggtgtt accagacaaa ccagaggggc tcaccaagag   1320
tctgccacct accaaggtag tactctactc ctcactgggc accaacaccc atattagctg   1380
ggccagtaca ggacccttgc tgtttcctgc atgaattgtc catagaccct gggtctcagc   1440
ctgccgggag tacctgtaag tagtcgcctc aaacacatta ttcctgttgg aagacttgtc   1500
tgattctctt ttagaactca atcaacaaac gtttttattt tgttttggct ttttggagac   1560
aagatctctc ataggccagc ctgacttgaa tgtagctgag gatgacctgt gctgctaatc   1620
ttctcgcctc ttcctcccaa gtggtaggat aataggcata agacaccaca gcagttttac   1680
tccataccag ggctctgaac ccagacttta aacactctat caactgattc acattcccac   1740
cccatcattc aacaaacatt tgaaaaataa aaccCttctg ccttgagcac tctgctaaat   1800
acagcctttg agtgcggagt atttcctcac aaccagggtc caagatgacc ccatcataca   1860
taccacggaa aattaggaga tgttttttagg tctctttgct tggggtaatt tttatgtgtg   1920
tgtgtacaca gccctgtgcg tgtgtgtgtg tgtgtgtgtg tgtgtgtaca ggcacacacg   1980
tgtatgcatg tagaggctac ataaaaacct taggtgtcat tctcaggcac tctgttcacc   2040
ccttcacaca gcccgaacac acaaaatttg aggcattagc ctggagctca ccagttaggc   2100
tagactgact tgccagcaga ccccaggctg tctccatctc cccagctctg ggattacaaa   2160
ctctatcata ccagacattt ttatacatat tctgagcata aaattcatgt cttcaggcta   2220
acaagtcaag agcttaaatg actgagctct cttacgtggt ggattttttt taaaactaca   2280
taatatcttt tttttttttt tcacttctgg ggaagaaaca aatgagcctg agtgacaatg   2340
cgacagaaaa gaaatttga ggagtgtgtg tgtctgtgtg tgtggtggca catgcctctc   2400
atctaatgct agaggctaca gtagaatgct cctgaattag tggccagcca aggccaaggg   2460
ctagggttgt aactcagtgg cagagggctt gcctagcatt cgcaggattt gatccatagc   2520
gctataaata ataataaata aatacaacag tctaagatga ttctcccttt catttatctg   2580
gatgttattt ttgtgttagt tttactctgt catccaatca ttgtttgccc tatatttgga   2640
catttaaaaa aaatctttat tccaagtgtg ttcaaagctg tatccaaaac ctgtccacca   2700
aatgagtcca atgacataca tcttctatat taccatctgt tccagatttg gctgactccc   2760
ggcacctggg ctgttgctgc acccatgtct cagatagtct agtgatttga gaagtgacta   2820
gtaattgcaa aatccagact ttgtccagaa acttctatga gctccaaaac tttcatttac   2880
atttctgcca gccacaaacc gcttgtgttg tggagagaac cctgtgatgt cttcccacag   2940
catctcagcc ttgtttcttc ccttaaaata ttcatctttt cacattagaa catgcaaagg   3000
gacagtggga gcgaaacccc tggactggga cgcacgaagc cttcctttct ggtcaggctc   3060
tcactgtaga aacttaggcc ggtttcagca tgcagtctgc tggagaatgg ctcctgccaa   3120
cattccaggt ctggaagttt gtagtggagt tgttgataac cactgttcgc cacaggtctt   3180
ttgtttgtgg gtgtcagtgt ttctactctc ctgactttta tctgaaccca agaaagggaa   3240
caatagcctt caagctctct gtgactctga tctgaccagg gccacccaca ctgcagaagg   3300
aaacttgcaa agagagacct gcaattctct aagagctcca cacagctcca aagacttagg   3360
cagcatattt taatctaatt attcgtcccc caacccacc ccagaggaca gttagacaat   3420
aaaaggaaga ttaccagctt agcatcctgt gaacactttg tctgcagctc ctacctctgg   3480
```

-continued

```
gctctgttag aactagctgt ctctcctctc tcctag                        3516

<210> SEQ ID NO 10
<211> LENGTH: 696
<212> TYPE: DNA
<213> ORGANISM: Homo sapiens

<400> SEQUENCE: 10
gtggtattca cagccaacga ctccggcccc cgccgctaca ccattgccgc cctgctgagc    60
ccctactcct attccaccac ggctgtcgtc accaatccca aggaatgaga gactcagccc   120
aggaggacca ggatcttgcc aaagcagtag catcccattt gtaccaaaac agtgttcttg   180
ctctataaac cgtgttagca gctcaggaag atgccgtgaa gcattcttat taaaccacct   240
gctatttcat tcaaactgtg tttctttttt atttcctcat tttctcccc tgctcctaaa    300 acccaaaatc ttctaaagaa ttctagaagg tatgcgatca aactttttaa agaaagaaaa   360
tactttttga ctcatggttt aaaggcatcc tttccatctt ggggaggtca tgggtgctcc   420
tggcaacttg cttgaggaag ataggtcaga aagcagagtg gaccaaccgt tcaatgtttt   480
acaagcaaaa catacactaa gcatggtctg tagctattaa aagcacacaa tctgaagggc   540
tgtagatgca cagtagtgtt ttcccagagc atgttcaaaa gccctgggtt caatcacaat   600
actgaaaagt aggccaaaaa acattctgaa aatgaaatat ttgggttttt ttttataacc   660
tttagtgact aaataaagac aaatctaaga gactaa                            696

<210> SEQ ID NO 11
<211> LENGTH: 2308
<212> TYPE: DNA
<213> ORGANISM: Mus musculus

<400> SEQUENCE: 11
ctgtggctgc ttatatcatg ttaatttggg tccccaaaat tgtttgtatg aacatccaca    60
ctggtaaata aagttgtggc acccaatggc tgggcagggt agatggaggc aggacttta    120 gattcctggg ggagggagaa agaaggagga atcaccatgc ctagagaagg agaggagaaa   180
caccatgcct ggaaaggtgc gggacagaga acatagccac catgtaggag caggaggata   240
gcagccaaag agggctgtac gtctgggtct ggggtggcca agagagaatg taggagttag   300
taaagtaata actcgggaat atcggaggga ggtggattag ccacatggag gttaggaagt   360
ggcccagcca ttgagctgat taaagcatat caaaatataa agaccctgtg cgtgtgtgtg   420
tgtgtgtgtg tgtgtgtgtg tgtgtgtgtg tgtttcattt gagaaccaag aacattcggg   480
caagtagtga ggaatgagcc tcagcaggtg ggatctatta aagtatttaa ttgggtatac   540
tacaactgat tcttcaggca tttcttgtta agcactttac tcatttgagg gccataacag   600
tttctttgca caagaatggg cctatccgca gtcaggcctg ggactccggg ccccacccct   660
tgctgctgag ctatttataa tgatacattc aggtagaagg ggagtcatgg tcttcagttg   720
tgtgctcact ggtgactcca ccaggctctg atggacagtt ccaagccaaa atgaagaaac   780
aagccacaaa acgacatgaa tctgggagaa gggttggtgg taacgtgcgg aggggttggg   840
aggtgggagg cagctaagag atgacaagga agggagcatc agcgtgggct gtgtgcatgc   900
ataaaacgaa agcaaacaaa atcaatcact aaaccatgtt taagaacagt gagttccaaa   960
gggataaacc tgcagcaacc cagcttcact tcccaggcaa ttcctacctt cccatcacag   1020
ttcatagaac atattcctcc taaactggca attttccttc cagtctttca aaatgaaata   1080
agcttggaat caattccact tccccagatc tctctacccc tctaatccac tttagaccaa   1140
```

-continued

```
ttctacctga atcagaaccc agctctcagg agacagaagc agagacagga ggatgtccat      1200
gagttcaagg ccattctagt gagttctaag ccaaccaaaa ctacataatg agaccttgtc      1260
taacaacaac ttagtcaaat cctaaatcca tgtttaattg atacacacac tcatgcacac      1320
gcacacacac gtgtaatatg aacaaaacga aacaaaatag atttgtaatg gacgagaata      1380
aattcaattt taaccactct gggtttaata taatcagact ggttttttaaa ctctaaagtt      1440 ggcagtgtgt gcacacacat gtccaacgca tggaggtgtg tctcaaaaag cataattata      1500
agtattgaac tcctacctgc aacatttgat agcacctgtc aaacaaggaa atgaagcata      1560
tcttttgcct caagctatat tttatccacc gagcgctcgt agcagaggca gaattatttc      1620
tccccgatcc gtcgtttccc cggcgattcc ttcctttact tcacagtcca tagagcttcc      1680
taagcgctgt tcgtttttccc tccagccttt caaaatggaa ataagcttag aagcaattcc      1740 atttcccccgg ctctccattt tctctgggtg ggagctgccc cagttaattt taagccaaag      1800
cagatggtaa ttcatctttg gcaaaaccaa gtaaatactg aaggtccact ctggagcctc      1860
tgtgagcaag aaggtgggtt gcacttggac tttctaaaat aaaccctagg gatgtgcaca      1920
cagcccccag tgcagcagtc aaccacttgc tgttgcttcc tcttatttac tcccaggaag      1980
caggtggtta gagacacggg tacaaggtat gatggaagag aaggcccaga cagatgctac      2040
aaggtgaacc cagaacagct gtcaccatga gaacgtgtgc tcagttaaaa gaacaacact      2100
gctcatctca ggtaacctca ggagctagca tttggaaagc actttagatg tgtttcccag      2160
actccagaaa atagcaccta ccacacaggg cttttaaatg tttgagcatc atatagcatc      2220
ccttctaagt atgtggaatg aattaatgaa tgaaccaata gatgaatgaa gtaaaggatt      2280
agttctaggt aggcaaatct gagccttc                                        2308
```

```
<210> SEQ ID NO 12
<211> LENGTH: 2228
<212> TYPE: DNA
<213> ORGANISM: Artificial
<220> FEATURE:
<223> OTHER INFORMATION: Synthetic DNA

<400> SEQUENCE: 12
```

```
gcggccgcca ccgcggtgga gctccagctt ttgttccctt tagtgagggt taattgcgcg       60
cttggcgtaa tcatggtcat agctgtttcc tgtgtgaaat tgttatccgc tcacaattcc      120
acacaacata cgagccggaa gcataaagtg taaagcctgg ggtgcctaat gagtgagcta      180
actcacatta attgcgttgc gctcactgcc cgctttccag tcgggaaacc tgtcgtgcca      240
gctgcattaa tgaatcggcc aacgcgcggg gagaggcggt ttgcgtattg ggcgctcttc      300
cgcttcctcg ctcactgact cgctgcgctc ggtcgttcgg ctgcggcgag cggtatcagc      360
tcactcaaag gcggtaatac ggttatccac agaatcaggg gataacgcag gaaagaacat      420
gtgagcaaaa ggccagcaaa aggccaggaa ccgtaaaaag gccgcgttgc tggcgttttt      480
ccataggctc cgcccccctg acgagcatca caaaaatcga cgctcaagtc agaggtggcg      540
aaacccgaca ggactataaa gataccaggc gtttccccct ggaagctccc tcgtgcgctc      600
tcctgttccg accctgccgc ttaccggata cctgtccgcc tttctccctt cgggaagcgt      660
ggcgctttct catagctcac gctgtaggta tctcagttcg gtgtaggtcg ttcgctccaa      720
gctgggctgt gtgcacgaac cccccgttca gcccgaccgc tgcgccttat ccggtaacta      780
tcgtcttgag tccaacccgg taagacacga cttatcgcca ctggcagcag ccactggtaa      840
```

-continued

```
caggattagc agagcgaggt atgtaggcgg tgctacagag ttcttgaagt ggtggcctaa      900
ctacggctac actagaagga cagtatttgg tatctgcgct ctgctgaagc cagttacctt      960
cggaaaaaga gttggtagct cttgatccgg caaacaaacc accgctggta gcggtggttt     1020
ttttgtttgc aagcagcaga ttacgcgcag aaaaaaagga tctcaagaag atcctttgat     1080
cttttctacg gggtctgacg ctcagtggaa cgaaaactca cgttaaggga ttttggtcat     1140
gagattatca aaaaggatct tcacctagat ccttttaaat taaaaatgaa gttttaaatc     1200
aatctaaagt atatatgagt aaacttggtc tgacagttat taccaatgct taatcagtga     1260
ggcacctatc tcagcgatct gtctatttcg ttcatccata gttgcctgac tccccgtcgt     1320
gtagataact acgatacggg agggcttacc atctggcccc agtgctgcaa tgataccgcg     1380
agacccacgc tcaccggctc cagatttatc agcaataaac cagccagccg gaagggccga     1440
gcgcagaagt ggtcctgcaa ctttatccgc ctccatccag tctattaatt gttgccggga     1500
agctagagta agtagttcgc cagttaatag tttgcgcaac gttgttgcca ttgctacagg     1560
catcgtggtg tcacgctcgt cgtttggtat ggcttcattc agctccggtt cccaacgatc     1620
aaggcgagtt acatgatccc ccatgttgtg caaaaaagcg gttagctcct tcggtcctcc     1680
gatcgttgtc agaagtaagt tggccgcagt gttatcactc atggttatgg cagcactgca     1740
taattctctt actgtcatgc catccgtaag atgcttttct gtgactggtg agtactcaac     1800
caagtcattc tgagaatagt gtatgcggcg accgagttgc tcttgcccgg cgtcaatacg     1860
ggataatacc gcgccacata gcagaacttt aaaagtgctc atcattggaa aacgttcttc     1920
ggggcgaaaa ctctcaagga tcttaccgct gttgagatcc agttcgatgt aacccactcg     1980
tgcacccaac tgatcttcag catcttttac tttcaccagc gtttctgggt gagcaaaaac     2040
aggaaggcaa aatgccgcaa aaaagggaat aagggcgaca cggaaatgtt gaatactcat     2100
actcttcctt tttcaatatt attgaagcat ttatcagggt tattgtctca tgagcggata     2160
catatttgaa tgtatttaga aaaataaaca ataggggtt ccgcgcacat ttccccgaaa      2220
agtgccac                                                             2228
```

```
<210> SEQ ID NO 13
<211> LENGTH: 23
<212> TYPE: DNA
<213> ORGANISM: Artificial
<220> FEATURE:
<223> OTHER INFORMATION: Synthetic DNA

<400> SEQUENCE: 13
ctgctcctcc tctgccttgc tgg                                               23

<210> SEQ ID NO 14
<211> LENGTH: 23
<212> TYPE: DNA
<213> ORGANISM: Artificial
<220> FEATURE:
<223> OTHER INFORMATION: Synthetic DNA

<400> SEQUENCE: 14
gcagaggagg agcagacgat gag                                               23

<210> SEQ ID NO 15
<211> LENGTH: 48
<212> TYPE: DNA
<213> ORGANISM: Artificial
<220> FEATURE:
<223> OTHER INFORMATION: Synthetic DNA
```

-continued

```
<400> SEQUENCE: 15
caccctgctc ctcctctgcc ttgcgacgag gaggagacgg aacgcaaa                48

<210> SEQ ID NO 16
<211> LENGTH: 48
<212> TYPE: DNA
<213> ORGANISM: Artificial
<220> FEATURE:
<223> OTHER INFORMATION: Synthetic DNA

<400> SEQUENCE: 16
caccgcaaag gaggaagagt cgaacgtttc ctccttctca gcttcaaa                48

<210> SEQ ID NO 17
<211> LENGTH: 23
<212> TYPE: DNA
<213> ORGANISM: Artificial
<220> FEATURE:
<223> OTHER INFORMATION: Synthetic DNA

<400> SEQUENCE: 17
ctgcgatggt gtagtggcga tgg                                          23

<210> SEQ ID NO 18
<211> LENGTH: 23
<212> TYPE: DNA
<213> ORGANISM: Artificial
<220> FEATURE:
<223> OTHER INFORMATION: Synthetic DNA

<400> SEQUENCE: 18
gtggcgatgg ccagagtcgt tgg                                          23

<210> SEQ ID NO 19
<211> LENGTH: 48
<212> TYPE: DNA
<213> ORGANISM: Artificial
<220> FEATURE:
<223> OTHER INFORMATION: Synthetic DNA

<400> SEQUENCE: 19
caccctgcga tggtgtagtg gcgagacgct accacatcac cgctcaaa                48

<210> SEQ ID NO 20
<211> LENGTH: 48
<212> TYPE: DNA
<213> ORGANISM: Artificial
<220> FEATURE:
<223> OTHER INFORMATION: Synthetic DNA

<400> SEQUENCE: 20
caccgtggcg atggccagag tcgtcaccgc taccggtctc agcacaaa                48

<210> SEQ ID NO 21
<211> LENGTH: 24
<212> TYPE: DNA
<213> ORGANISM: Artificial
<220> FEATURE:
<223> OTHER INFORMATION: Synthetic DNA

<400> SEQUENCE: 21
ggattgtgga gttcagtagt gtgg                                         24

<210> SEQ ID NO 22
```

```
<211> LENGTH: 19
<212> TYPE: DNA
<213> ORGANISM: Artificial
<220> FEATURE:
<223> OTHER INFORMATION: Synthetic DNA

<400> SEQUENCE: 22
ctgagcaggc acttcactt                                                    19

<210> SEQ ID NO 23
<211> LENGTH: 26
<212> TYPE: DNA
<213> ORGANISM: Artificial
<220> FEATURE:
<223> OTHER INFORMATION: Synthetic DNA

<400> SEQUENCE: 23
agcgagtgtt ccgatactct aatctc                                            26

<210> SEQ ID NO 24
<211> LENGTH: 24
<212> TYPE: DNA
<213> ORGANISM: Artificial
<220> FEATURE:
<223> OTHER INFORMATION: Synthetic DNA

<400> SEQUENCE: 24
atggctctca gagggcctat tttc                                              24

<210> SEQ ID NO 25
<211> LENGTH: 97
<212> TYPE: DNA
<213> ORGANISM: Mus musculus

<400> SEQUENCE: 25
aagctcctga caggatggct tcccttcgac tcttcctcct ttgcctcgct ggactggtat       60
ttgtgtctga agctggcccc gcggtgagtg atcctgt                                97

<210> SEQ ID NO 26
<211> LENGTH: 97
<212> TYPE: DNA
<213> ORGANISM: Homo sapiens

<400> SEQUENCE: 26
aagctcctga caggatggct tctcatcgtc tgctcctcct ctgccttgct ggactggtat       60
ttgtgtctga ggctggccct acggtgagtg atcctgt                                97

<210> SEQ ID NO 27
<211> LENGTH: 131
<212> TYPE: DNA
<213> ORGANISM: Mus musculus

<400> SEQUENCE: 27
ggtgctggag aatccaaatg tcctctgatg gtcaaagtcc tggatgctgt ccgaggcagc       60
cctgctgtag acgtggctgt aaaagtgttc aaaaagacct ctgagggatc ctgggagccc      120
tttgcctctg g                                                           131

<210> SEQ ID NO 28
<211> LENGTH: 131
<212> TYPE: DNA
<213> ORGANISM: Homo sapiens

<400> SEQUENCE: 28
```

-continued

```
ggcaccggtg aatccaagtg tcctctgatg gtcaaagttc tagatgctgt ccgaggcagt      60
cctgccatca atgtggccgt gcatgtgttc agaaaggctg ctgatgacac ctgggagcca     120
tttgcctctg g                                                          131

<210> SEQ ID NO 29
<211> LENGTH: 23
<212> TYPE: DNA
<213> ORGANISM: Artificial
<220> FEATURE:
<223> OTHER INFORMATION: Synthetic DNA

<400> SEQUENCE: 29
aacaggtgac cccacacgcc tag                                              23

<210> SEQ ID NO 30
<211> LENGTH: 20
<212> TYPE: DNA
<213> ORGANISM: Artificial
<220> FEATURE:
<223> OTHER INFORMATION: Synthetic DNA

<400> SEQUENCE: 30
actggctaag gcacactaac                                                  20

<210> SEQ ID NO 31
<211> LENGTH: 25
<212> TYPE: DNA
<213> ORGANISM: Artificial
<220> FEATURE:
<223> OTHER INFORMATION: Synthetic DNA

<400> SEQUENCE: 31
tatgcgcacg cttgtgtgat ctatc                                            25

<210> SEQ ID NO 32
<211> LENGTH: 135
<212> TYPE: DNA
<213> ORGANISM: Mus musculus

<400> SEQUENCE: 32
aagaccgcgg agtctggaga gctgcacggg ctcaccacag atgagaagtt tgtagaagga      60
gtgtacagag tagaactgga caccaaatcg tactggaaga cacttggcat ttccccgttc     120
catgaattcg cggat                                                      135

<210> SEQ ID NO 33
<211> LENGTH: 135
<212> TYPE: DNA
<213> ORGANISM: Homo sapiens

<400> SEQUENCE: 33
aaaaccagtg agtctggaga gctgcatggg ctcacaactg aggaggaatt tgtagaaggg      60
atatacaaag tggaaataga caccaaatct tactggaagg cacttggcat ctccccattc     120
catgagcatg cagag                                                      135

<210> SEQ ID NO 34
<211> LENGTH: 20
<212> TYPE: DNA
<213> ORGANISM: Artificial
<220> FEATURE:
<223> OTHER INFORMATION: Synthetic DNA
```

-continued

<400> SEQUENCE: 34
gtatccaaaa cctgtccacc                                                   20

<210> SEQ ID NO 35
<211> LENGTH: 22
<212> TYPE: DNA
<213> ORGANISM: Artificial
<220> FEATURE:
<223> OTHER INFORMATION: Synthetic DNA

<400> SEQUENCE: 35
gcagccacag ttagtctctt ag                                                22

<210> SEQ ID NO 36
<211> LENGTH: 23
<212> TYPE: DNA
<213> ORGANISM: Artificial
<220> FEATURE:
<223> OTHER INFORMATION: Synthetic DNA

<400> SEQUENCE: 36
ccacacagct ccaaagactt agg                                               23

<210> SEQ ID NO 37
<211> LENGTH: 108
<212> TYPE: DNA
<213> ORGANISM: Mus musculus

<400> SEQUENCE: 37
gtggttttca cagccaacga ctctggccat cgccactaca ccatcgcagc cctgctcagc      60
ccatactcct acagcaccac ggctgtcgtc agcaacccc agaattga                    108

<210> SEQ ID NO 38
<211> LENGTH: 108
<212> TYPE: DNA
<213> ORGANISM: Homo sapiens

<400> SEQUENCE: 38
gtggtattca cagccaacga ctccggcccc cgccgctaca ccattgccgc cctgctgagc      60
ccctactcct attccaccac ggctgtcgtc accaatccca aggaatga                   108

<210> SEQ ID NO 39
<211> LENGTH: 25
<212> TYPE: DNA
<213> ORGANISM: Artificial
<220> FEATURE:
<223> OTHER INFORMATION: Synthetic DNA

<400> SEQUENCE: 39
ctaatctccc taggcaaggt tcata                                             25

<210> SEQ ID NO 40
<211> LENGTH: 25
<212> TYPE: DNA
<213> ORGANISM: Artificial
<220> FEATURE:
<223> OTHER INFORMATION: Synthetic DNA

<400> SEQUENCE: 40
aagccatcct gtcaggagct tgtgg                                             25

<210> SEQ ID NO 41
<211> LENGTH: 23

```
<212> TYPE: DNA
<213> ORGANISM: Artificial
<220> FEATURE:
<223> OTHER INFORMATION: Synthetic DNA

<400> SEQUENCE: 41
ggtcagaagg actcctatgt ggg                                         23

<210> SEQ ID NO 42
<211> LENGTH: 20
<212> TYPE: DNA
<213> ORGANISM: Artificial
<220> FEATURE:
<223> OTHER INFORMATION: Synthetic DNA

<400> SEQUENCE: 42
atgaggtagt ctgtcaggtc                                             20

<210> SEQ ID NO 43
<211> LENGTH: 52
<212> TYPE: DNA
<213> ORGANISM: Artificial
<220> FEATURE:
<223> OTHER INFORMATION: Synthetic DNA

<400> SEQUENCE: 43
ggcaccggtg aatccaagtg tcctctgatg gtcaaagttc tagatgctgt cc          52

<210> SEQ ID NO 44
<211> LENGTH: 23
<212> TYPE: DNA
<213> ORGANISM: Artificial
<220> FEATURE:
<223> OTHER INFORMATION: Synthetic DNA

<400> SEQUENCE: 44
tgaatccaag tgtcctctga tgg                                         23

<210> SEQ ID NO 45
<211> LENGTH: 42
<212> TYPE: DNA
<213> ORGANISM: Artificial
<220> FEATURE:
<223> OTHER INFORMATION: Synthetic DNA/RNA

<400> SEQUENCE: 45
tgaatccaag tgtcctctga guuuuagagc uaugcuguuu ug                     42

<210> SEQ ID NO 46
<211> LENGTH: 69
<212> TYPE: RNA
<213> ORGANISM: Artificial
<220> FEATURE:
<223> OTHER INFORMATION: Synthetic DNA

<400> SEQUENCE: 46
aaacagcaua gcaaguuaaa auaaggcuag uccguuauca acuugaaaaa guggcaccga   60
gucggugcu                                                         69

<210> SEQ ID NO 47
<211> LENGTH: 123
<212> TYPE: DNA
<213> ORGANISM: Artificial
<220> FEATURE:
<223> OTHER INFORMATION: Synthetic DNA
```

```
<400> SEQUENCE: 47
tgacccattt cactgacatt tctcttgtct cctctgtgcc cagggcaccg gtgaatccaa          60
atgtcctctg atggtcaaag ttctagatgc tgtccgaggc agtcctgcca tcaatgtggc         120
cgt                                                                        123

<210> SEQ ID NO 48
<211> LENGTH: 23
<212> TYPE: DNA
<213> ORGANISM: Artificial
<220> FEATURE:
<223> OTHER INFORMATION: Synthetic DNA

<400> SEQUENCE: 48
tccactcatt cttggcagga tgg                                                   23

<210> SEQ ID NO 49
<211> LENGTH: 19
<212> TYPE: DNA
<213> ORGANISM: Artificial
<220> FEATURE:
<223> OTHER INFORMATION: Synthetic DNA

<400> SEQUENCE: 49
ctcattcttg gcaggatgg                                                        19

<210> SEQ ID NO 50
<211> LENGTH: 40
<212> TYPE: DNA
<213> ORGANISM: Artificial
<220> FEATURE:
<223> OTHER INFORMATION: Synthetic DNA

<400> SEQUENCE: 50
caccctcatt cttggcagga gagtaagaac cgtcctcaaa                                 40

<210> SEQ ID NO 51
<211> LENGTH: 23
<212> TYPE: DNA
<213> ORGANISM: Artificial
<220> FEATURE:
<223> OTHER INFORMATION: Synthetic DNA

<400> SEQUENCE: 51
tgaatccaaa tgtcctctga tgg                                                   23

<210> SEQ ID NO 52
<211> LENGTH: 48
<212> TYPE: DNA
<213> ORGANISM: Artificial
<220> FEATURE:
<223> OTHER INFORMATION: Synthetic DNA

<400> SEQUENCE: 52
cacctgaatc caaatgtcct ctgaaggtga gtaagaaccg tcctcaaa                        48
```